US011266726B2

(12) United States Patent
Wood et al.

(10) Patent No.: US 11,266,726 B2
(45) Date of Patent: Mar. 8, 2022

(54) COMPOSITIONS AND METHODS FOR THE TREATMENT OF HER2-EXPRESSING SOLID TUMORS

(71) Applicants: The U.S.A., as represented by the Secretary, Department of Health and Human Services, Bethesda, MD (US); Baylor College of Medicine, Houston, TX (US)

(72) Inventors: Lauren V. Wood, Bethesda, MD (US); Brenda D. Roberson, Frederick, MD (US); Jay A. Berzofsky, Bethesda, MD (US); John C. Morris, Cincinnati, OH (US); Jason C. Steel, Queensland (AU); Masaki Terabe, Potomac, MD (US); Malcolm K. Brenner, Houston, TX (US)

(73) Assignees: The United States of America, as represented by the Secretary, Department of Health and Human Services, Bethesda, MD (US); Baylor College of Medicine, Houston, TX (US)

(*) Notice: Subject to any disclaimer, the term of this patent is extended or adjusted under 35 U.S.C. 154(b) by 593 days.

(21) Appl. No.: 15/771,932

(22) PCT Filed: Oct. 31, 2016

(86) PCT No.: PCT/US2016/059680
§ 371 (c)(1),
(2) Date: Apr. 27, 2018

(87) PCT Pub. No.: WO2017/075570
PCT Pub. Date: May 4, 2017

(65) Prior Publication Data
US 2018/0344828 A1 Dec. 6, 2018

Related U.S. Application Data

(60) Provisional application No. 62/248,964, filed on Oct. 30, 2015.

(51) Int. Cl.
*A61K 39/00* (2006.01)
*A61P 35/00* (2006.01)
*A61K 35/761* (2015.01)

(52) U.S. Cl.
CPC .. *A61K 39/0011* (2013.01); *A61K 39/001106* (2018.08); *A61P 35/00* (2018.01); *A61K 2039/5154* (2013.01); *A61K 2039/5256* (2013.01)

(58) Field of Classification Search
CPC ........ A61K 39/0011; A61K 39/001106; A61K 2039/5154; A61P 35/00
See application file for complete search history.

(56) References Cited

U.S. PATENT DOCUMENTS

| 7,662,586 B2 | 2/2010 | Monaci et al. | |
|---|---|---|---|
| 7,741,099 B2 | 6/2010 | Havenga et al. | |
| 8,835,613 B2 | 9/2014 | Berzofsky et al. | |
| 2005/0158278 A1* | 7/2005 | Vogels | A61P 31/16 424/93.2 |
| 2010/0285072 A1* | 11/2010 | Felzmann | C12N 5/064 424/278.1 |
| 2011/0287038 A1* | 11/2011 | Slawin | A61P 43/00 424/184.1 |
| 2016/0361364 A1* | 12/2016 | Corbascio | A61K 35/28 |

FOREIGN PATENT DOCUMENTS

WO  WO 2004/041065  5/2004

OTHER PUBLICATIONS

Wood et al, J Clin Oncol, 35: Suppl15, 3089, May 2017.*
Akiyoshi et al., "Effect of Autologous Plasma from Patients with Malignant Tumor on Macrophage Migration Inhibition with Tumor Extract," *Gann*, vol. 69:57-60, 1978.
Berzofsky et al., "Cancer vaccine strategies: Translation from mice to clinical trials," Keystone Symposium on Tumor Immunology, Banff, Alberta, Canada, Feb. 10, 2015 (26 pages).
ClinicalTrials.gov Identifier NCT01730118, "Ad/HER2/Neu Dendritic Cell Cancer Vaccine Testing," posted Nov. 21, 2012 (21 pages).
Kim et al., "Enhanced Antitumor Immunotherapeutic Effect of B-Cell-Based Vaccine Transduced with Modified Adenoviral Vector Containing Type 35 Fiber Structures," *Gene Ther.*, vol. 21:106-114, 2014.
Leen et al., "Monoculture-Derived T Lymphocytes Specific for Multiple Viruses Expand and Produce Clinically Relevant Effects in Immunocompromised Individuals," *Nature Med.*, vol. 12:1160-1166, 2006.
Norell et al., "Vaccination with a Plasmid DNA Encoding HER-2/neu Together with Low Doses of GM-CSF and IL-2 in Patients with Metastatic Breast Carcinoma: A Pilot Clinical Trial," *J. Translat. Med.*, vol. 8:53, 2010.
Park et al., "Early Role of CD4+ Th1 Cells and Antibodies in HER-2 Adenovirus Vaccine Protection against Autochthonous Mammary Carcinomas," *J. Immunol.*, vol. 174:4228-4236, 2005.
Park et al., "Therapy of Advanced Established Murine Breast Cancer with a Recombinant Adenoviral ErbB-2/neu Vaccine," *Cancer Res.*, vol. 68:1979-1987, 2008.

(Continued)

*Primary Examiner* — Mark Halvorson
(74) *Attorney, Agent, or Firm* — Klarquist Sparkman, LLP

(57) ABSTRACT

Recombinant adenoviruses expressing the extracellular (EC) and transmembrane (TM) domains of human HER2 (HER2ECTM) are described. The recombinant adenoviruses express a chimeric fiber protein having the adenovirus type 35 (Ad5) shaft and knob domains, which facilitates transduction of human dendritic cells by the recombinant HER2ECTM expressing adenovirus. Compositions that include dendritic cells transduced by the recombinant adenovirus and their use for treating HER-positive tumors is described.

14 Claims, 13 Drawing Sheets

Specification includes a Sequence Listing.

(56) References Cited

OTHER PUBLICATIONS

Sakai et al., "Vaccination by Genetically Modified Dendritic Cells Expressing a Truncated neu Oncogene Prevents Development of Breast Cancer in Transgenic Mice," *Cancer Res.*, vol. 64:8022-8028, 2004.

Sas et al., "Vaccination of Fiber-Modified Adenovirus-Transfected Dendritic Cells to Express HER-2/neu Stimulates Efficient HER-2/neu-specific Humoral and CTL Responses and Reduces Breast Carcinogenesis in Transgenic Mice," *Cancer Gene Ther.*, vol. 15:655-666, 2008.

Shayakhmetov et al., "A High-Capacity, Capsid-Modified Hybrid Adenovirus/Adeno-Associated Virus Vector for Stable Transduction of Human Hematopoietic Cells," *J. Virol.*, vol. 76:1135-1143, 2002.

Slager et al., "Induction of CAMEL/NY-ESO-ORF2-Specific CD8+ T Cells Upon Stimulation with Dendritic Cells Infected with a Modified Ad5 Vector Expressing a Chimeric Ad5/35 Fiber," *Cancer Gene Ther.*, vol. 11:227-236, 2004.

Vigouroux et al., "Induction of Antigen-Specific Regulatory T Cells following Overexpression of a Notch Ligand by Human B Lymphocytes," *J. Virol.*, vol. 77:10872-10880, 2003.

Yotnda et al., "Efficient Infection of Primitive Hematopoietic Stem Cells by Modified Adenovirus," *Gene Ther.*, vol. 8:930-937, 2001.

Foley et al., "Genetically Modified Dendritic Cells in Cancer Therapy: Implications for Transfusion Medicine," *Transfus Med Rev* 15(4): 292-304, 2001.

Kim et al., "A phase 1 study of a heterologous prime-boost vaccination involving a truncated HER2 sequence in patients with HER2-expressing breast cancer," *Mol Ther Methods Clin Dev* 2:15031, 2015.

* cited by examiner

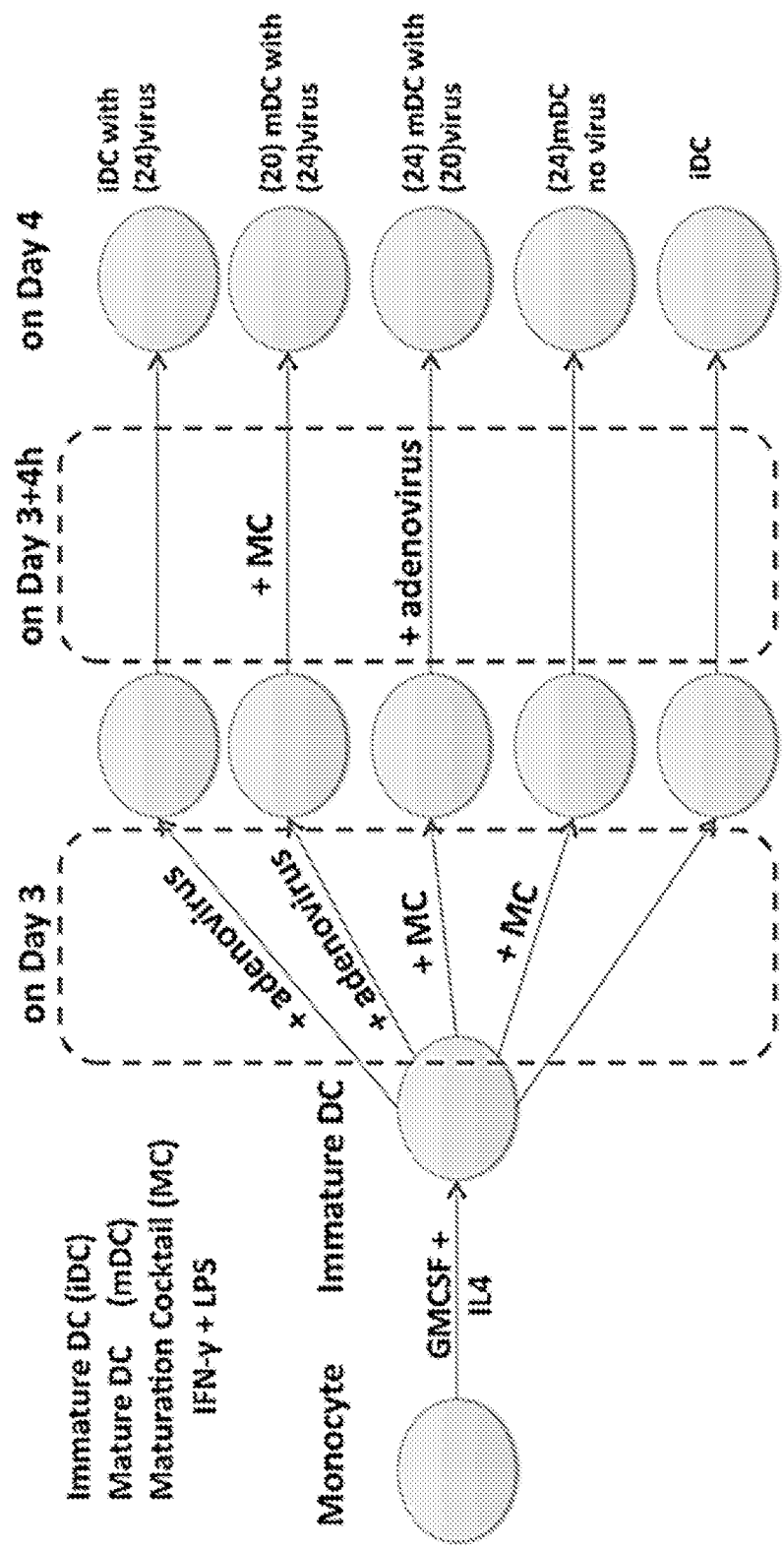

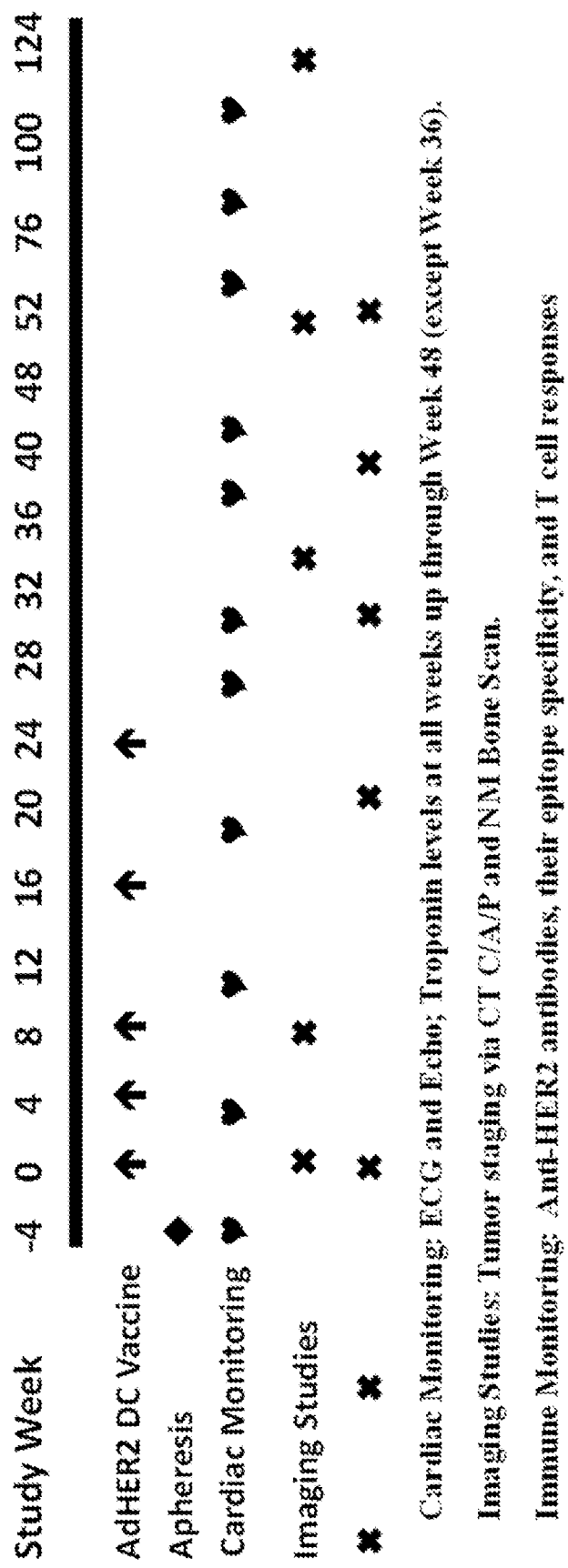

FIG. 7

13-C-0016 DC Vaccine Final Release Product: Autologus Plasma vs. AB Allogeneic Plasma

| Study # | Product Extension | Plasma | %CD83+ of 7-AAD Viable DC ≥ 60% | Release Viability ≥ 60% | %CD340+ Cells | CD340+ MFI (Mean Fluorescent Intensity) | Vaccine Dose Cohort |
|---|---|---|---|---|---|---|---|
| 101 | C | Autologous | 98.2% | 87.0% | 27.3% | 1811 | 5x10^6 |
|  | D | AB Plasma | 67.2% | 81.0% | 98.5% | 23712 |  |
| 102 | A | Autologous | 91.3% | 80.0% | 96.0% | 17062 | 5x10^6 |
|  | B | Autologous | 74.7% | 76.0% | 94.9% | 15401 |  |
|  | C | Autologous | 79.1% | 80.0% | 91.3% | 10574 |  |
|  | D | *Off Treatment as of 06/24/13: patient request* |  |  |  |  |  |
| 103 | B | Autologous | 99.4% | 86.0% | 10.8% | 721 | 5x10^6 |
|  | C | AB Plasma | 89.9% | 79.0% | 95.7% | 17734 |  |
| 104 | A | Autologous | 81.8% | 71.0% | 97.8% | 19481 | 5x10^6 |
|  | B | AB Plasma | 89.5% | 47.0% FAIL | 95.2% | 21106 |  |
| 105 | A | Autologous | 44.7% FAIL | 77.0% | 95.1% | 18620 | 5x10^6 |
|  | B | AB Plasma | 54.2% FAIL | 86.0% | 98.7% | 21954 |  |
| 106 | A | Autologous | 51.9% FAIL | 80.0% | 72.6% | 160 | 5x10^6 |
|  | B | AB Plasma | 71.9% | 83.0% | 90.2% | 161 |  |
| 107 | A | Autologous | 86.2% | 77.0% | 50.3% | 6054 | 5x10^6 |
|  | B | AB Plasma | 65.7% | 75.0% | 72.3% | 10293 |  |
| 201 | A | Autologous | 52.3% | 84.0% | 40.8% | 3348 | 10x10^6 |
|  | B | AB Plasma | 80.3% | 82.0% | 95.9% | 19864 |  |
| 202 | A | Autologous | 91.2% | 73.0% | 88.2% | 10564 | 10x10^6 |
|  | B | AB Plasma | 86.5% | 78.0% | 93.0% | 14241 |  |
| 203 | A | Autologous | 85.4% | 82.0% | 85.5% | 14898 | 10x10^6 |
|  | B | AB Plasma | 93.7% | 77.0% | 76.1% | 12164 |  |
| 204 | A | Autologous | 96.5% | 88.0% | 96.5% | 13706 | 10x10^6 |
|  | B | AB Plasma | 90.3% | 84.0% | 97.8% | 14704 |  |
| 205 | A | Autologous | 92.2% | 93.0% | 98.2% | 20186 | 10x10^6 |
|  | B | AB Plasma | 96.8% | 77.0% | 95.1% | 18961 |  |
| 206 | A | Autologous | 94.4% | 76.0% | 18.2% | 1122 | 10x10^6 |
|  | B | AB Plasma | 94.7% | 68.0% | 90.0% | 13998 |  |
| 207 | A | Autologous | 80.3% | 87.0% | 98.5% | 21792 | 10x10^6 |
|  | B | AB Plasma | 92.3% | 73.0% | 98.2% | 15104 |  |
| 208 | A | Autologous | 83.9% | 53.0% | 86.4% | 14490 | 10x10^6 |
|  | B | AB Plasma | 85.7% | 80.0% | 90.2% | 16029 |  |
| 301 | A | Autologous | 66.3% | 77.0% | 95.7% | 20162 | 20x10^6 |
|  | B | AB Plasma | 71.5% | 72.0% | 94.9% | 14894 |  |
| 302 | A | AB Plasma | 93.7% | 86.0% | 82.5% | 5850 | 20x10^6 |
|  | B | Autologous | 91.4% | 71.0% | 60.6% | 3213 |  |
| 303 | A | AB Plasma | 72.0% | 74.0% | 97.6% | 10204 | 20x10^6 |
|  | B | Autologous | 98.7% | 46% FAIL | 38.7% | 1517 |  |
| 304 | A | Autologous | 75.7% | 80.0% | 97.9% | 10813 | 20x10^6 |
|  | B | AB Plasma | 89.3% | 72.0% | 97.0% | 10538 |  |
| 305 | A | Autologous | 91.9% | 73.0% | 99.0% | 11082 | 20x10^6 |
|  | B | AB Plasma | 71.0% | 80.0% | 98.7% | 14403 |  |
| 306 | A | Autologous | 77.2% | 89.0% | 98.5% | Missing | 20x10^6 |
|  | B | AB Plasma | 88.0% | 84.0% | 86.6% | 5961 |  |

FIG. 8A Clinical Translation: AdHER2 DC Vaccine

Part I: Naïve to HER2-Targeted Therapies that Received at Least One Dose of Vaccine

| Dose Cohort | Vaccine Dose | Clinical Response | Response Type | Duration |
|---|---|---|---|---|
| Dose Cohort 1 N=6 | 5 x 10⁶ | NONE | N/A | 102 ALIVE @ 140 Wks |
| Dose Cohort 2 N=7 | 10 x 10⁶ | YES (3/7, 43%) | | |
| 202 IHC 3+ Gastric | | | irPR Max -70.5% @Wk 24 | 44 Weeks Clinical PD @Wk 52 |
| 204 IHC 2+ Colon | | | irSD | 28 Weeks Imaging PD @Wk 36 |
| 205 IHC 1+ Colon | | | irSD | 24 Weeks Clinical PD @Wk24 |
| Dose Cohort 3 N=6 | 20 x 10⁶ | YES (2/4, 50%) | | |
| 301 IHC 1+ Colon | | Deceased | NR-PD @Wk 12 | N/A |
| 302 IHC 3+ Ovarian | | NED @ 76 Wks | irCR | Ongoing: CTCs 0 Wk 52 |
| 303 IHC 3+ Bladder | | NED @ 76 Wks | Adjuvant Bladder Ca | Ongoing |
| 304 IHC 3+ Prostate | | Deceased | NR-PD @Wk 16 | N/A |
| 305 IHC 1+ Bladder | | NED @ 64 Wks | Adjuvant Bladder Ca | Ongoing |
| 306 IHC 1+ Ovarian | | -25% @ 36 Wks | irSD | Ongoing: CTCs 0 Wk 28 |
| Expansion Cohort N=12 | 40 x 10⁶ | | | |
| 307 IHC 2+ Cervical | | Deceased | NR-PD @ Wk 18 | N/A |
| 308 IHC 1+ Bladder | | Off-Study Esophageal Ca | N/A | N/A |
| 309 IHC 3+ Prostate | | +26% @ 8 Wks | NR-PD @ Wk 12 | N/A |

FIG. 8B

Clinical Translation: AdHER2 DC Vaccine

Part II: Breast Cancer Cohort Failed *Multiple* HER2-Targeted Therapies

| Dose Cohort | Vaccine Dose | Clinical Response | Response Type | Duration |
|---|---|---|---|---|
| Dose Cohort 1   N = 6 | 20 x 10⁶ | | | |
| 401  IHC 2+/FISH 1.1 Breast | | +14.8% @ 16 Weeks | irSD | As of Week 16 |
| 402  IHC 3+/FISH 1.2 Breast | | +20.0% @ 12 Weeks | irSD | As of Week 12 |
| 403  IHC 3+/FISH 13.7 Breast | | +68.2% @ 8 Weeks | irPD | As of Week 8 |
| 404  IHC 3+/FISH 3.6 Breast | | -15.0% @ 8 Weeks | irSD | As of Week 8 |
| 405  IHC 3+/FISH 1.7 Breast | | +43.4% @ 8 Weeks | irPD | As of Week 8 |
| Expansion Cohort  N = 24 | 40 x 10⁶ | | | |

Baseline CXCR4+EpCAM+ CTC

HER2+EpCAM+ CTC change after AdHER2/neu DC vaccine

SEQUENCE LISTING

<160> NUMBER OF SEQ ID NOS: 3

<210> SEQ ID NO 1
<211> LENGTH: 32635
<212> TYPE: DNA
<213> ORGANISM: Artificial Sequence
<220> FEATURE:
<223> OTHER INFORMATION: Synthetic polynucleotide vector
<220> FEATURE:
<221> NAME/KEY: misc_feature
<222> LOCATION: (1)..(103)
<223> OTHER INFORMATION: Inverted terminal repeat (ITR)
<220> FEATURE:
<221> NAME/KEY: misc_feature
<222> LOCATION: (683)..(1272)
<223> OTHER INFORMATION: CMV promoter
<220> FEATURE:
<221> NAME/KEY: CDS
<222> LOCATION: (1277)..(3304)
<223> OTHER INFORMATION: HER2-ECTM
<220> FEATURE:
<221> NAME/KEY: misc_feature
<222> LOCATION: (3305)..(3651)
<223> OTHER INFORMATION: BGH polyA
<220> FEATURE:
<221> NAME/KEY: CDS
<222> LOCATION: (28439)..(29470)
<223> OTHER INFORMATION: Ad5/Ad35 chimeric fiber
<220> FEATURE:
<221> NAME/KEY: misc_feature
<222> LOCATION: (32567)..(32635)
<223> OTHER INFORMATION: Inverted terminal repeat (ITR)

<400> SEQUENCE: 1

| | | | | | |
|---|---|---|---|---|---|
| catcatcaat | aatataccct | attttggatt | gaagccaata | tgataatgag | ggggtggagt | 60 |
| ttgtgacgtg | gcgcggggcg | tgggaacggg | gcgggtgacg | tagtagtgtg | gcggaagtgt | 120 |
| gatgttgcaa | gtgtggcgga | acacatgtaa | gcgacggatg | tggcaaaagt | gacgttttg | 180 |
| gtgtgcgccg | gtgtacacag | gaagtgacaa | ttttcgcgcg | gttttaggcg | gatgttgtag | 240 |
| taaatttggg | cgtaaccgag | taagatttgg | ccattttcgc | gggaaaactg | aataagagga | 300 |
| agtgaaatct | gaataatttt | gtgttactca | tagcgcgtaa | tctctagcat | cgtaactata | 360 |
| acggtcctaa | ggtagcgaaa | gctcagatct | cccgatcccc | tatggtgcac | tctcagtaca | 420 |
| atctgctctg | atgccgcata | gttaagccag | tatctgctcc | ctgcttgtgt | gttggaggtc | 480 |
| gctgagtagt | gcgcgagcaa | aatttaagct | acaacaaggc | aaggcttgac | cgacaattgc | 540 |
| atgaagaatc | tgcttagggt | taggcgtttt | gcgctgcttc | gcgatgtacg | ggccagatat | 600 |
| acgcgttgac | attgattatt | gactagttat | taatagtaat | caattacggg | gtcattagtt | 660 |
| catagcccat | atatggagtt | ccgcgttaca | taacttacgg | taaatggccc | gcctggctga | 720 |
| ccgcccaacg | acccccgccc | attgacgtca | ataatgacgt | atgttcccat | agtaacgcca | 780 |
| atagggactt | tccattgacg | tcaatgggtg | gagtatttac | ggtaaactgc | ccacttggca | 840 |
| gtacatcaag | tgtatcatat | gccaagtacg | ccccctattg | acgtcaatga | cggtaaatgg | 900 |
| cccgcctggc | attatgccca | gtacatgacc | ttatgggact | ttcctacttg | gcagtacatc | 960 |
| tacgtattag | tcatcgctat | taccatggtg | atgcggtttt | ggcagtacat | caatgggcgt | 1020 |
| ggatagcggt | ttgactcacg | gggatttcca | agtctccacc | ccattgacgt | caatgggagt | 1080 |
| ttgttttggc | accaaaatca | acgggacttt | ccaaaatgtc | gtaacaactc | cgccccattg | 1140 |
| acgcaaatgg | gcggtaggcg | tgtacggtgg | gaggtctata | taagcagagc | tctctggcta | 1200 |
| actagagaac | ccactgctta | ctggcttatc | gaaattaata | cgactcacta | tagggagacc | 1260 |
| caagctggct | agcacc atg gag ctg gcg gcc ttg tgc cgc tgg ggg ctc ctc | 1312 |

```
              Met Glu Leu Ala Ala Leu Cys Arg Trp Gly Leu Leu
                1               5                      10 ctc gcc ctc ttg ccc ccc gga gcc gcg agc acc caa gtg tgc acc ggc      1360
Leu Ala Leu Leu Pro Pro Gly Ala Ala Ser Thr Gln Val Cys Thr Gly
         15                  20                  25 aca gac atg aag ctg cgg ctc cct gcc agt ccc gag acc cac ctg gac      1408
Thr Asp Met Lys Leu Arg Leu Pro Ala Ser Pro Glu Thr His Leu Asp
         30                  35                  40 atg ctc cgc cac ctc tac cag ggc tgc cag gtg gtg cag gga aac ctg      1456
Met Leu Arg His Leu Tyr Gln Gly Cys Gln Val Val Gln Gly Asn Leu
45                  50                  55                  60 gaa ctc acc tac ctg ccc acc aat gcc agc ctg tcc ttc ctg cag gat      1504
Glu Leu Thr Tyr Leu Pro Thr Asn Ala Ser Leu Ser Phe Leu Gln Asp
                 65                  70                  75 atc cag gag gtg cag ggc tac gtg ctc atc gct cac aac caa gtg agg      1552
Ile Gln Glu Val Gln Gly Tyr Val Leu Ile Ala His Asn Gln Val Arg
             80                  85                  90 cag gtc cca ctg cag agg ctg cgg att gtg cga ggc acc cag ctc ttt      1600
Gln Val Pro Leu Gln Arg Leu Arg Ile Val Arg Gly Thr Gln Leu Phe
             95                 100                 105 gag gac aac tat gcc ctg gcc gtg cta gac aat gga gac ccg ctg aac      1648
Glu Asp Asn Tyr Ala Leu Ala Val Leu Asp Asn Gly Asp Pro Leu Asn
        110                 115                 120 aat acc acc cct gtc aca ggg gcc tcc cca gga ggc ctg cgg gag ctg      1696
Asn Thr Thr Pro Val Thr Gly Ala Ser Pro Gly Gly Leu Arg Glu Leu
125                 130                 135                 140 cag ctt cga agc ctc aca gag atc ttg aaa gga ggg gtc ttg atc cag      1744
Gln Leu Arg Ser Leu Thr Glu Ile Leu Lys Gly Gly Val Leu Ile Gln
                145                 150                 155 cgg aac ccc cag ctc tgc tac cag gac acg att ttg tgg aag gac atc      1792
Arg Asn Pro Gln Leu Cys Tyr Gln Asp Thr Ile Leu Trp Lys Asp Ile
            160                 165                 170 ttc cac aag aac aac cag ctg gct ctc aca ctg ata gac acc aac cgc      1840
Phe His Lys Asn Asn Gln Leu Ala Leu Thr Leu Ile Asp Thr Asn Arg
                175                 180                 185 tct cgg gcc tgc cac ccc tgt tct ccg atg tgt aag ggc tcc cgc tgc      1888
Ser Arg Ala Cys His Pro Cys Ser Pro Met Cys Lys Gly Ser Arg Cys
        190                 195                 200 tgg gga gag agt tct gag gat tgt cag agc ctg acg cgc act gtc tgt      1936
Trp Gly Glu Ser Ser Glu Asp Cys Gln Ser Leu Thr Arg Thr Val Cys
205                 210                 215                 220 gcc ggt ggc tgt gcc cgc tgc aag ggg cca ctg ccc act gac tgc tgc      1984
Ala Gly Gly Cys Ala Arg Cys Lys Gly Pro Leu Pro Thr Asp Cys Cys
                225                 230                 235 cat gag cag tgt gct gcc ggc tgc acg ggc ccc aag cac tct gac tgc      2032
His Glu Gln Cys Ala Ala Gly Cys Thr Gly Pro Lys His Ser Asp Cys
            240                 245                 250 ctg gcc tgc ctc cac ttc aac cac agt ggc atc tgt gag ctg cac tgc      2080
Leu Ala Cys Leu His Phe Asn His Ser Gly Ile Cys Glu Leu His Cys
        255                 260                 265 cca gcc ctg gtc acc tac aac aca gac acg ttt gag tcc atg ccc aat      2128
Pro Ala Leu Val Thr Tyr Asn Thr Asp Thr Phe Glu Ser Met Pro Asn
270                 275                 280 ccc gag ggc cgg tat aca ttc ggc gcc agc tgt gtg act gcc tgt ccc      2176
Pro Glu Gly Arg Tyr Thr Phe Gly Ala Ser Cys Val Thr Ala Cys Pro
285                 290                 295                 300 tac aac tac ctt tct acg gac gtg gga tcc tgc acc ctc gtc tgc ccc      2224
Tyr Asn Tyr Leu Ser Thr Asp Val Gly Ser Cys Thr Leu Val Cys Pro
                305                 310                 315
```

```
ctg cac aac caa gag gtg aca gca gag gat gga aca cag cgg tgt gag    2272
Leu His Asn Gln Glu Val Thr Ala Glu Asp Gly Thr Gln Arg Cys Glu
            320                 325                 330 aag tgc agc aag ccc tgt gcc cga gtg tgc tat ggt ctg ggc atg gag    2320
Lys Cys Ser Lys Pro Cys Ala Arg Val Cys Tyr Gly Leu Gly Met Glu
        335                 340                 345 cac ttg cga gag gtg agg gca gtt acc agt gcc aat atc cag gag ttt    2368
His Leu Arg Glu Val Arg Ala Val Thr Ser Ala Asn Ile Gln Glu Phe
    350                 355                 360 gct ggc tgc aag aag atc ttt ggg agc ctg gca ttt ctg ccg gag agc    2416
Ala Gly Cys Lys Lys Ile Phe Gly Ser Leu Ala Phe Leu Pro Glu Ser
365                 370                 375                 380 ttt gat ggg gac cca gcc tcc aac act gcc ccg ctc cag cca gag cag    2464
Phe Asp Gly Asp Pro Ala Ser Asn Thr Ala Pro Leu Gln Pro Glu Gln
                385                 390                 395 ctc caa gtg ttt gag act ctg gaa gag atc aca ggt tac cta tac atc    2512
Leu Gln Val Phe Glu Thr Leu Glu Glu Ile Thr Gly Tyr Leu Tyr Ile
            400                 405                 410 tca gca tgg ccg gac agc ctg cct gac ctc agc gtc ttc cag aac ctg    2560
Ser Ala Trp Pro Asp Ser Leu Pro Asp Leu Ser Val Phe Gln Asn Leu
        415                 420                 425 caa gta atc cgg gga cga att ctg cac aat ggc gcc tac tcg ctg acc    2608
Gln Val Ile Arg Gly Arg Ile Leu His Asn Gly Ala Tyr Ser Leu Thr
    430                 435                 440 ctg caa ggg ctg ggc atc agc tgg ctg ggg ctg cgc tca ctg agg gaa    2656
Leu Gln Gly Leu Gly Ile Ser Trp Leu Gly Leu Arg Ser Leu Arg Glu
445                 450                 455                 460 ctg ggc agt gga ctg gcc ctc atc cac cat aac acc cac ctc tgc ttc    2704
Leu Gly Ser Gly Leu Ala Leu Ile His His Asn Thr His Leu Cys Phe
                465                 470                 475 gtg cac acg gtg ccc tgg gac cag ctc ttt cgg aac ccg cac caa gct    2752
Val His Thr Val Pro Trp Asp Gln Leu Phe Arg Asn Pro His Gln Ala
            480                 485                 490 ctg ctc cac act gcc aac cgg cca gag gac gag tgt gtg ggc gag ggc    2800
Leu Leu His Thr Ala Asn Arg Pro Glu Asp Glu Cys Val Gly Glu Gly
        495                 500                 505 ctg gcc tgc cac cag ctg tgc gcc cga ggg cac tgc tgg ggt cca ggg    2848
Leu Ala Cys His Gln Leu Cys Ala Arg Gly His Cys Trp Gly Pro Gly
    510                 515                 520 ccc acc cag tgt gtc aac tgc agc cag ttc ctt cgg ggc cag gag tgc    2896
Pro Thr Gln Cys Val Asn Cys Ser Gln Phe Leu Arg Gly Gln Glu Cys
525                 530                 535                 540 gtg gag gaa tgc cga gta ctg cag ggg ctc ccc agg gag tat gtg aat    2944
Val Glu Glu Cys Arg Val Leu Gln Gly Leu Pro Arg Glu Tyr Val Asn
                545                 550                 555 gcc agg cac tgt ttg ccg tgc cac cct gag tgt cag ccc cag aat ggc    2992
Ala Arg His Cys Leu Pro Cys His Pro Glu Cys Gln Pro Gln Asn Gly
            560                 565                 570 tca gtg acc tgt ttt gga ccg gag gct gac cag tgt gtg gcc tgt gcc    3040
Ser Val Thr Cys Phe Gly Pro Glu Ala Asp Gln Cys Val Ala Cys Ala
        575                 580                 585 cac tat aag gac cct ccc ttc tgc gtg gcc cgc tgc ccc agc ggt gtg    3088
His Tyr Lys Asp Pro Pro Phe Cys Val Ala Arg Cys Pro Ser Gly Val
    590                 595                 600 aaa cct gac ctc tcc tac atg ccc atc tgg aag ttt cca gat gag gag    3136
Lys Pro Asp Leu Ser Tyr Met Pro Ile Trp Lys Phe Pro Asp Glu Glu
605                 610                 615                 620 ggc gca tgc cag cct tgc ccc atc aac tgc acc cac tcc tgt gtg gac    3184
Gly Ala Cys Gln Pro Cys Pro Ile Asn Cys Thr His Ser Cys Val Asp
                625                 630                 635
```

```
ctg gat gac aag ggc tgc ccc gcc gag cag aga gcc agc cct ctg acg      3232
Leu Asp Asp Lys Gly Cys Pro Ala Glu Gln Arg Ala Ser Pro Leu Thr
            640                 645                 650 tcc atc atc tct gcg gtg gtt ggc att ctg ctg gtc gtg gtc ttg ggg      3280
Ser Ile Ile Ser Ala Val Val Gly Ile Leu Leu Val Val Val Leu Gly
            655                 660                 665 gtg gtc ttt ggg atc ctc atc tag ggtaccaagc ttaagtttaa accgctgatc    3334
Val Val Phe Gly Ile Leu Ile
    670             675 agcctcgact gtgccttcta gttgccagcc atctgttgtt tgcccctccc ccgtgccttc    3394
cttgaccctg gaaggtgcca ctcccactgt cctttcctaa taaaatgagg aaattgcatc    3454
gcattgtctg agtaggtgtc attctattct ggggggtggg gtggggcagg acagcaaggg    3514
ggaggattgg gaagacaata gcaggcatgc tggggatgcg gtgggctcta tggcttctga    3574
ggcggaaaga accagcagat ctgcagatct gaattcatct atgtcgggtg cggagaaaga    3634
ggtaatgaaa tggcatcgac tcgaagatct gggcgtggtt aagggtggga agaatatat     3694 aaggtggggg tcttatgtag ttttgtatct gttttgcagc agccgccgcc gccatgagca    3754
ccaactcgtt tgatggaagc attgtgagct catatttgac aacgcgcatg cccccatggg    3814
ccggggtgcg tcagaatgtg atgggctcca gcattgatgg tcgccccgtc ctgcccgcaa    3874
actctactac cttgacctac gagaccgtgt ctggaacgcc gttggagact gcagcctccg    3934
ccgccgcttc agccgctgca gccaccgccc gcgggattgt gactgacttt gctttcctga    3994
gcccgcttgc aagcagtgca gcttcccgtt catccgcccg cgatgacaag ttgacggctc    4054
ttttggcaca attggattct ttgacccggg aacttaatgt cgtttctcag cagctgttgg    4114
atctgcgcca gcaggtttct gccctgaagg cttcctcccc tcccaatgcg gtttaaaaca    4174
taaataaaaa accagactct gtttggattt ggatcaagca agtgtcttgc tgtctttatt    4234
taggggtttt gcgcgcgcgg taggcccggg accagcggtc tcggtcgttg agggtcctgt    4294
gtattttttc caggacgtgg taaaggtgac tctggatgtt cagatacatg ggcataagcc    4354
cgtctctggg gtggaggtag caccactgca gagcttcatg ctgcggggtg gtgttgtaga    4414
tgatccagtc gtagcaggag cgctgggcgt ggtgcctaaa aatgtctttc agtagcaagc    4474
tgattgccag gggcaggccc ttggtgtaag tgtttacaaa gcggttaagc tgggatgggt    4534
gcatacgtgg ggatatgaga tgcatcttgg actgtatttt taggttggct atgttcccag    4594
ccatatccct ccggggattc atgttgtgca gaaccaccag cacagtgtat ccggtgcact    4654
tgggaaattt gtcatgtagc ttagaaggaa atgcgtggaa gaacttggag acgcccttgt    4714
gacctccaag atttccatg cattcgtcca taatgatggc aatgggccca cgggcggcgg    4774
cctgggcgaa gatatttctg ggatcactaa cgtcatagtt gtgttccagg atgagatcgt    4834
cataggccat ttttacaaag cgcgggcgga gggtgccaga ctgcggtata atggttccat    4894
ccggcccagg ggcgtagtta ccctcacaga tttgcatttc ccacgctttg agttcagatg    4954
gggggatcat gtctacctgc ggggcgatga agaaaacggt ttccggggta ggggagatca    5014
gctgggaaga aagcaggttc ctgagcagct gcgacttacc gcagccggtg ggcccgtaaa    5074
tcacacctat taccggctgc aactggtagt taagagagct gcagctgccg tcatccctga    5134 gcagggggc cacttcgtta agcatgtccc tgactcgcat gttttccctg accaaatccg      5194
ccagaaggcg ctcgccgccc agcgatagca gttcttgcaa ggaagcaaag tttttcaacg    5254
gtttgagacc gtccgccgta ggcatgcttt tgagcgtttg accaagcagt tccaggcggt    5314
```

```
cccacagctc ggtcacctgc tctacggcat ctcgatccag catatctcct cgtttcgcgg   5374
gttggggcgg ctttcgctgt acggcagtag tcggtgctcg tccagacggg ccagggtcat   5434
gtctttccac gggcgcaggg tcctcgtcag cgtagtctgg gtcacggtga aggggtgcgc   5494
tccgggctgc gcgctggcca gggtgcgctt gaggctggtc ctgctggtgc tgaagcgctg   5554
ccggtcttcg ccctgcgcgt cggccaggta gcatttgacc atggtgtcat agtccagccc   5614
ctccgcggcg tggcccttgg cgcgcagctt gcccttggag gaggcgccgc acgaggggca   5674
gtgcagactt ttgagggcgt agagcttggg cgcgagaaat accgattccg gggagtaggc   5734
atccgcgccg caggccccgc agacggtctc gcattccacg agccaggtga gctctggccg   5794
ttcggggtca aaaaccaggt ttcccccatg cttttttgatg cgtttcttac ctctggtttc   5854
catgagccgg tgtccacgct cggtgacgaa aaggctgtcc gtgtcccgt atacagactt    5914
gagaggcctg tcctcgagcg tgttccgcg gtcctcctcg tatagaaact cggaccactc    5974
tgagacaaag gctcgcgtcc aggccagcac gaaggaggct aagtgggagg gtagcggtc    6034
gttgtccact aggggtcca ctcgctccag ggtgtgaaga cacatgtcgc cctcttcggc     6094
atcaaggaag gtgattggtt tgtaggtgta ggccacgtga ccgggtgttc ctgaagggg     6154
gctataaaag ggggtggggg cgcgttcgtc ctcactctct tccgcatcgc tgtctgcgag    6214
ggccagctgt tggggtgagt actccctctg aaaagcgggc atgacttctg cgctaagatt    6274
gtcagtttcc aaaaacgagg aggatttgat attcacctgg cccgcggtga tgcctttgag   6334
ggtggccgca tccatctggt cagaaaagac aatcttttttg ttgtcaagct tggtggcaaa   6394
cgacccgtag agggcgttgg acagcaactt ggcgatggag cgcagggttt ggttttttgtc  6454
gcgatcggcg cgctccttgg ccgcgatgtt tagctgcacg tattcgcgcg caacgcaccg    6514
ccattcggga aagacggtgg tgcgctcgtc gggcaccagg tgcacgcgcc aaccgcggtt    6574
gtgcagggtg acaaggtcaa cgctggtggc tacctctccg cgtaggcgct cgttggtcca    6634
gcagaggcgg ccgcccttgc gcgagcagaa tggcggtagg gggtctagct gcgtctcgtc    6694
cggggggtct gcgtccacgg taaagacccc gggcagcagg cgcgcgtcga agtagtctat    6754
cttgcatcct tgcaagtcta gcgcctgctg ccatgcgcgg gcggcaagcg cgcgctcgta    6814
tgggttgagt gggggacccc atggcatggg gtgggtgagc gcggaggcgt acatgccgca    6874
aatgtcgtaa acgtagaggg gctctctgag tattccaaga tatgtagggt agcatcttcc    6934
accgcggatg ctggcgcgca cgtaatcgta tagttcgtgc gagggagcga ggaggtcggg    6994
accgaggttg ctacgggcgg gctgctctgc tcggaagact atctgcctga agatggcatg    7054
tgagttggat gatatggttg gacgctggaa gacgttgaag ctggcgtctg tgagacctac    7114
cgcgtcacgc acgaaggagg cgtaggagtc gcgcagcttg ttgaccagct cggcggtgac    7174
ctgcacgtct agggcgcagt agtccagggt ttccttgatg atgtcatact tatcctgtcc    7234
cttttttttc cacagctcgc ggttgaggac aaactcttcg cggtctttcc agtactcttg    7294
gatcggaaac ccgtcggcct ccgaacggta agagcctagc atgtagaact ggttgacggc    7354
ctggtaggcg cagcatccct tttctacggg tagcgcgtat gcctgcgcgg ccttccggag    7414
cgaggtgtgg gtgagcgcaa aggtgtccct gaccatgact tgaggtact ggtatttgaa     7474
gtcagtgtcg tcgcatccgc cctgctccca gagcaaaaag tccgtgcgct ttttggaacg    7534
cggatttggc agggcgaagg tgacatcgtt gaagagtatc tttcccgcgc gaggcataaa    7594
gttgcgtgtg atgcggaagg gtcccggcac ctcggaacgg ttgttaatta cctgggcggc    7654
gagcacgatc tcgtcaaagc cgttgatgtt gtggcccaca atgtaaagtt ccaagaagcg    7714
```

-continued

```
cgggatgccc ttgatggaag gcaattttttt aagttcctcg taggtgagct cttcagggga   7774
gctgagcccg tgctctgaaa gggcccagtc tgcaagatga gggttggaag cgacgaatga   7834
gctccacagg tcacgggcca ttagcatttg caggtggtcg cgaaaggtcc taaactggcg   7894
acctatggcc attttttctg gggtgatgca gtagaaggta agcgggtctt gttcccagcg   7954
gtcccatcca aggttcgcgg ctaggtctcg cgcggcagtc actagaggct catctccgcc   8014
gaacttcatg accagcatga agggcacgag ctgcttccca aaggccccca tccaagtata   8074
ggtctctaca tcgtaggtga caaagagacg ctcggtgcga ggatgcgagc cgatcgggaa   8134
gaactggatc tcccgccacc aattggagga gtggctattg atgtggtgaa agtagaagtc   8194
cctgcgacgg gccgaacact cgtgctggct tttgtaaaaa cgtgcgcagt actggcagcg   8254
gtgcacgggc tgtacatcct gcacgaggtt gacctgacga ccgcgcacaa ggaagcagag   8314
tgggaatttg agcccctcgc ctggcgggtt tggctggtgg tcttctactt cggctgcttg   8374
tccttgaccg tctggctgct cgaggggagt tacggtggat cggaccacca cgccgcgcga   8434
gcccaaagtc cagatgtccg cgcgcggcgg tcggagcttg atgacaacat cgcgcagatg   8494
ggagctgtcc atggtctgga gctcccgcgg cgtcaggtca ggcgggagct cctgcaggtt   8554
tacctcgcat agacgggtca gggcgcgggc tagatccagg tgatacctaa tttccagggg   8614
ctggttggtg gcgcgtcga tggcttgcaa gaggccgcat ccccgcggcg cgactacgt   8674
accgcgcggc gggcggtggg ccgcgggggt gtccttggat gatgcatcta aaagcggtga   8734
cgcgggcgag cccccggagg tagggggggc tccggacccg ccgggagagg gggcaggggc   8794
acgtcggcgc cgcgcgcggg caggagctgg tgctgcgcgc gtaggttgct ggcgaacgcg   8854
acgacgcggc ggttgatctc ctgaatctgg cgcctctgcg tgaagacgac gggcccggtg   8914
agcttgaacc tgaaagagag ttcgacagaa tcaatttcgg tgtcgttgac ggcggcctgg   8974
cgcaaaatct cctgcacgtc tcctgagttg tcttgatagg cgatctcggc catgaactgc   9034
tcgatctctt cctcctggag atctccgcgt ccggctcgct ccacggtggc ggcgaggtcg   9094
ttggaaatgc gggccatgag ctgcgagaag gcgttgaggc ctccctcgtt ccagacgcgg   9154
ctgtagacca cgcccccttc ggcatcgcgg gcgcgcatga ccacctgcgc gagattgagc   9214
tccacgtgcc gggcgaagac ggcgtagttt cgcaggcgct gaaagaggta gttgagggtg   9274
gtggcggtgt gttctgccac gaagaagtac ataacccagc gtcgcaacgt ggattcgttg   9334
atatccccca aggcctcaag gcgctccatg gcctcgtaga agtccacggc gaagttgaaa   9394
aactgggagt tgcgcgccga cacgttaac tcctcctcca gaagacggat gagctcggcg   9454
acagtgtcgc gcacctcgcg ctcaaaggct acaggggcct cttcttcttc ttcaatctcc   9514
tcttccataa gggcctcccc ttcttcttct tctggcggcg tgggggagg ggggacacgg   9574
cggcgacgac ggcgcaccgg gaggcggtcg acaaagcgct cgatcatctc cccgcggcga   9634
cggcgcatgg tctcggtgac ggcgcggccg ttctcgcggg ggcgcagttg gaagacgccg   9694
cccgtcatgt cccggttatg ggttggcggg gggctgccat gcggcaggga tacggcgcta   9754
acgatgcatc tcaacaattg ttgtgtaggt actccgccgc cgagggacct gagcgagtcc   9814
gcatcgaccg gatcggaaaa cctctcgaga aaggcgtcta accagtcaca gtcgcaaggt   9874
aggctgagca ccgtggcggg cggcagcggg cggcggtcgg ggttgtttct ggcggaggtg   9934
ctgctgatga tgtaattaaa gtaggcggtc ttgagacggc ggatggtcga cagaagcacc   9994
atgtccttgg gtccggcctg ctgaatgcgc aggcggtcgg ccatgcccca ggcttcgttt  10054
```

```
tgacatcggc gcaggtctttt gtagtagtct tgcatgagcc tttctaccgg cacttcttct    10114
tctccttcct cttgtcctgc atctcttgca tctatcgctg cggcggcggc ggagtttggc    10174
cgtaggtggc gccctcttcc tcccatgcgt gtgaccccga agcccctcat cggctgaagc    10234
agggctaggt cggcgacaac gcgctcggct aatatggcct gctgcacctg cgtgagggta    10294
gactggaagt catccatgtc cacaaagcgg tggtatgcgc ccgtgttgat ggtgtaagtg    10354
cagttggcca taacggacca gttaacggtc tggtgacccg gctgcgagag ctcggtgtac    10414
ctgagacgcg agtaagccct cgagtcaaat acgtagtcgt tgcaagtccg caccaggtac    10474
tggtatccca ccaaaaagtg cggcggcggc tggcggtaga ggggccagcg tagggtggcc    10534
ggggctccgg gggcgagatc ttccaacata aggcgatgat atccgtagat gtacctggac    10594
atccaggtga tgccggcggc ggtggtggag gcgcgcggaa agtcgcggac gcggttccag    10654
atgttgcgca gcggcaaaaa gtgctccatg gtcgggacgc tctggccggt caggcgcgcg    10714
caatcgttga cgctctagcg tgcaaaagga gagcctgtaa gcgggcactc ttccgtggtc    10774
tggtggataa attcgcaagg gtatcatggc ggacgaccgg ggttcgagcc ccgtatccgg    10834
ccgtccgccg tgatccatgc ggttaccgcc cgcgtgtcga acccaggtgt gcgacgtcag    10894
acaacggggg agtgctcctt ttggcttcct tccaggcgcg gcggctgctg cgctagcttt    10954
tttggccact ggccgcgcgc agcgtaagcg gttaggctgg aaagcgaaag cattaagtgg    11014
ctcgctccct gtagccggag ggttatttc caagggttga gtcgcgggac ccccggttcg    11074
agtctcggac cggccggact gcggcgaacg ggggtttgcc tccccgtcat gcaagacccc    11134
gcttgcaaat tcctccggaa acagggacga gccccttttt tgcttttccc agatgcatcc    11194
ggtgctgcgg cagatgcgcc cccctcctca gcagcggcaa gagcaagagc agcggcagac    11254
atgcagggca ccctcccctc ctcctaccgc gtcaggaggg gcgacatccg cggttgacgc    11314
ggcagcagat ggtgattacg aaccccgcg gcgccgggcc cggcactacc tggacttgga    11374
ggagggcgag ggcctggcgc ggctaggagc gccctctcct gagcggcacc caagggtgca    11434
gctgaagcgt gatacgcgtg aggcgtacgt gccgcggcag aacctgtttc gcgaccgcga    11494
gggagaggag cccgaggaga tgcgggatcg aaagttccac gcagggcgcg agctgcggca    11554
tggcctgaat cgcgagcggt tgctgcgcga ggaggacttt gagcccgacg cgcgaaccgg    11614
gattagtccc gcgcgcgcac acgtggcggc cgccgacctg gtaaccgcat acgagcagac    11674
ggtgaaccag gagattaact ttcaaaaaag ctttaacaac cacgtgcgta cgcttgtggc    11734
gcgcgaggag gtggctatag gactgatgca tctgtgggac tttgtaagcg cgctggagca    11794
aaacccaaat agcaagccgc tcatggcgca gctgttcctt atagtgcagc acagcaggga    11854
caacgaggca ttcagggatg cgctgctaaa catagtagag cccgagggcc gctggctgct    11914
cgatttgata aacatcctgc agagcatagt ggtgcaggag cgcagcttga gcctggctga    11974
caaggtggcc gccatcaact attccatgct tagcctgggc aagttttacg cccgcaagat    12034
ataccatacc ccttacgttc ccatagacaa ggaggtaaag atcgagggt tctacatgcg    12094
catggcgctg aaggtgctta ccttgagcga cgacctgggc gtttatcgca cgagcgcat    12154
ccacaaggcc gtgagcgtga gccggcgcg cgagctcagc gaccgcgagc tgatgcacag    12214
cctgcaaagg gccctggctg gcacgggcag cggcgataga gaggccgagt cctactttga    12274
cgcgggcgct gacctgcgct gggcccaag ccgacgcgcc ctggaggcag ctggggccgg    12334
acctgggctg gcggtggcac ccgcgcgcgc tggcaacgtc ggcggcgtgg aggaatatga    12394
cgaggacgat gagtacgagc cagaggacgg cgagtactaa gcggtgatgt ttctgatcag    12454
```

-continued

```
atgatgcaag acgcaacgga cccggcggtg cgggcggcgc tgcagagcca gccgtccggc    12514
cttaactcca cggacgactg cgccaggtc atggaccgca tcatgtcgct gactgcgcgc    12574
aatcctgacg cgttccggca gcagccgcag gccaaccggc tctccgcaat tctggaagcg    12634
gtggtcccgg cgcgcgcaaa ccccacgcac gagaaggtgc tggcgatcgt aaacgcgctg    12694
gccgaaaaca gggccatccg gcccgacgag gccggcctgg tctacgacgc gctgcttcag    12754
cgcgtggctc gttacaacag cggcaacgtg cagaccaacc tggaccggct ggtgggggat    12814
gtgcgcgagg ccgtggcgca gcgtgagcgc gcgcagcagc agggcaacct gggctccatg    12874
gttgcactaa acgccttcct gagtacacag cccgccaacg tgccgcgggg acaggaggac    12934
tacaccaact ttgtgagcgc actgcggcta atggtgactg agacaccgca aagtgaggtg    12994
taccagtctg ggccagacta ttttttccag accagtagac aaggcctgca gaccgtaaac    13054
ctgagccagg ctttcaaaaa cttgcagggg ctgtgggggg tgcgggctcc cacaggcgac    13114
cgcgcgaccg tgtctagctt gctgacgccc aactcgcgcc tgttgctgct gctaatagcg    13174 ccccttcacgg acagtggcag cgtgtcccgg gacacatacc taggtcactt gctgacactg    13234
taccgcgagg ccataggtca ggcgcatgtg gacgagcata ctttccagga gattacaagt    13294
gtcagccgcg cgctggggca ggaggacacg ggcagcctgg aggcaaccct aaactacctg    13354
ctgaccaacc ggcggcagaa gatcccctcg ttgcacagtt taaacagcga ggaggagcgc    13414
attttgcgct acgtgcagca gagcgtgagc cttaacctga tgcgcgacgg ggtaacgccc    13474
agcgtggcgc tggacatgac cgcgcgcaac atggaaccgg gcatgtatgc ctcaaaccgg    13534
ccgtttatca accgcctaat ggactacttg catcgcgcgg ccgccgtgaa ccccgagtat    13594
ttcaccaatg ccatcttgaa cccgcactgg ctaccgcccc ctggtttcta caccggggga    13654
ttcgaggtgc ccgagggtaa cgatggattc ctctgggacg acatagacga cagcgtgttt    13714 tcccccgcaac cgcagaccct gctagagttg caacagcgcg agcaggcaga ggcggcgctg    13774
cgaaaggaaa gcttccgcag gccaagcagc ttgtccgatc taggcgctgc ggccccgcgg    13834
tcagatgcta gtagcccatt tccaagcttg atagggtctc ttaccagcac tcgcaccacc    13894
cgcccgcgcc tgctgggcga ggaggagtac ctaaacaact cgctgctgca gccgcagcgc    13954
gaaaaaaacc tgcctccggc atttcccaac aacgggatag agagcctagt ggacaagatg    14014
agtagatgga agacgtacgc gcaggagcac agggacgtgc caggcccgcg cccgcccacc    14074
cgtcgtcaaa ggcacgaccg tcagcggggt ctggtgtggg aggacgatga ctcggcagac    14134
gacagcagcg tcctggattt gggagggagt ggcaacccgt tgcgcaccct tcgccccagg    14194 ctgggggagaa tgttttaaaa aaaaaaagc atgatgcaaa ataaaaaact caccaaggcc    14254
atggcaccga gcgttggttt tcttgtattc cccttagtat gcggcgcgcg gcgatgtatg    14314
aggaaggtcc tcctccctcc tacgagagtg tggtgagcgc ggcgccagtg gcggcggcgc    14374
tgggttctcc cttcgatgct cccctggacc cgccgtttgt gcctccgcgg tacctgcggc    14434
ctaccggggg gagaaacagc atccgttact ctgagttggc acccctattc gacaccaccc    14494
gtgtgtacct ggtggacaac aagtcaacgg atgtggcatc cctgaactac cagaacgacc    14554
acagcaactt tctgaccacg gtcattcaaa acaatgacta cagcccgggg gaggcaagca    14614
cacagaccat caatcttgac gaccggtcgc actgggcgg cgacctgaaa accatcctgc    14674
ataccaacat gccaaatgtg aacgagttca tgtttaccaa taagtttaag gcgcgggtga    14734
tggtgtcgcg cttgcctact aaggacaatc aggtggagct gaaatacgag tgggtggagt    14794
```

```
tcacgctgcc cgagggcaac tactccgaga ccatgaccat agaccttatg aacaacgcga   14854
tcgtggagca ctacttgaaa gtgggcagac agaacgggt tctggaaagc gacatcgggg    14914
taaagtttga cacccgcaac ttcagactgg ggtttgaccc cgtcactggt cttgtcatgc   14974
ctggggtata tacaaacgaa gccttccatc cagacatcat tttgctgcca ggatgcgggg   15034
tggacttcac ccacagccgc ctgagcaact tgttgggcat ccgcaagcgg caacccttcc   15094
aggagggctt taggatcacc tacgatgatc tggaggtgg taacattccc gcactgttgg    15154
atgtggacgc ctaccaggcg agcttgaaag atgacaccga acagggcggg ggtggcgcag   15214
gcggcagcaa cagcagtggc agcggcgcgg aagagaactc caacgcggca gccgcggcaa   15274
tgcagccggt ggaggacatg aacgatcatg ccattcgcgg cgacaccttt gccacacggg   15334
ctgaggagaa gcgcgctgag gccgaagcag cggccgaagc tgccgccccc gctgcgcaac   15394
ccgaggtcga gaagcctcag aagaaaccgg tgatcaaacc cctgacagag gacagcaaga   15454
aacgcagtta caacctaata agcaatgaca gcaccttcac ccagtaccgc agctggtacc   15514
ttgcatacaa ctacggcgac cctcagaccg gaatccgctc atggaccctg ctttgcactc   15574
ctgacgtaac ctgcggctcg gagcaggtct actggtcgtt gccagacatg atgcaagacc   15634
ccgtgacctt ccgctccacg cgccagatca gcaactttcc ggtggtgggc gccgagctgt   15694
tgcccgtgca ctccaagagc ttctacaacg accaggccgt ctactcccaa ctcatccgcc   15754
agtttacctc tctgacccac gtgttcaatc gctttcccga gaaccagatt ttggcgcgcc   15814
cgccagcccc caccatcacc accgtcagtg aaaacgttcc tgctctcaca gatcacggga   15874
cgctaccgct cgcaacagc atcggaggag tccagcgagt gaccattact gacgccagac    15934
gccgcacctg cccctacgtt tacaaggccc tgggcatagt ctcgccgcgc gtcctatcga   15994
gccgcacttt tgagcaagc atgtccatcc ttatatcgcc cagcaataac acaggctggg    16054
gcctgcgctt cccaagcaag atgtttggcg gggccaagaa gcgctccgac caacacccag   16114
tgcgcgtgcg cgggcactac cgcgcgccct ggggcgcgca caacgcggc cgcactgggc    16174 gcaccaccgt cgatgacgcc atcgacgcgg tggtggagga ggcgcgcaac tacacgccca   16234
cgccgccacc agtgtccaca gtggacgcgg ccattcagac cgtggtgcgc ggagcccggc   16294
gctatgctaa aatgaagaga cggcggaggc gcgtagcacg tcgccaccgc cgccgacccg   16354
gcactgccgc ccaacgcgcg gcggcggccc tgcttaaccg cgcacgtcgc accgccgac   16414 gggcggccat gcgggccgct cgaaggctgg ccgcgggtat tgtcactgtg ccccccaggt   16474
ccaggcgacg agcggccgcc gcagcagccg cggccattag tgctatgact cagggtcgca   16534
ggggcaacgt gtattgggtg cgcgactcgg ttagcggcct gcgcgtgccc gtgcgcaccc   16594 gcccccccgcg caactagatt gcaagaaaaa actacttaga ctcgtactgt tgtatgtatc   16654
cagcggcggc ggcgcgcaac gaagctatgt ccaagcgcaa aatcaaagaa gagatgctcc   16714
aggtcatcgc gccggagatc tatgccccc cgaagaagga agagcaggat tacaagcccc    16774
gaaagctaaa gcgggtcaaa aagaaaaaga aagatgatga tgatgaactt gacgacgagg   16834
tggaactgct gcacgctacc gcgcccaggc gacgggtaca gtggaaaggt cgacgcgtaa   16894
aacgtgtttt gcgaccccggc accaccgtag tctttacgcc cggtgagcgc tccacccgca   16954
cctacaagcg cgtgtatgat gaggtgtacg gcgacgagga cctgcttgag caggccaacg   17014
agcgcctcgg ggagtttgcc tacggaaagc ggcataagga catgctggcg ttgccgctgg   17074
acgagggcaa cccaacacct agcctaaagc ccgtaacact gcagcaggtg ctgcccgcgc   17134
ttgcaccgtc cgaagaaaag cgcggcctaa agcgcgagtc tggtgacttg gcacccaccg   17194
```

```
tgcagctgat ggtacccaag cgccagcgac tggaagatgt cttggaaaaa atgaccgtgg    17254
aacctgggct ggagcccgag gtccgcgtgc ggccaatcaa gcaggtggcg ccgggactgg    17314
gcgtgcagac cgtggacgtt cagatacccc ctaccagtag caccagtatt gccaccgcca    17374
cagagggcat ggagacacaa acgtcccccgg ttgcctcagc ggtggcggat gccgcggtgc   17434
aggcggtcgc tgcggccgcg tccaagacct ctacggaggt gcaaacggac ccgtggatgt    17494
ttcgcgtttc agccccccgg cgcccgcgcc gttcgaggaa gtacggcgcc gccagcgcgc    17554
tactgcccga atatgcccta catccttcca ttgcgcctac ccccggctat cgtggctaca    17614
cctaccgccc cagaagacga gcaactaccc gacgccgaac caccactgga acccgccgcc    17674
gccgtcgccg tcgccagccc gtgctggccc cgatttccgt gcgcagggtg gctcgcgaag    17734
gaggcaggac cctggtgctg ccaacagcgc gctaccaccc cagcatcgtt taaaagccgg    17794
tctttgtggt tcttgcagat atggccctca cctgccgcct ccgtttcccg gtgccgggat    17854
tccgaggaag aatgcaccgt aggagggggca tggccggcca cggcctgacg ggcggcatgc   17914
gtcgtgcgca ccaccggcgg cggcgcgcgt cgcaccgtcg catgcgcggc ggtatcctgc    17974
ccctccttat tccactgatc gccgcggcga ttggcgccgt gcccggaatt gcatccgtgg    18034
ccttgcaggc gcagagacac tgattaaaaa caagttgcat gtggaaaaat caaaataaaa    18094
agtctggact ctcacgctcg cttggtcctg taactatttt gtagaatgga agacatcaac    18154
tttgcgtctc tggccccgcg acacggctcg cgcccgttca tgggaaactg caagatatc    18214 ggcaccagca atatgagcgg tggcgccttc agctgggggct cgctgtggag cggcattaaa    18274
aatttcggtt ccaccgttaa gaactatggc agcaaggcct ggaacagcag cacaggccag    18334
atgctgaggg ataagttgaa agagcaaaat ttccaacaaa aggtggtaga tggcctggcc    18394
tctggcatta gcggggtggt ggacctggcc aaccaggcag tgcaaaataa gattaacagt    18454
aagcttgatc cccgccctcc cgtagaggag cctccaccgg ccgtggagac agtgtctcca    18514 gagggggcgtg gcgaaaagcg tccgcgcccc gacagggaag aaactctggt gacgcaaata    18574
gacgagcctc cctcgtacga ggaggcacta aagcaaggcc tgcccaccac ccgtcccatc    18634
gcgcccatgg ctaccggagt gctgggccag cacacacccg taacgctgga cctgcctccc    18694
cccgccgaca cccagcagaa acctgtgctg ccaggcccga ccgccgttgt tgtaacccgt    18754
cctagccgcg cgtccctgcg ccgcgccgcc agcggtccgc gatcgttgcg gcccgtagcc    18814
agtggcaact ggcaaagcac actgaacagc atcgtgggtc tgggggtgca atccctgaag    18874
cgccgacgat gcttctgata gctaacgtgt cgtatgtgtg tcatgtatgc gtccatgtcg    18934
ccgccagagg agctgctgag ccgccgcgcg cccgctttcc aagatggcta ccccttcgat    18994
gatgccgcag tggtcttaca tgcacatctc gggccaggac gcctcggagt acctgagccc    19054
cgggctggtg cagtttgccc gcgccaccga gacgtacttc agcctgaata caagtttag    19114 aaaccccacg gtggcgccta cgcacgacgt gaccacagac cggtcccagc gtttgacgct    19174
gcggttcatc cctgtggacc gtgaggatac tgcgtactcg tacaaggcgc ggttcaccct    19234
agctgtgggt gataaccgtg tgctggacat ggcttccacg tactttgaca tccgcggcgt    19294
gctggacagg ggccctactt ttaagcccta ctctggcact gcctacaacg ccctggctcc    19354
caagggtgcc ccaaatcctt gcgaatggga tgaagctgct actgctcttg aaataaacct    19414
agaagaagag gacgatgaca acgaagacga agtagacgag caagctgagc agcaaaaaac    19474
tcacgtattt gggcaggcgc cttattctgg tataaatatt acaaggagg gtattcaaat    19534
```

```
aggtgtcgaa ggtcaaacac ctaaatatgc cgataaaaca tttcaacctg aacctcaaat   19594
aggagaatct cagtggtacg aaacagaaat taatcatgca gctgggagag tcctaaaaaa   19654
gactacccca atgaaaccat gttacggttc atatgcaaaa cccacaaatg aaaatggagg   19714
gcaaggcatt cttgtaaagc aacaaaatgg aaagctagaa agtcaagtgg aaatgcaatt   19774
tttctcaact actgaggcag ccgcaggcaa tggtgataac ttgactccta aagtggtatt   19834
gtacagtgaa gatgtagata tagaaacccc agacactcat atttcttaca tgcccactat   19894
taaggaaggt aactcacgag aactaatggg ccaacaatct atgcccaaca ggcctaatta   19954
cattgctttt agggacaatt ttattggtct aatgtattac aacagcacgg gtaatatggg   20014
tgttctggcg ggccaagcat cgcagttgaa tgctgttgta gatttgcaag acagaaacac   20074
agagctttca taccagcttt tgcttgattc cattggtgat agaaccaggt acttttctat   20134
gtggaatcag gctgttgaca gctatgatcc agatgttaga attattgaaa atcatggaac   20194
tgaagatgaa cttccaaatt actgctttcc actgggaggt gtgattaata cagagactct   20254
taccaaggta aaacctaaaa caggtcagga aaatggatgg gaaaaagatg ctacagaatt   20314
ttcagataaa aatgaaataa gagttggaaa taattttgcc atggaaatca atctaaatgc   20374
caacctgtgg agaaatttcc tgtactccaa catagcgctg tatttgcccg acaagctaaa   20434
gtacagtcct tccaacgtaa aaatttctga taacccaaac acctacgact acatgaacaa   20494
gcgagtggtg gctcccgggc tagtggactg ctacattaac cttggagcac gctggtccct   20554
tgactatatg gacaacgtca acccatttaa ccaccaccgc aatgctggcc tgcgctaccg   20614
ctcaatgttg ctgggcaatg gtcgctatgt gcccttccac atccaggtgc tcagaagtt   20674 cttttgccatt aaaaacctcc ttctcctgcc gggctcatac acctacgagt ggaacttcag   20734
gaaggatgtt aacatggttc tgcagagctc cctaggaaat gacctaaggg ttgacggagc   20794
cagcattaag tttgatagca tttgccttta cgccaccttc ttccccatgg cccacaacac   20854
cgcctccacg cttgaggcca tgcttagaaa cgacaccaac gaccagtcct taacgacta   20914 tctctccgcc gccaacatgc tctaccctat acccgccaac gctaccaacg tgcccatatc   20974
catcccctcc cgcaactggg cggctttccg cggctgggcc ttcacgcgcc ttaagactaa   21034
ggaaacccca tcactgggct cgggctacga cccttattac acctactctg gctctatacc   21094
ctacctagat ggaacctttt acctcaacca caccttaag aaggtggcca ttacctttga   21154
ctcttctgtc agctggcctg gcaatgaccg cctgcttacc cccaacgagt ttgaaattaa   21214
gcgctcagtt gacggggagg gttacaacgt tgcccagtgt aacatgacca agactggtt   21274 cctggtacaa atgctagcta actataacat tggctaccag ggcttctata tcccagagag   21334
ctacaaggac cgcatgtact ccttctttag aaacttccag cccatgagcc gtcaggtggt   21394
ggatgatact aaatacaagg actaccaaca ggtgggcatc ctacaccaac acaacaactc   21454
tggatttgtt ggctacctg ccccccaccat gcgcgaagga caggcctacc ctgctaactt   21514
cccctatccg cttataggca agaccgcagt tgacagcatt acccagaaaa gtttctttg   21574 cgatcgcacc ctttggcgca tcccattctc cagtaacttt atgtccatgg gcgcactcac   21634
agacctgggc caaaaccttc tctacgccaa ctccgcccac gcgctagaca tgactttga   21694 ggtggatccc atgacgagc ccaccttct ttatgtttg tttgaagtct tgacgtggt   21754 ccgtgtgcac cagccgcacc gcggcgtcat cgaaaccgtg tacctgcgca cgcccttctc   21814
ggccggcaac gccacaacat aaagaagcaa gcaaatcaa caacagctgc cgccatgggc   21874
tccagtgagc aggaactgaa agccattgtc aaagatcttg gttgtgggcc atattttttg   21934
```

```
ggcacctatg acaagcgctt tccaggcttt gtttctccac acaagctcgc ctgcgccata  21994
gtcaatacgg ccggtcgcga gactgggggc gtacactgga tggcctttgc ctggaacccg  22054
cactcaaaaa catgctacct ctttgagccc tttggctttt ctgaccagcg actcaagcag  22114
gtttaccagt ttgagtacga gtcactcctg cgccgtagcg ccattgcttc ttcccccgac  22174
cgctgtataa cgctggaaaa gtccacccaa agcgtacagg ggcccaactc ggccgcctgt  22234
ggactattct gctgcatgtt tctccacgcc tttgccaact ggcccaaaac tcccatggat  22294
cacaacccca ccatgaacct tattaccggg gtacccaact ccatgctcaa cagtccccag  22354
gtacagccca ccctgcgtcg caaccaggaa cagctctaca gcttcctgga gcgccactcg  22414
ccctacttcc gcagccacag tgcgcagatt aggagcgcca cttctttttg tcacttgaaa  22474
aacatgtaaa aataatgtac tagagacact ttcaataaag gcaaatgctt ttatttgtac  22534
actctcgggt gattatttac ccccacccct gccgtctgcg ccgtttaaaa atcaaagggg  22594
ttctgccgcg catcgctatg cgccactggc agggacacgt tgcgatactg gtgtttagtg  22654
ctccacttaa actcaggcac aaccatccgc ggcagctcgg tgaagttttc actccacagg  22714
ctgcgcacca tcaccaacgc gtttagcagg tcgggcgccg atatcttgaa gtcgcagttg  22774
gggcctccgc cctgcgcgcg cgagttgcga tacacagggt tgcagcactg gaacactatc  22834
agcgccgggt ggtgcacgct ggccagcacg ctcttgtcgg agatcagatc cgcgtccagg  22894
tcctccgcgt tgctcagggc gaacggagtc aactttggta gctgccttcc caaaaagggc  22954
gcgtgcccag gctttgagtt gcactcgcac cgtagtggca tcaaaaggtg accgtgcccg  23014
gtctgggcgt taggatacag cgcctgcata aaagccttga tctgcttaaa agccacctga  23074
gcctttgcgc cttcagagaa gaacatgccg caagacttgc cggaaaactg attggcggaa  23134
caggccgcgt cgtgcacgca gcaccttgcg tcggtgttgg agatctgcac cacatttcgg  23194
ccccaccggt tcttcacgat cttggccttg ctagactgct ccttcagcgc gcgctgcccg  23254
tttttcgctcg tcacatccat ttcaatcacg tgctccttat ttatcataat gcttccgtgt  23314
agacacttaa gctcgccttc gatctcagcg cagcggtgca gccacaacgc gcagcccgtg  23374
ggctcgtgat gcttgtaggt cacctctgca aacgactgca ggtacgcctg caggaatcgc  23434
cccatcatcg tcacaaaggt cttgttgctg gtgaaggtca gctgcaaccc gcggtgctcc  23494
tcgttcagcc aggtcttgca tacggccgcc agagcttcca cttggtcagg cagtagtttg  23554
aagttcgcct ttagatcgtt atccacgtgg tacttgtcca tcagcgcgcg cgcagcctcc  23614
atgcccttct cccacgcaga cacgatcggc acactcagcg ggttcatcac cgtaatttca  23674
ctttccgctt cgctgggctc ttcctcttcc tcttgcgtcc gcataccacg cgccactggg  23734
tcgtcttcat tcagccgccg cactgtgcgc ttacctcctt tgccatgctt gattagcacc  23794
ggtgggttgc tgaaacccac catttgtagc gccacatctt ctctttcttc ctcgctgtcc  23854
acgattacct ctggtgatgg cgggcgctcg ggcttgggag aagggcgctt cttttcttc   23914
ttgggcgcaa tggccaaatc cgccgccgag gtcgatggcc gcgggctggg tgtgcgcggc  23974
accagcgcgt cttgtgatga gtcttcctcg tcctcggact cgatacgccg cctcatccgc  24034
ttttttgggg gcgcccgggg aggcggcggc gacgggacgg ggacgacac gtcctccatg   24094
gttggggac gtcgcgccgc accgcgtccg cgctcggggg tggtttcgcg ctgctcctct   24154
tcccgactgg ccatttcctt ctcctatagg cagaaaaaga tcatgcagtc agtcgagaag  24214
aaggacagcc taaccgcccc ctctgagttc gccaccaccg cctccaccga tgccgccaac  24274
```

```
gcgcctacca cctccccgt cgaggcaccc ccgcttgagg aggaggaagt gattatcgag    24334
caggacccag gttttgtaag cgaagacgac gaggaccgct cagtaccaac agaggataaa    24394
aagcaagacc aggacaacgc agaggcaaac gaggaacaag tcgggcgggg ggacgaaagg    24454
catggcgact acctagatgt gggagacgac gtgctgttga agcatctgca gcgccagtgc    24514
gccattatct gcgacgcgtt gcaagagcgc agcgatgtgc ccctcgccat agcggatgtc    24574
agccttgcct acgaacgcca cctattctca ccgcgcgtac cccccaaacg ccaagaaaac    24634
ggcacatgcg agcccaaccc gcgcctcaac ttctaccccg tatttgccgt gccagaggtg    24694
cttgccacct atcacatctt tttccaaaac tgcaagatac ccctatcctg ccgtgccaac    24754
cgcagccgag cggacaagca gctggccttg cggcagggcg ctgtcatacc tgatatcgcc    24814
tcgctcaacg aagtgccaaa aatctttgag ggtcttggac gcgacgagaa gcgcgcggca    24874
aacgctctgc aacaggaaaa cagcgaaaat gaaagtcact ctggagtgtt ggtggaactc    24934
gagggtgaca acgcgcgcct agccgtacta aaacgcagca tcgaggtcac ccactttgcc    24994
tacccggcac ttaacctacc ccccaaggtc atgagcacac tcatgagtga gctgatcgtg    25054
cgccgtgcgc agcccctgga gagggatgca aatttgcaag aacaaacaga ggagggccta    25114
cccgcagttg gcgacgagca gctagcgcgc tggcttcaaa cgcgcgagcc tgccgacttg    25174
gaggagcgac gcaaactaat gatggccgca gtgctcgtta ccgtggagct tgagtgcatg    25234
cagcggttct ttgctgaccc ggagatgcag cgcaagctag aggaaacatt gcactacacc    25294
tttcgacagg gctacgtacg ccaggcctgc aagatctcca acgtggagct ctgcaacctg    25354
gtctcctacc ttggaatttt gcacgaaaac cgccttgggc aaaacgtgct tcattccacg    25414
ctcaagggcg aggcgcgccg cgactacgtc cgcgactgcg tttacttatt tctatgctac    25474
acctggcaga cggccatggg cgtttggcag cagtgcttgg aggagtgcaa cctcaaggag    25534
ctgcagaaac tgctaaagca aaacttgaag gacctatgga cggccttcaa cgagcgctcc    25594
gtggccgcgc acctggcgga catcattttc cccgaacgcc tgcttaaaac cctgcaacag    25654
ggtctgccag acttcaccag tcaaagcatg ttgcagaact ttaggaactt tatcctagag    25714
cgctcaggaa tcttgcccgc cacctgctgt gcacttccta gcgactttgt gcccattaag    25774
taccgcgaat gccctccgcc gctttgggc cactgctacc ttctgcagct agccaactac    25834
cttgcctacc actctgacat aatggaagac gtgagcggtg acggtctact ggagtgtcac    25894
tgtcgctgca acctatgcac cccgcaccgc tccctggttt gcaattcgca gctgcttaac    25954
gaaagtcaaa ttatcggtac ctttgagctg cagggtccct cgcctgacga aaagtccgcg    26014
gctccggggt tgaaactcac tccggggctg tggacgtcgg cttaccttcg caaatttgta    26074
cctgaggact accacgccca cgagattagg ttctacgaag accaatcccg cccgcctaat    26134
gcggagctta ccgcctgcgt cattacccag ggccacattc ttggccaatt gcaagccatc    26194
aacaaagccc gccaagagtt tctgctacga aagggacggg gggtttactt ggaccccag    26254
tccggcgagg agctcaaccc aatcccccg ccgcgcagc cctatcagca gcagccgcgg    26314
gcccttgctt cccaggatgg cacccaaaaa gaagctgcag ctgccgccgc cacccacgga    26374
cgaggaggaa tactgggaca gtcaggcaga ggaggttttg gacgaggagg aggaggacat    26434
gatggaagac tgggagagcc tagacgagga agcttccgag gtcgaagagg tgtcagacga    26494
aacaccgtca ccctcggtcg cattcccctc gccggcgccc cagaaatcgg caaccggttc    26554
cagcatggct acaacctccg ctcctcaggc gccgccggca ctgcccgttc gccgaccaa    26614
ccgtagatgg gacaccactg gaaccagggc cggtaagtcc aagcagccgc cgccgttagc    26674
```

-continued

```
ccaagagcaa caacagcgcc aaggctaccg ctcatggcgc gggcacaaga acgccatagt    26734
tgcttgcttg caagactgtg ggggcaacat ctccttcgcc cgccgctttc ttctctacca    26794
tcacggcgtg gccttccccc gtaacatcct gcattactac cgtcatctct acagcccata    26854
ctgcaccggc ggcagcggca gcaacagcag cggccacaca gaagcaaagg cgaccggata    26914
gcaagactct gacaaagccc aagaaatcca cagcggcggc agcagcagga ggaggagcgc    26974
tgcgtctggc gcccaacgaa cccgtatcga cccgcgagct tagaaacagg attttccca    27034
ctctgtatgc tatatttcaa cagagcaggg gccaagaaca agagctgaaa ataaaaaaca    27094
ggtctctgcg atccctcacc cgcagctgcc tgtatcacaa aagcgaagat cagcttcggc    27154
gcacgctgga agacgcggag gctctcttca gtaaatactg cgcgctgact cttaaggact    27214
agtttcgcgc cctttctcaa atttaagcgc gaaaactacg tcatctccag cggccacacc    27274
cggcgccagc acctgttgtc agcgccatta tgagcaagga aattcccacg ccctacatgt    27334
ggagttacca gccacaaatg ggacttgcgg ctggagctgc caagactac tcaacccgaa     27394
taaactacat gagcgcggga ccccacatga tatcccgggt caacggaata cgcgcccacc    27454
gaaaccgaat tctcctggaa caggcggcta ttaccaccac acctcgtaat aaccttaatc    27514
cccgtagttg gcccgctgcc ctggtgtacc aggaaagtcc cgctcccacc actgtggtac    27574
ttcccagaga cgcccaggcc gaagttcaga tgactaactc aggggcgcag cttgcgggcg    27634
gctttcgtca cagggtgcgg tcgcccgggc agggtataac tcacctgaca atcagagggc    27694
gaggtattca gctcaacgac gagtcggtga gctcctcgct tggtctccgt ccggacggga    27754
catttcagat cggcggcgcc ggccgctctt cattcacgcc tcgtcaggca atcctaactc    27814
tgcagacctc gtcctctgag ccgcgctctg gaggcattgg aactctgcaa tttattgagg    27874
agtttgtgcc atcggtctac tttaacccct tctcgggacc tcccggccac tatccggatc    27934
aatttattcc taactttgac gcggtaaagg actcggcgga cggctacgac tgaatgttaa    27994
gtggagaggc agagcaactg cgcctgaaac acctggtcca ctgtcgccgc cacaagtgct    28054
ttgcccgcga ctccggtgag ttttgctact ttgaattgcc cgaggatcat atcgagggcc    28114
cggcgcacgg cgtccggctt accgcccagg gagagcttgc ccgtagcctg attcgggagt    28174
ttacccagcg cccctgcta gttgagcggg acaggggacc ctgtgttctc actgtgattt      28234
gcaactgtcc taaccctgga ttacatcaag atcctctagt taatggatcc attaactaat    28294
aaaaaaat aataaagcat cacttactta aaatcagtta gcaaattct gtccagttta       28354
ttcagcagca cctccttgcc ctcctcccag ctctggtatt gcagcttcct cctgctgca    28414
aactttctcc acaatctaaa tgga atg tca gtt tcc tcc tgt tcc tgt cca      28465
                          Met Ser Val Ser Ser Cys Ser Cys Pro
                                                  680 tcc gca ccc act atc ttc atg ttg ttg cag atg aag cgc gca aga ccg      28513
Ser Ala Pro Thr Ile Phe Met Leu Leu Gln Met Lys Arg Ala Arg Pro
685                 690                 695                 700 tct gaa gat acc ttc aac ccc gtg tat cca tat gac acg gaa acc ggt      28561
Ser Glu Asp Thr Phe Asn Pro Val Tyr Pro Tyr Asp Thr Glu Thr Gly
            705                 710                 715 cct cca act gtg cct ttt ctt act cct ccc ttt gta tcc ccc aat ggg      28609
Pro Pro Thr Val Pro Phe Leu Thr Pro Pro Phe Val Ser Pro Asn Gly
        720                 725                 730 ttt caa gag agt ccc cct gga gtt ctt act tta aaa tgt tta acc cca      28657
Phe Gln Glu Ser Pro Pro Gly Val Leu Thr Leu Lys Cys Leu Thr Pro
    735                 740                 745
```

| | | | | | | | | | | | | | | | |
|---|---|---|---|---|---|---|---|---|---|---|---|---|---|---|---|
| cta | aca | acc | aca | ggc | gga | tct | cta | cag | cta | aaa | gtg | gga | ggg | gga | ctt | 28705
| Leu | Thr | Thr | Thr | Gly | Gly | Ser | Leu | Gln | Leu | Lys | Val | Gly | Gly | Gly | Leu |
| | 750 | | | | | 755 | | | | 760 | | | | | |

| | | | | | | | | | | | | | | | |
|---|---|---|---|---|---|---|---|---|---|---|---|---|---|---|---|
| aca | gtg | gat | gac | act | gat | ggt | acc | tta | caa | gaa | aac | ata | cgt | gct | aca | 28753
| Thr | Val | Asp | Asp | Thr | Asp | Gly | Thr | Leu | Gln | Glu | Asn | Ile | Arg | Ala | Thr |
| 765 | | | | | 770 | | | | | 775 | | | | | 780 |

| | | | | | | | | | | | | | | | |
|---|---|---|---|---|---|---|---|---|---|---|---|---|---|---|---|
| gca | ccc | att | act | aaa | aat | aat | cac | tct | gta | gaa | cta | tcc | att | gga | aat | 28801
| Ala | Pro | Ile | Thr | Lys | Asn | Asn | His | Ser | Val | Glu | Leu | Ser | Ile | Gly | Asn |
| | | | | 785 | | | | | 790 | | | | | 795 | |

| | | | | | | | | | | | | | | | |
|---|---|---|---|---|---|---|---|---|---|---|---|---|---|---|---|
| gga | tta | gaa | act | caa | aac | aat | aaa | cta | tgt | gcc | aaa | ttg | gga | aat | ggg | 28849
| Gly | Leu | Glu | Thr | Gln | Asn | Asn | Lys | Leu | Cys | Ala | Lys | Leu | Gly | Asn | Gly |
| | | | 800 | | | | | 805 | | | | | 810 | | |

| | | | | | | | | | | | | | | | |
|---|---|---|---|---|---|---|---|---|---|---|---|---|---|---|---|
| tta | aaa | ttt | aac | aac | ggt | gac | att | tgt | ata | aag | gat | agt | att | aac | acc | 28897
| Leu | Lys | Phe | Asn | Asn | Gly | Asp | Ile | Cys | Ile | Lys | Asp | Ser | Ile | Asn | Thr |
| | | | 815 | | | | | 820 | | | | | 825 | | |

| | | | | | | | | | | | | | | | |
|---|---|---|---|---|---|---|---|---|---|---|---|---|---|---|---|
| tta | tgg | act | gga | ata | aac | cct | cca | cct | aac | tgt | caa | att | gtg | gaa | aac | 28945
| Leu | Trp | Thr | Gly | Ile | Asn | Pro | Pro | Pro | Asn | Cys | Gln | Ile | Val | Glu | Asn |
| | 830 | | | | | 835 | | | | | 840 | | | | |

| | | | | | | | | | | | | | | | |
|---|---|---|---|---|---|---|---|---|---|---|---|---|---|---|---|
| act | aat | aca | aat | gat | ggc | aaa | ctt | act | tta | gta | tta | gta | aaa | aac | gga | 28993
| Thr | Asn | Thr | Asn | Asp | Gly | Lys | Leu | Thr | Leu | Val | Leu | Val | Lys | Asn | Gly |
| 845 | | | | | 850 | | | | | 855 | | | | | 860 |

| | | | | | | | | | | | | | | | |
|---|---|---|---|---|---|---|---|---|---|---|---|---|---|---|---|
| ggg | ctt | gtt | aat | ggc | tac | gtg | tct | cta | gtt | ggt | gta | tca | gac | act | gtg | 29041
| Gly | Leu | Val | Asn | Gly | Tyr | Val | Ser | Leu | Val | Gly | Val | Ser | Asp | Thr | Val |
| | | | | 865 | | | | | 870 | | | | | 875 | |

| | | | | | | | | | | | | | | | |
|---|---|---|---|---|---|---|---|---|---|---|---|---|---|---|---|
| aac | caa | atg | ttc | aca | caa | aag | aca | gca | aac | atc | caa | tta | aga | tta | tat | 29089
| Asn | Gln | Met | Phe | Thr | Gln | Lys | Thr | Ala | Asn | Ile | Gln | Leu | Arg | Leu | Tyr |
| | | | 880 | | | | | 885 | | | | | 890 | | |

| | | | | | | | | | | | | | | | |
|---|---|---|---|---|---|---|---|---|---|---|---|---|---|---|---|
| ttt | gac | tct | tct | gga | aat | cta | tta | act | gat | gaa | tca | gac | tta | aaa | att | 29137
| Phe | Asp | Ser | Ser | Gly | Asn | Leu | Leu | Thr | Asp | Glu | Ser | Asp | Leu | Lys | Ile |
| | | | 895 | | | | | 900 | | | | | 905 | | |

| | | | | | | | | | | | | | | | |
|---|---|---|---|---|---|---|---|---|---|---|---|---|---|---|---|
| cca | ctt | aaa | aat | aaa | tct | tct | aca | gcg | acc | agt | gaa | act | gta | gcc | agc | 29185
| Pro | Leu | Lys | Asn | Lys | Ser | Ser | Thr | Ala | Thr | Ser | Glu | Thr | Val | Ala | Ser |
| | 910 | | | | | 915 | | | | | 920 | | | | |

| | | | | | | | | | | | | | | | |
|---|---|---|---|---|---|---|---|---|---|---|---|---|---|---|---|
| agc | aaa | gcc | ttt | atg | cca | agt | act | aca | gct | tat | ccc | ttc | aac | acc | act | 29233
| Ser | Lys | Ala | Phe | Met | Pro | Ser | Thr | Thr | Ala | Tyr | Pro | Phe | Asn | Thr | Thr |
| 925 | | | | | 930 | | | | | 935 | | | | | 940 |

| | | | | | | | | | | | | | | | |
|---|---|---|---|---|---|---|---|---|---|---|---|---|---|---|---|
| act | agg | gat | agt | gaa | aac | tac | att | cat | gga | ata | tgt | tac | tac | atg | act | 29281
| Thr | Arg | Asp | Ser | Glu | Asn | Tyr | Ile | His | Gly | Ile | Cys | Tyr | Tyr | Met | Thr |
| | | | | 945 | | | | | 950 | | | | | 955 | |

| | | | | | | | | | | | | | | | |
|---|---|---|---|---|---|---|---|---|---|---|---|---|---|---|---|
| agt | tat | gat | aga | agt | cta | ttt | ccc | ttg | aac | att | tct | ata | atg | cta | aac | 29329
| Ser | Tyr | Asp | Arg | Ser | Leu | Phe | Pro | Leu | Asn | Ile | Ser | Ile | Met | Leu | Asn |
| | | | 960 | | | | | 965 | | | | | 970 | | |

| | | | | | | | | | | | | | | | |
|---|---|---|---|---|---|---|---|---|---|---|---|---|---|---|---|
| agc | cgt | atg | att | tct | tcc | aat | gtt | gcc | tat | gcc | ata | caa | ttt | gaa | tgg | 29377
| Ser | Arg | Met | Ile | Ser | Ser | Asn | Val | Ala | Tyr | Ala | Ile | Gln | Phe | Glu | Trp |
| | | 975 | | | | | 980 | | | | | 985 | | | |

| | | | | | | | | | | | | | | | |
|---|---|---|---|---|---|---|---|---|---|---|---|---|---|---|---|
| aat | cta | aat | gca | agt | gaa | tct | cca | gaa | agc | aac | ata | | gct | acg | ctg | acc | 29425
| Asn | Leu | Asn | Ala | Ser | Glu | Ser | Pro | Glu | Ser | Asn | Ile | Ala | Thr | Leu | Thr |
| | 990 | | | | | 995 | | | | | 1000 | | | | |

| | | | | | | | | | | | | |
|---|---|---|---|---|---|---|---|---|---|---|---|---|
| aca | tcc | ccc | ttt | ttc | ttt | tct | tac | att | aca | gaa | gac | gac | aac | taa | 29470
| Thr | Ser | Pro | Phe | Phe | Phe | Ser | Tyr | Ile | Thr | Glu | Asp | Asp | Asn | |
| 1005 | | | | | 1010 | | | | | 1015 | | | aatgccaag aataaagaat cgtttgtgtt atgtttcaac gtgtttatt ttcaattgca 29530 gaaaatttca gtcattttt cattcagtag tatagcccca ccaccacata gcttatacag 29590 atcaccgtac cttaatcaaa ctcacagaac cctagtattc aacctgccac ctccctccca 29650 acacacagag tacacagtcc tttctccccg gctggcctta aaaagcatca tatcatgggt 29710 aacagacata ttcttaggtg ttatattcca cacggtttcc tgtcgagcca aacgctcatc 29770 agtgatatta ataaactccc cgggcagctc acttaagttc atgtcgctgt ccagctgctg 29830

```
agccacaggc tgctgtccaa cttgcggttg cttaacgggc ggcgaaggag aagtccacgc    29890
ctacatgggg gtagagtcat aatcgtgcat caggataggg cggtggtgct gcagcagcgc    29950
gcgaataaac tgctgccgcc gccgctccgt cctgcaggaa tacaacatgg cagtggtctc    30010
ctcagcgatg attcgcaccg cccgcagcat aaggcgcctt gtcctccggg cacagcagcg    30070
caccctgatc tcacttaaat cagcacagta actgcagcac agcaccacaa tattgttcaa    30130
aatcccacag tgcaaggcgc tgtatccaaa gctcatggcg gggaccacag aacccacgtg    30190
gccatcatac cacaagcgca ggtagattaa gtggcgaccc ctcataaaca cgctggacat    30250
aaacattacc tcttttggca tgttgtaatt caccacctcc cggtaccata taaacctctg    30310
attaaacatg gcgccatcca ccaccatcct aaaccagctg gccaaaacct gcccgccggc    30370
tatacactgc agggaaccgg gactggaaca atgacagtgg agagcccagg actcgtaacc    30430
atggatcatc atgctcgtca tgatatcaat gttggcacaa cacaggcaca cgtgcataca    30490
cttcctcagg attacaagct cctcccgcgt tagaaccata tcccagggaa caacccattc    30550
ctgaatcagc gtaaatccca cactgcaggg aagacctcgc acgtaactca cgttgtgcat    30610
tgtcaaagtg ttacattcgg gcagcagcgg atgatcctcc agtatggtag cgcgggtttc    30670
tgtctcaaaa ggaggtagac gatccctact gtacggagtg cgccgagaca accgagatcg    30730
tgttggtcgt agtgtcatgc caaatggaac gccggacgta gtcatatttc ctgaagcaaa    30790
accaggtgcg ggcgtgacaa acagatctgc gtctccggtc tcgccgctta gatcgctctg    30850
tgtagtagtt gtagtatatc cactctctca aagcatccag gcgcccctg gcttcgggtt    30910 ctatgtaaac tccttcatgc gccgctgccc tgataacatc caccaccgca gaataagcca    30970
cacccagcca acctacacat tcgttctgcg agtcacacac gggaggagcg ggaagagctg    31030
gaagaaccat gttttttttt ttattccaaa agattatcca aaacctcaaa atgaagatct    31090
attaagtgaa cgcgctcccc tccggtggcg tggtcaaact ctacagccaa agaacagata    31150
atggcatttg taagatgttg cacaatggct tccaaaaggc aaacggccct cacgtccaag    31210
tggacgtaaa ggctaaaccc ttcagggtga atctcctcta taaacattcc agcaccttca    31270
accatgccca ataattctc atctcgccac cttctcaata tatctctaag caaatcccga    31330
atattaagtc cggccattgt aaaaatctgc tccagagcgc cctccacctt cagcctcaag    31390
cagcgaatca tgattgcaaa aattcaggtt cctcacagac ctgtataaga ttcaaaagcg    31450
gaacattaac aaaaataccg cgatcccgta ggtcccttcg cagggccagc tgaacataat    31510
cgtgcaggtc tgcacggacc agcgcggcca cttccccgcc aggaaccatg acaaaagaac    31570
ccacactgat tatgacacgc atactcggag ctatgctaac cagcgtagcc ccgatgtaag    31630
cttgttgcat gggcggcgat ataaaatgca aggtgctgct caaaaaatca ggcaaagcct    31690
cgcgcaaaaa agaaagcaca tcgtagtcat gctcatgcag ataaaggcag gtaagctccg    31750
gaaccaccac agaaaagac accattttc tctcaaacat gtctgcgggt ttctgcataa    31810
acacaaaata aaataacaaa aaaacattta aacattagaa gcctgtctta caacaggaaa    31870 aacaacccctt ataagcataa gacggactac ggccatgccg gcgtgaccgt aaaaaaactg    31930
gtcaccgtga ttaaaaagca ccaccgacag ctcctcggtc atgtccggag tcataatgta    31990
agactcggta aacacatcag gttgattcac atcggtcagt gctaaaaagc gaccgaaata    32050
gcccggggga atacatacccc gcaggcgtag agacaacatt acagccccca taggaggtat    32110
aacaaaatta ataggagaga aaaacacata aacacctgaa aaaccctcct gcctaggcaa    32170
```

```
aatagcaccc tcccgctcca gaacaacata cagcgcttcc acagcggcag ccataacagt   32230
cagccttacc agtaaaaaag aaaacctatt aaaaaaacac cactcgacac ggcaccagct   32290
caatcagtca cagtgtaaaa aagggccaag tgcagagcga gtatatatag gactaaaaaa   32350
tgacgtaacg gttaaagtcc acaaaaaaca cccagaaaac cgcacgcgaa cctacgccca   32410
gaaacgaaag ccaaaaaacc cacaacttcc tcaaatcgtc acttccgttt tcccacgtta   32470
cgtcacttcc cattttaaga aaactacaat tcccaacaca tacaagttac tccgccctaa   32530
aacctacgtc acccgccccg ttcccacgcc ccgcgccacg tcacaaactc cacccccctca   32590 ttatcatatt ggcttcaatc caaaataagg tatattattg atgat               32635
```

<210> SEQ ID NO 2
<211> LENGTH: 675
<212> TYPE: PRT
<213> ORGANISM: Artificial Sequence
<220> FEATURE:
<223> OTHER INFORMATION: Synthetic Construct

<400> SEQUENCE: 2

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285
```

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
                355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
                435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
                515                 520                 525

Val Asn Cys Ser Gln Phe Leu Arg Gly Gln Glu Cys Val Glu Glu Cys
                530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
                610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile
675

<210> SEQ ID NO 3
<211> LENGTH: 343

<212> TYPE: PRT
<213> ORGANISM: Artificial Sequence
<220> FEATURE:
<223> OTHER INFORMATION: Synthetic Construct

<400> SEQUENCE: 3

```
Met Ser Val Ser Ser Cys Ser Cys Pro Ser Ala Pro Thr Ile Phe Met
1               5                   10                  15

Leu Leu Gln Met Lys Arg Ala Arg Pro Ser Glu Asp Thr Phe Asn Pro
                20                  25                  30

Val Tyr Pro Tyr Asp Thr Glu Thr Gly Pro Pro Thr Val Pro Phe Leu
            35                  40                  45

Thr Pro Pro Phe Val Ser Pro Asn Gly Phe Gln Glu Ser Pro Pro Gly
        50                  55                  60

Val Leu Thr Leu Lys Cys Leu Thr Pro Leu Thr Thr Thr Gly Gly Ser
65                  70                  75                  80

Leu Gln Leu Lys Val Gly Gly Leu Thr Val Asp Asp Thr Asp Gly
                85                  90                  95

Thr Leu Gln Glu Asn Ile Arg Ala Thr Ala Pro Ile Thr Lys Asn Asn
                100                 105                 110

His Ser Val Glu Leu Ser Ile Gly Asn Gly Leu Glu Thr Gln Asn Asn
                115                 120                 125

Lys Leu Cys Ala Lys Leu Gly Asn Gly Leu Lys Phe Asn Asn Gly Asp
                130                 135                 140

Ile Cys Ile Lys Asp Ser Ile Asn Thr Leu Trp Thr Gly Ile Asn Pro
145                 150                 155                 160

Pro Pro Asn Cys Gln Ile Val Glu Asn Thr Asn Thr Asn Asp Gly Lys
                165                 170                 175

Leu Thr Leu Val Leu Val Lys Asn Gly Gly Leu Val Asn Gly Tyr Val
                180                 185                 190

Ser Leu Val Gly Val Ser Asp Thr Val Asn Gln Met Phe Thr Gln Lys
                195                 200                 205

Thr Ala Asn Ile Gln Leu Arg Leu Tyr Phe Asp Ser Ser Gly Asn Leu
                210                 215                 220

Leu Thr Asp Glu Ser Asp Leu Lys Ile Pro Leu Lys Asn Lys Ser Ser
225                 230                 235                 240

Thr Ala Thr Ser Glu Thr Val Ala Ser Ser Lys Ala Phe Met Pro Ser
                245                 250                 255

Thr Thr Ala Tyr Pro Phe Asn Thr Thr Thr Arg Asp Ser Glu Asn Tyr
                260                 265                 270

Ile His Gly Ile Cys Tyr Tyr Met Thr Ser Tyr Asp Arg Ser Leu Phe
                275                 280                 285

Pro Leu Asn Ile Ser Ile Met Leu Asn Ser Arg Met Ile Ser Ser Asn
                290                 295                 300

Val Ala Tyr Ala Ile Gln Phe Glu Trp Asn Leu Asn Ala Ser Glu Ser
305                 310                 315                 320

Pro Glu Ser Asn Ile Ala Thr Leu Thr Thr Ser Pro Phe Phe Phe Ser
                325                 330                 335

Tyr Ile Thr Glu Asp Asp Asn
                340
```

COMPOSITIONS AND METHODS FOR THE TREATMENT OF HER2-EXPRESSING SOLID TUMORS

CROSS REFERENCE TO RELATED APPLICATIONS

This application is the U.S. National Stage of International Application No. PCT/US2016/059680, filed Oct. 31, 2016, published in English under PCT Article 21(2), which claims the benefit of U.S. Provisional Application No. 62/248,964, filed Oct. 30, 2015, which is herein incorporated by reference in its entirety.

FIELD

This disclosure concerns a recombinant adenovirus expressing the extracellular (EC) and transmembrane (TM) domains of HER2, and its use for the treatment of HER2-positive cancer.

BACKGROUND

The HER2 receptor tyrosine kinase is a member of the epidermal growth factor receptor (EGFR) family of transmembrane receptors. HER2 (also known as EGFR2, ERBB2 or neu) is over-expressed in breast and many other types of cancers (Slamon et al., *Science* 244:707-712, 1989). Over-expression of Her2 has been implicated in the aggressive growth and poor clinical outcome associated with HER2-positive breast tumors (Slamon et al., *Science* 235:177-182, 1987).

The HER2 protein has three domains—extracellular (EC), transmembrane (TM) and intracellular (IC)—and sends signals to tumor cells to promote their growth and inhibit cell death. Tumors that over-express HER2 are associated with more aggressive disease, higher recurrence rates and reduced survival rates. The FDA-approved anti-cancer agents trastuzumab (Herceptin™), pertuzumab (PERJETA™) and adotrastuzumab emtansine (KADCYLA™) are monoclonal antibodies that each recognize one of two distinct, small portions of the extracellular domain of the HER2 protein. Although these monoclonal antibodies have to be given repeatedly to have an effect, they have been shown to improve survival and reduce or slow disease progression in patients with HER2 expressing breast, gastric and gastroesophageal junction tumors.

Despite their effectiveness in some cancers, trastuzumab, pertuzumab and ado-trastuzumab emtansine do not work for everyone and even when they are effective, they may stop working after a period of time. These monoclonal antibodies must be administered continuously every three weeks to have a beneficial treatment effect, which comes with significant inconvenience and cost to the patient In addition, trastuzumab has been associated with decreased heart function (cardiac toxicity) in 3-7% of patients who receive it as a single agent, increasing to approximately 27% when it is given in combination with some types of chemotherapy.

SUMMARY

Disclosed herein is a recombinant adenovirus type 5 vector that encodes the EC and TM domains of the human HER2 protein (HER2ECTM) and an adenovirus type 35 fiber protein. Also disclosed is a recombinant adenovirus expressing HER2ECTM and an Ad35 fiber protein (referred to herein as "Ad5f35HER2ECTM," "AdHER2ECTM" or "AdHER2"), as well as isolated dendritic cells transduced with the HER2ECTM expressing recombinant adenovirus (referred to herein as "Ad5f35HER2ECTM DC," AdHER2ECTM DC" or "AdHER2 DC"). Expression of the Ad35 fiber protein significantly increases the capacity of the recombinant adenovirus to infect dendritic cells and other hematopoietic cells. Compositions comprising the recombinant HER2ECTM expressing adenovirus or dendritic cells transduced with the recombinant HER2ECTM expressing adenovirus can be used to elicit a HER2-specific immune response in a subject, such as a subject with a HER2-positive tumor.

Provided herein is a recombinant adenovirus vector encoding the EC and TM domains of human HER2 and an Ad35 fiber protein. In some embodiments, the nucleotide sequence of the vector comprises, consists essentially of, or consists of SEQ ID NO: 1 (e.g., the Ad5f35HER2ECTM vector). Also provided is a recombinant adenovirus produced by transforming isolated cells with the recombinant adenovirus vector. Compositions comprising isolated dendritic cells transduced with the recombinant adenovirus are further provided. In some examples, the composition further includes one or more of AB allogeneic plasma, a pharmaceutically acceptable carrier and an adjuvant.

Also provided herein are compositions comprising isolated dendritic cells transduced with a recombinant Ad5 expressing the EC and TM domains of human HER2 and an Ad35 fiber protein; and AB allogeneic plasma. In some embodiments, the compositions further include a pharmaceutically acceptable carrier, an adjuvant, or both.

Further provided is a method of eliciting a HER2-specific immune response in a subject, and a method of treating a HER2-positive cancer in a subject, by administering a composition that includes isolated dendritic cells transduced with a recombinant HER2ECTM expressing adenovirus disclosed herein. In some embodiments, the dendritic cells are autologous dendritic cells obtained from the subject. In some examples, the HER2-positive cancer is a breast, ovarian, cervical, colorectal, prostate, renal cell, bladder, gastroesophageal, non-small cell lung cancer, an ependymoma or a sarcoma.

Also provided is a method of treating a HER2-positive cancer in a subject that includes preparing autologous dendritic cells by culturing monocytes obtained from the subject in culture medium comprising AB allogeneic plasma; transducing the autologous dendritic cells with a recombinant Ad5 expressing the EC and TM domains of human HER2 and an Ad35 fiber protein; and administering to the subject a composition comprising the autologous dendritic cells transduced with the recombinant adenovirus in a pharmaceutically acceptable carrier. In some embodiments, the composition further includes an adjuvant. In some examples, the HER2-positive cancer is a breast, ovarian, cervical, colorectal, prostate, renal cell, bladder, gastroesophageal or non-small cell lung cancer, an ependymoma or a sarcoma.

In some embodiments of the methods provided herein, the subject receives additional therapy, such as radiation, chemotherapy, administration of other an anti-cancer immunotherapies (for example checkpoint inhibitors targeting CTLA-4, PD-1, PD-L1, TGFβ), oncolytic virus therapy or other tumor antigen or vector-based therapeutic vaccines.

The foregoing and other objects, features, and advantages of the invention will become more apparent from the following detailed description, which proceeds with reference to the accompanying figures.

BRIEF DESCRIPTION OF THE DRAWINGS

FIG. 3 is a schematic outlining pre-clinical tests of dendritic cell transfection and maturation conditions. Dendritic cell viability and product yield for each condition are shown in FIGS. 4A and 4B.

FIG. 6 is a schematic of the AdHER2ECTM DC Phase I clinical trial design. In this study, two cohorts of patients are treated sequentially (Part I and Part II). Patients in Part I have any level of HER2 expression and are naïve to previous HER2-directed therapy, such as trastuzumab. Subjects in Part II are breast cancer patients with 3+ levels of HER2 expression who have failed trastuzumab or a similar therapy.

FIG. 7 is a table showing the percentage of autologous dendritic cells expressing HER2 (CD340) when cultured in autologous plasma compared to the percentage of autologous dendritic cells expressing HER2 when cultured in AB allogeneic plasma.

FIGS. 8A-8B are tables summarizing clinical data for Dose Cohorts 1, 2 and 3, and the Expansion Cohort. Results from patients enrolled in Part I (FIG. 8A) and Part II (FIG. 8B) show evidence of clinical benefit and anti-tumor activity. NED=no evidence of disease; PD=progressive disease; NR=no response; irPR=immune-related partial response; irSD=immune-related stable disease; irCR=immune-related complete response.

SEQUENCE LISTING

Figure 1A:
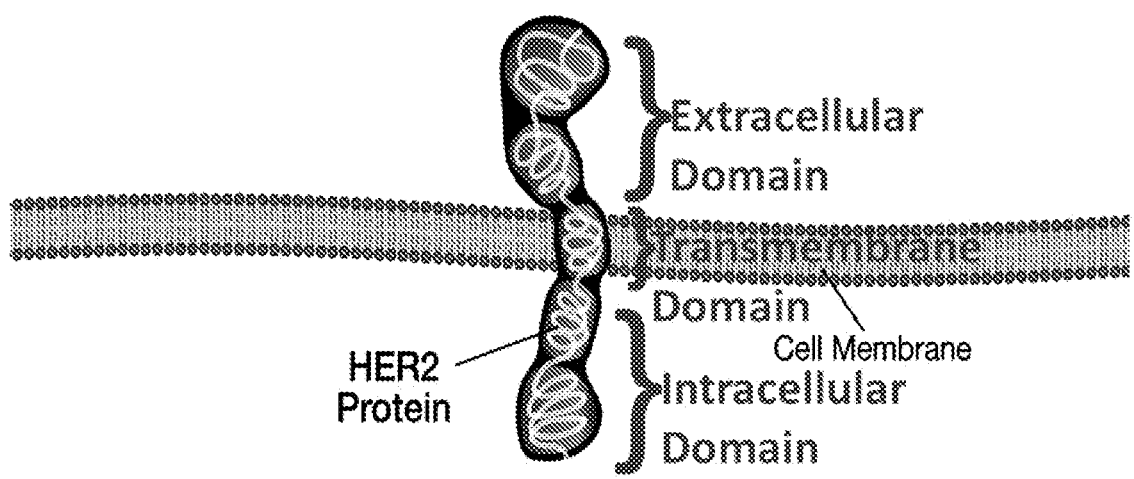
FIGS. 1A-1C show schematics of the human HER2 protein. The HER2 protein contains extracellular (EC), transmembrane (TM) and intracellular (IC) domains (FIG. 1A). Current therapeutic antibodies that target the HER2 protein, including trastuzumab (Herceptin™), pertuzumab (PERJETA™) and adotrastuzumab emtansine (KADCYLA™), bind to a single epitope of the HER2 EC domain and must be administered repeated to have a therapeutic effect (FIG. 1B). The AdHER2ECTM dendritic cell vaccine disclosed herein is designed to induce a patient's own immune system to produce a polyclonal anti-HER2 antibody response, thereby producing antibodies that collectively bind to multiple epitopes throughout the HER2 protein (FIG. 1C).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Apr. 17, 2018, 61.7 KB, which is incorporated by reference herein. In the accompanying sequence listing:

SEQ ID NO: 1 is the nucleotide sequence of the Ad5f35HER2ECTM vector with the following features:
Nucleotides 1-103-5' inverted terminal repeat (ITR)
Nucleotides 683-1272—CMV promoter
Nucleotides 1277-3304—human HER2ECTM coding sequence
Nucleotides 3305-3651—BGH polyA
Nucleotides 28439-29470—Ad5/Ad35 chimeric fiber coding sequence
Nucleotides 32567-32635-3' ITR SEQ ID NO: 2 is the amino acid sequence of human HER2ECTM.

SEQ ID NO: 3 is the amino acid sequence of an Ad5/Ad35 chimeric fiber protein having an Ad5 tail domain and Ad35 shaft and knob domains.

DETAILED DESCRIPTION

I. Abbreviations

APC antigen presenting cell
CRC colorectal cancer
CT computerized tomography
CTC circulating tumor cell
CTLA-4 cytotoxic T lymphocyte-associated protein 4
DC dendritic cell
DLT dose-limiting toxicity
EC extracellular
EGFR epidermal growth factor receptor
EpCAM epithelial cell adhesion molecule
FISH fluorescence in situ hybridization
HI heat inactivated
IC intracellular
iDC immature dendritic cell
IFN interferon
IHC immunohistochemistry
IL interleukin
iCR immune-related complete response
irPD immune-related progressive disease
irPR immune-related partial response
irRC immune-related response criteria
irSD immune-related stable disease
ITR inverted terminal repeat
IV intravenous
KLH keyhole limpet hemocyanin
LAG-3 lymphocyte activation gene 3
LPS lipopolysaccharide
LVEF left ventricular ejection fraction
MAb monoclonal antibody
mDC mature dendritic cell
MFI mean fluorescence intensity
MHC major histocompatibility complex
MOI multiplicity of infection
MTD maximum tolerated dose
NED no evidence of disease
NR no response
NSCLC non-small cell lung carcinoma
ORR overall response rate
OS overall survival
PD progressive disease
PD-1 programmed cell death protein 1

PD-L1 programmed death ligand 1
PFS progression free survival
SAE severe adverse event
TAA tumor-associated antigen
TGF transforming growth factor
TIM-3 T cell immunoglobulin and mucin domain 3
TM transmembrane
TTP time to progression
VP Virus particle I. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.). *The Encyclopedia of Molecular Biology*, published by Blackwell Science Ltd., 1994 (ISBN 0-632-02182-9); and Robert A. Meyers (ed.). *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adenovirus: A non-enveloped virus with a liner, double-stranded DNA genome and an icosahedral capsid. There are currently 68 known serotypes of human adenovirus, which are divided into seven species (species A, B, C, D, E, F and G). Different serotypes of adenovirus are associated with different cell tropism and different types of disease, with some serotypes causing respiratory disease (primarily species B and C), conjunctivitis (species B and D) and/or gastroenteritis (species F and G). Recombinant adenoviruses and adenovirus vectors area commonly used to introduce heterologous genes into a cell, such as for gene therapy or therapeutic vaccination. In some cases, the recombinant adenovirus is replication defective (cannot undergo multiple rounds of replication).

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2. RANTES, GM-CSF, TNF-α, IFN-γ, G-CSF, LFA-3, CD72, B7-1, B7-2. OX-40L and 41 BBL. In some embodiments of the present disclosure, the adjuvant is a non-naturally occurring adjuvant.

Administration: The introduction of a composition into a subject by a chosen route. For example, if the chosen route is intravenous, the composition is administered by intnxlucing the composition into a vein of the subject. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes. In particular embodiments disclosed herein, the route of administration is subcutaneous or intramuscular.

Allogeneic: Refers to individuals, tissues or cells that are of the same species, but are antigenically distinct AB allogeneic plasma is plasma obtained from healthy normal (allogeneic) donors with blood type AB. AB plasma lacks antibodies to both blood group A and blood group B, making it universally compatible in blood type at the plasma level. AB allogeneic plasma can be from a single AB donor or a pool of AB donors. The plasma is tested and confirmed to be negative for infectious pathogens, e.g. hepatitis A, B, C, and HIV. AB allogeneic plasma used in the method disclosed herein is heat inactivated (HI AB) and is used to culture monocytes into mature dendritic cells as an alternative to the use of autologous plasma (plasma from the patient) in the process of generating therapeutic dendritic cell (DC) vaccines.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies and/or a CD4+ or CD8+ T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In some embodiments, T cells respond to the epitope, when the epitope is presented in conjunction with a major histocompatibility complex (MHC) molecule.

Antigen presenting cells (APCs): A type of cell that displays antigens complexed with major histocompatibility complex (MHC) proteins on their surface. Professional APCs are very efficient at internalizing antigen, processing it and then displaying small pieces of the antigen (peptides) bound to a MHC molecule on the cell membrane surface. The three main types of professional APCs include DCs, macrophages and certain B cells. DCs have the broadest range of antigen presentation and are the most important APC in processing antigens for presentation to T-cells, which recognize antigen-MHC complexes using their T cell receptors.

Autologous: Derived from the same individual. In the context of the present disclosure, "autologous" DCs used for treatment of a subject are DCs originally obtained from the subject.

Bladder cancer: Cancer that forms in tissues of the bladder. Most bladder cancers are transitional cell carcinomas (cancer that begins in cell, that normally make up the inner lining of the bladder). Other types include squamous cell carcinoma and adenocarcinoma. The cells that form squamous cell carcinoma and adenocarcinoma develop in the inner lining of the bladder as a result of chronic irritation and inflammation.

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV).

Cancer: A malignant neoplasm that has undergone characteristic anaplasia with loss of differentiation, increased rate of growth, invasion of surrounding tissue, and is capable of metastasis. For example, prostate cancer is a malignant neoplasm that arises in or from prostate tissue, and breast cancer is a malignant neoplasm that arises in or from breast tissue (such as a ductal carcinoma). Residual cancer is cancer that remains in a subject after any form of treatment given to the subject to reduce or eradicate the cancer. Metastatic cancer is a cancer at one or more sites in the body other than the site of origin of the original (primary) cancer from which the metastatic cancer is derived.

Checkpoint inhibitor: A class of drugs (typically antibodies) that target proteins that play a role in suppressing the immune response. Immune checkpoint inhibitors include, for example, antibodies that target CTLA-4, PD-1, PD-L1, TIM-3 or LAG-3.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating a HER2-positive cancer, such as breast cancer, gastric cancer, esophageal cancer, ovarian cancer, endometrial cancer, stomach cancer, uterine cancer, pancreatic cancer, prostate cancer, bladder cancer, colorectal cancer, salivary gland carcinoma, renal adenocarcinoma, mammary gland carcinoma, non-small cell lung carcinoma, or head and neck carcinoma. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis. Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody (or immunoconjugate or ADC) that binds HER2 used in combination with a radioactive or chemical compound.

Chimeric: Composed of at least two pans having different origins. In the context of the present disclosure, a "chimeric fiber" is an adenovirus fiber protein having amino acid sequence derived from at least two different serotypes of adenovirus. In particular embodiments, the chimeric fiber is comprised of an Ad5 tail domain and Ad35 shaft and knob domains.

Colorectal cancer: A cancer that originates in the colon and/or rectum.

Contacting: Placement in direct physical association; includes both in solid and liquid form.

Cytotoxic T lymphocyte-associated protein 4 (CTLA-4): A protein receptor found on the surface of T cells that functions as an immune checkpoint to downregulate the immune system. CTLA-4 is also known as CD152.

Dendritic cells (DCs): The principle professional antigen presenting cells (APCs) involved in primary immune responses. They are potent activators of T helper cell responses because as part of their composition, they express co-stimulatory molecules on their cell surface. Their major function is to obtain antigen in tissues, migrate to lymphoid organs and present the antigen in order to activate T cells. Immature dendritic cells originate in the bone marrow and reside in the periphery as immature cells. Dendritic cell sub-types include plasmacytoid dendritic cells and myeloid dendritic cells.

Drug: Any compound used to treat, ameliorate or prevent a disease or condition in a subject. In some embodiments herein, the drug is an anti-cancer agent, for example a cytotoxic agent, such as an anti-mitotic or anti-microtubule agent.

Ependymoma: A rare type of cancer that arises from the ependymal cells that line the ventricles and passageways in the brain and spinal cord.

Fiber: The adenovirus fiber protein is a trimeric protein that mediates binding to cell surface receptors. The fiber protein is comprised of a short N-terminal tail, a shaft domain and a C-terminal globular knob domain. In the context of the present disclosure. "an Ad35 fiber protein" is an adenovirus fiber protein in which at least the knob domain is made up of amino acid sequence from an Ad35 fiber protein. In some examples, the "Ad35 fiber protein" is comprised of an Ad35 shaft domain and an Ad35 knob domain. In yet other examples, the "Ad35 fiber protein" is substantially or completely an Ad35 fiber protein. In particular embodiments, the fiber protein is a chimeric fiber having an Ad5 tail domain and Ad35 shaft and knob domains.

Gastroesophageal cancer: Cancer that arises from tissues lining the esophagus or stomach.

HER2: A member of the epidermal growth factor (EGF) receptor family of receptor tyrosine kinases. HER2 is a transmembrane protein comprising extracellular (EC), transmembrane (TM) and intracellular (IC) domains (see FIG. 1A). This protein has no ligand binding domain of its own and therefore cannot bind growth factors. However, it does bind tightly to other ligand-bound EGF receptor family members to form a heterodimer, stabilizing ligand binding and enhancing kinase-mediated activation of downstream signaling pathways, such as those involving mitogen-activated protein kinase and phosphatidylinositol-3 kinase. Amplification and/or overexpression of the HER2 gene has been reported in numerous cancers, including breast and ovarian tumors. For example, amplification of the HER2 genes has been reported in approximately 20-25% of primary breast cancers. HER2 is also known as v-erb-b2 erythroblastic leukemia viral oncogene homolog 2, neuro/glioblastoma derived oncogene, epidermal growth factor receptor 2 (EGFR2), ERBB2 and Her-2/neu.

HER2-positive cancer: A cancer that overexpresses HER2. Examples of HER2-positive cancers include, but are not limited to, breast cancer, gastric cancer, esophageal cancer, ovarian cancer, endometrial cancer, stomach cancer, uterine cancer, pancreatic cancer, prostate cancer, bladder cancer, colorectal cancer, salivary gland carcinoma, renal adenocarcinoma, mammary gland carcinoma, non-small cell lung carcinoma and head and neck carcinoma.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a $CD8^+$ response. In another embodiment, the response is a B cell response, and results in the production of specific antibodies.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Lymphocyte activation gene 3 (LAG-3): A cell surface protein of the immunoglobulin superfamily expressed on activated T cells, natural killer cells, B cells and plasmacytoid dendritic cells. LAG-3 functions as a negative regulator of T cell activity. LAG-3 is also known as CD223.

Monocyte: A mononuclear, phagocytic leukocyte that is normally found in lymph nodes, spleen, bone marrow and loose connective tissue. Monocytes constitute 3-7% of the leukocytes in the circulating blood. Under appropriate culture conditions, monocytes from the peripheral blood can differentiate into dendritic cells.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Non-small cell lung cancer: The most common type of lung cancer. The three main types of non-small cell lung cancer are squamous cell carcinoma, large cell carcinoma, and adenocarcinoma.

Oncolytic virus: A virus that preferentially infects and kills cancer cells (for a review see Chiocca and Rabkin, *Cancer Immunol Res* 2(4):295-300, 2014).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Ovarian cancer: Cancer that forms in tissues of the ovary. Most ovarian cancers are either ovarian epithelial carcinomas (cancer that begins in the cells on the surface of the ovary) or malignant germ cell tumors (cancer that begins in egg cells).

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E.W. Martin. Mack Publishing Co., Easton, Pa., 15th Edition, 1975, describes compositions and formulations suitable for pharmaceutical delivery of the antibodies and conjugates disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Plasma: The fluid portion of blood in which the blood cells are suspended. Plasma is a clear, straw-colored liquid containing plasma protein, inorganic salts, nutrients and gases, as well as hormones and enzymes.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Programmed cell death protein 1 (PD-1): A cell-surface receptor belonging to the immunoglobulin superfamily that functions as an immune checkpoint to downregulate the immune system by preventing the activation of T cells. PD-1 is expressed on T cells and pro-B cells and binds two ligands, PD-L1 and PD-L2. PD-1 is also known as CD279.

Programmed death-ligand 1 (PD-L1): A type I transmembrane protein that plays a role in suppressing the immune system. PD-L1 is also known as CD274 and B7-H1. The receptor for PD-L1 is PD-1.

Prostate Cancer: A malignant tumor, generally of glandular origin, of the prostate.

Prostate cancer: include adenocarcinomas and small cell carcinomas. Many prostate cancers express prostate specific antigen (PSA), prostate stem cell antigen (PSCA), PSMA (prostate specific membrane antigen), prostatic acid phosphatase (PAP) as well as other tumor antigens.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid, protein or virus is one that has a sequence that is not naturally occurring or has a sequence that is made by an artificial combination of two otherwise separated segments of sequence. This artificial combination can be accomplished, for example, by chemical synthesis or by the artificial manipulation of isolated segments of nucleic acids, for example, by genetic engineering techniques.

Renal cell cancer: The most common type of kidney cancer. It begins in the lining of the renal tubules in the kidney. The renal tubules filter the blood and produce urine. Renal cell cancer is also called hypernephroma, renal cell adenocarcinoma, and renal cell carcinoma.

Sarcoma: A malignant tumor of the connective or other non-epithelial tissue.

Sequence identity: The similarity between amino acid or nucleic acid sequences is expressed in terms of the similarity between the sequences, otherwise referred to as sequence identity. Sequence identity is frequently measured in terms of percentage identity (or similarity or homology): the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI. Bethesda, Md.) and on the internet, for use in connection with the sequence analysis programs blastp, blastn, blastx, tblastn and tblastx. A description of how to determine sequence identity using this program is available on the NCBI website on the internet Homologs and variants of a $V_L$ or a $V_H$ of an antibody that specifically binds HER2 or a fragment thereof are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

T cell immunoglobulin and mucin domain 3 (TIM-3): An immune checkpoint receptor expressed on Th1 cells. TIM-3 limits the duration and magnitude of Th1 and cytotoxic T cell responses.

Therapeutically effective amount: A quantity of a specified agent sufficient to achieve a desired effect in a subject, cell or culture being treated with that agent. In the context of the present disclosure, a therapeutically effective amount of an AdHER2ECTM DC vaccine is an amount that causes induction of an immune response, as measured by clinical response (for example increase in a population of immune cells, production of antibody that specifically binds HER2, or measurable reduction of tumor burden).

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Disclosed herein is a recombinant Ad5-based vector that encodes the EC and TM domains of the human HER2 protein and an Ad35 fiber protein. In the context of the present disclosure, "an Ad35 fiber protein" is an adenovirus fiber protein in which at least the knob domain is made up of amino acid sequence from an Ad35 fiber knob. In some examples, the "Ad35 fiber protein" is comprised of an Ad35 shaft domain and an Ad35 knob domain. In yet other examples, the "Ad35 fiber protein" is substantially or completely an Ad35 fiber protein. In particular embodiments, the recombinant Ad5-based vector encodes a chimeric fiber protein having an Ad5 tail domain and Ad35 shaft and knob domains.

Also disclosed is a recombinant adenovirus expressing HER2ECTM and an Ad35 fiber protein, as well as isolated dendritic cells transduced with the HER2ECTM expressing recombinant adenovirus. Expression of the Ad35 fiber protein significantly increases the capacity of the recombinant adenovirus to infect human dendritic cells and other hematopoietic cells. Compositions comprising the recombinant HER2ECTM expressing adenovirus or dendritic cells transduced with the recombinant HER2ECTM expressing adenovirus can be used to elicit a HER2-specific immune response in a subject, such as a subject with a HER2-positive tumor.

Provided is a recombinant adenovirus vector encoding the EC and TM domains of human HER2 and an Ad35 fiber protein. In some embodiments, the nucleotide sequence of the vector is at least 80%, at least 85%, at least 90%, at least 95%, at least 96%, at least 97%, at least 98% or at least 995 identical to SEQ ID NO: 1. In some examples, the nucleotide sequence of the vector comprises or consists of the amino acid sequence of SEQ ID NO: 1. Further provided is a recombinant adenovirus expressing HER2ECTM produced by transforming isolated cells with the recombinant adenovirus vector disclosed herein. In some embodiments, the amino acid sequence of HER2ECTM is at least 80%, at least 85%, at least 90%, at least 95%, at least 96%, at least 97%, at least 98% or at least 99% identical to SEQ ID NO: 2. In specific examples, the amino acid sequence of HER2ECTM comprises or consists of SEQ ID NO: 2. In some embodiments, the isolated cells are mammalian cells, such as human embryonic kidney cells (for example, HEK-293 cells). Also provided are compositions comprising isolated dendritic cells (or dendritic cells grow from peripheral blood monocytes) transduced with the recombinant adenovirus expressing HER2ECTM. In some embodiments, the compositions further include AB allogeneic plasma, a pharmaceutically acceptable carrier, an adjuvant, or any combination thereof.

Also provided herein are compositions that include isolated dendritic cells transduced with a recombinant adenovirus (such as a recombinant Ad5) expressing the EC and TM domains of human HER2 (HER2ECTM) and an Ad35 fiber protein; and AB allogeneic plasma. In some embodiments, the amino acid sequence of HER2ECTM is at least 80%, at least 85%, at least 90%, at least 95%, at least 96%, at least 97%, at least 98% or at least 99% identical to SEQ ID NO: 2. In specific examples, the amino acid sequence of HER2ECTM comprises or consists of SEQ ID NO: 2. In some embodiments, the amino acid sequence of the fiber protein is at least 80%, at least 85%, at least 90%, at least 95%, at least 96%, at least 97%, at least 98% or at least 99% identical to SEQ ID NO: 3. In some examples, the amino acid sequence of the fiber protein comprises or consists of SEQ ID NO: 3. In some embodiments, the compositions further include a pharmaceutically acceptable carrier, an adjuvant, or both.

Further provided are methods of eliciting a HER2-specific immune response in a subject, and methods of treating a HER2-positive cancer in a subject, by administering to the subject a recombinant HER2ECTM expressing adenovirus or a composition disclosed herein. In some embodiments, the composition includes dendritic cells transduced with a recombinant adenovirus expressing HER2ECTM as disclosed herein. In some examples, the dendritic cells are autologous dendritic cells obtained from the subject. In some embodiments, the amino acid sequence of HER2ECTM is at least 80%, at least 85%, at least 90%, at least 95%, at least 96%, at least 97%, at least 98% or at least 99% identical to SEQ ID NO: 2. In specific examples, the amino acid sequence of HER2ECTM comprises or consists of SEQ ID NO: 2. In some embodiments, the amino acid sequence of the fiber protein expressed by the recombinant adenovirus is at least 80%, at least 85%, at least 90%, at least 95%, at least 96%, at least 97%, at least 98% or at least 99% identical to SEQ ID NO: 3. In some examples, the amino acid sequence of the fiber protein comprises or consists of SEQ ID NO: 3. In some embodiments of the methods, the compositions further include a pharmaceutically acceptable carrier, an adjuvant, or both.

Also provided herein is a method of treating a HER2-positive cancer in a subject by preparing autologous dendritic cells by culturing monocytes obtained from the subject in culture medium comprising AB allogeneic plasma; transducing the autologous dendritic cells with a recombinant adenovirus (such as a recombinant Ad5) expressing the EC and TM domains of human HER2 and an Ad35 fiber protein; and administering to the subject a composition comprising the autologous dendritic cells transduced with the recombinant adenovirus in a pharmaceutically acceptable carrier. In some embodiments, the medium further includes GM-CSF and IL-4. In some embodiments, the amino acid sequence of HER2ECTM is at least 80%, at least 85%, at least 90%, at least 95%, at least 96%, at least 97%, at least 98% or at least 99% identical to SEQ ID NO: 2. In specific examples, the amino acid sequence of HER2ECTM comprises or consists of SEQ ID NO: 2. In some embodiments, the amino acid sequence of the fiber protein expressed by the recombinant adenovirus is at least 80%, at least 85%, at least 90%, at least 95%, at least 96%, at least 97%, at least 98% or at least 99% identical to SEQ ID NO: 3. In some examples, the amino acid sequence of the fiber protein comprises or consists of SEQ ID NO: 3. In some embodiments, the compositions further include a pharmaceutically acceptable carrier, an adjuvant, or both.

In some embodiments of the methods disclosed herein, the HER2-positive cancer is a breast cancer, ovarian cancer, colorectal cancer, prostate cancer, renal cell cancer, bladder cancer, gastroesophageal cancer, sarcoma, ependymoma, or non-small cell lung cancer. In some examples, the cancer is metastatic. In particular non-limiting examples, the cancer is HER2 1+, 2+ or 3+ by IHC and/or has a VYSIS™ FISH result greater than 1.8.

In some embodiments, the subject to be treated has an advanced HER2-expressing metastatic solid tumor, such as a bladder, breast, cervical, colorectal, ovarian, non-small cell lung carcinoma (NSCLC), prostate, renal cell, gastroesophageal, or stomach tumor or a sarcoma or ependymoma.

In some embodiments, the subject to be treated is a patient with HER2-positive breast cancer that is resistant to trastuzumab, pertuzumab, ado-trastuzumab emtansine and/or other HER2-targeted therapies.

In some embodiments, the AdHER2ECTM DC vaccine is administered as an adjuvant treatment (administered after surgery with curative intent to reduce the incidence of disease recurrence). In other embodiments, the AdHER2ECTM DC vaccine is administered as a neoadjuvant treatment (administered before surgery with curative intent and documented by complete pathologic response).

In some embodiments of the methods, the subject is treated with one or more additional therapies or anti-cancer agents. In some examples, the additional therapy is selected from radiation, chemotherapy, surgical resection or any combination thereof. In some examples, the additional therapy is a checkpoint inhibitor, such as, but not limited to, an anti-CTLA-4, anti-PD-1, anti-PD-L1 agent, an anti-LAG-3 agent or an anti-TIM-3 agent (for example, an anti-CTLA-4, anti-PD-1, anti-PD-L1 antibody, an anti-LAG-3 antibody or an anti-TIM-3 antibody). In specific non-limiting examples, the anti-CTLA-4 agent is ipilimumab or tremelimumab; the anti-PD-1 agent is pembrolizumab, nivolumab or CT-011: or the anti-PD-L1 agent is avelumab or MEDI4736. In yet other examples, the additional therapy is a second therapeutic vaccine (such as a vaccine expressing a tumor antigen other than HER2), an oncolytic virus, an antibody specific for an immune-inhibitory cytokine or its receptor (for example, an antibody specific for TGF-β, IL-13 or IL-10), an agent that inhibits or depletes regulatory T cells, or an agent that inhibits or depletes myeloid suppressor cells. In some embodiments, the additional therapy is a natural killer T (NKT) cell agonist, such as β-mannosylceramide.

IV. Ad5f35HER2ECTM Vector and Autologous DC Vaccine

Despite significant advances in developing new treatments that substantially improve clinical outcomes for patients with HER2-positive breast and gastric cancer over the last 15 years, the need for additional unique therapies remains. Some patients with early-stage HER2-positive breast cancer either progress on, or relapse very early after, adjuvant (administered after surgery with curative intent) or neoadjuvant (administered before surgery with curative intent) trastuzumab-based therapy, suggesting primary resistance to trastuzumab treatment. Also, in virtually all patients with HER2-positive metastatic breast cancer, the disease eventually progresses. In addition, there are no HER2-targeted agents approved for non-breast HER2-positive solid tumors other than HER2-positive gastric and gastroesophageal junction tumors for which trastuzumab is approved. This highlights and reinforces the acute need for new therapies that target HER2 signaling in multiple tumor types, but with distinct mechanisms of action.

Figure 1B:
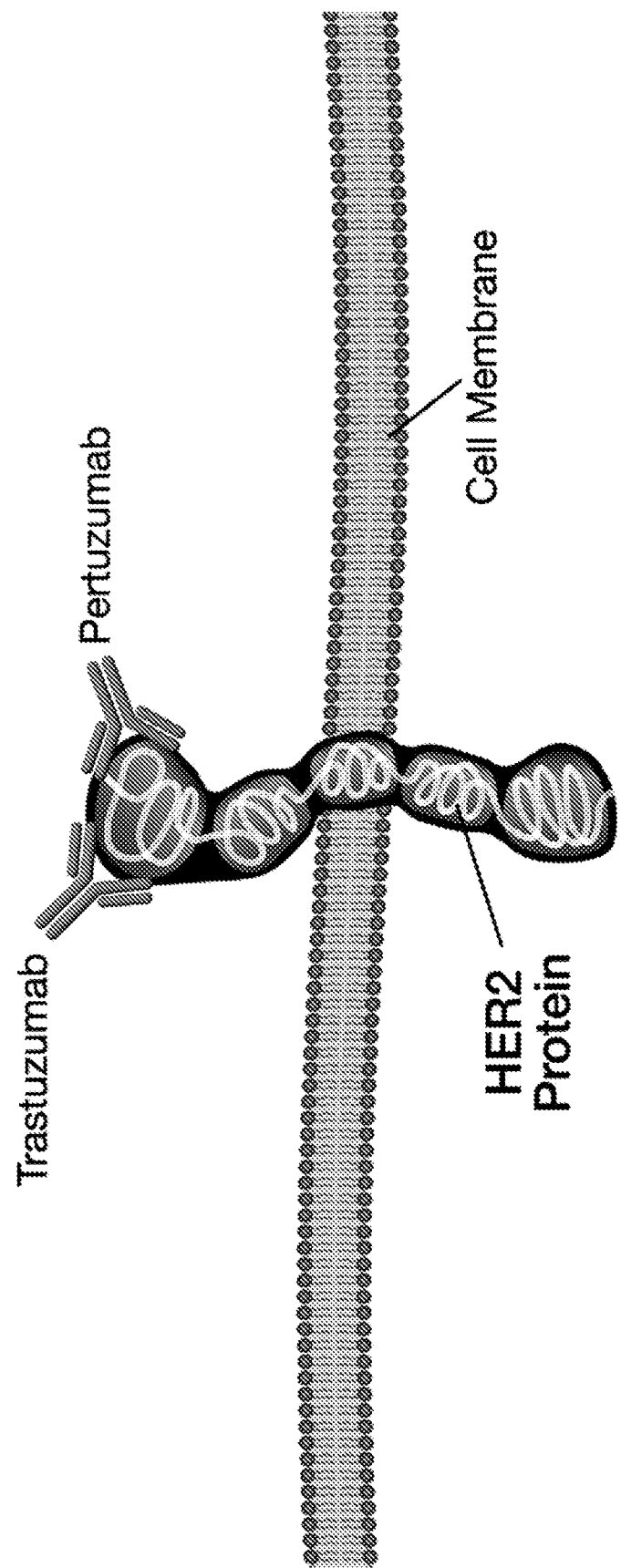

Tumors that over-express HER2 are associated with more aggressive disease, higher recurrence rates and reduced survival rates. The FDA-approved agents Trastuzumab (Herceptin®), pertuzumab (PERJETA™) and ado-trastuzumab emtansine (KADCYLA™) are monoclonal antibodies that each recognize one of two distinct, small portions of the extracellular domain of the HER2 protein (see FIG. 1B). Although these monoclonal antibodies have to be given repeatedly to have an effect, they have been shown to improve survival and reduce or slow disease progression in patients with HER2 expressing breast, gastric and gastroesophageal junction tumors. Despite their effectiveness in some cancers, trastuzumab, pertuzumab and ado-trastuzumab emtansine do not work for everyone and even when they are effective, they may stop working after some time. These monoclonal antibodies must be administered continuously every 3 weeks to have a beneficial treatment effect that is associated with significant inconvenience and cost to the patient. In addition, trastuzumab has been associated with decreased heart function (cardiac toxicity) in 3-7% of patients who receive it as a single agent, increasing to approximately 27% when given it is in combination with some chemotherapy. There are currently no therapeutic interventions that allow a patient to make their own antibodies directed against their own HER2 expressing tumors.

Figure 1C:
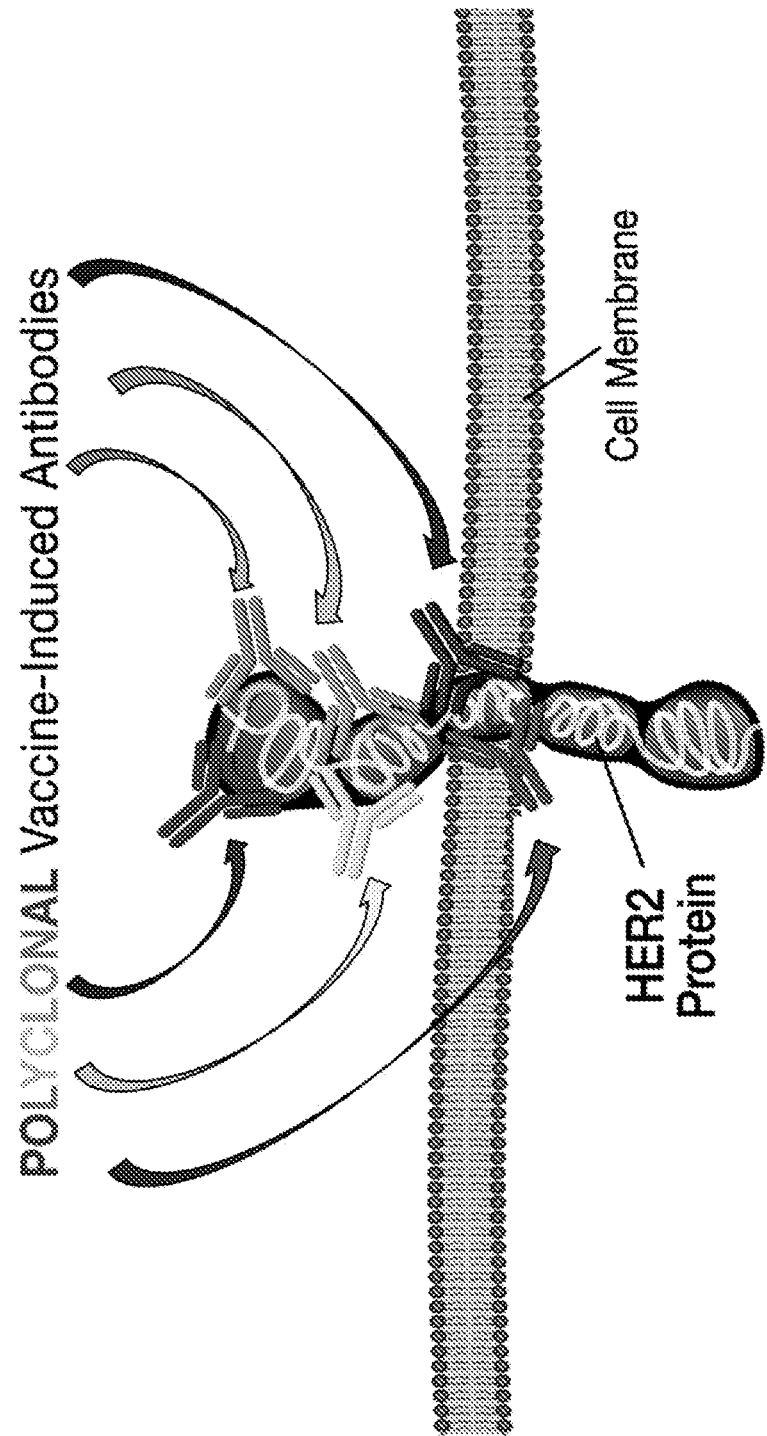

The human Ad5f35HER2ECTM vector platform disclosed herein is a unique immunogen platform designed to induce a polyclonal anti-tumor response (see FIG. 1C). This vaccine utilizes a recombinant adenoviral vector (Ad5f35) that expresses the EC and TM portions of the human HER2 protein (set forth herein as SEQ ID NO: 2). The intracellular (IC) portion of the HER2 protein was not included for safety purposes because it is the region of the HER2 protein believed to be responsible for its aggressive, pro-growth effects on tumor cells. The Ad5f35 adenoviral vector is a replication incompetent Ad5-based vector that expresses a chimeric fiber protein having an Ad5 tail and Ad35 shaft and knob domains (hence the Ad5f35 designation) to allow for greater transduction of the HER2-expressing adenovirus into human dendritic and other hematopoietic cells, and also to reduce the risk of neutralization by pre-existing Ad5 antibodies present in a subject. The amino acid sequence of the chimeric fiber protein is set forth herein as SEQ ID NO: 3. Once the recombinant adenovirus is inside cells (such as dendritic cells), the HER2 protein is expressed on the surface of the cells, which leads to an immune responses directed against the human HER2 protein, such as antibodies and cytotoxic T cells that recognize HER2 on the surface of tumors.

Other HER2 therapeutic vaccine platforms using human HER2 DNA, the entire HER2 protein, portions of the HER2 protein (e.g., intracellular domain protein), small pieces of the HER2 protein (HER2 peptides), other viral vectors that express HER2 (e.g., MVA-Modified Vaccinia Ankara virus), foreign tumor cell lines that over express HER2 (e.g., allogeneic GM-CSF secreting HER2 positive tumor cell lines that originated from patients) have been described in the art. An adenoviral vector that encodes the EC and TM domains of rat HER2/neu has also been previously described (Park et al., *Cancer Res* 68:1979-1987, 2008; Sakai et al., *Cancer Res* 64:8022-8028, 2004; WO 2004/041065). Treatment with the rodent HER2 vector caused regression and shrinkage of large established tumors in mice (Park et al., *Cancer Res* 68:1979-1987, 2008) and was also shown to protect against the development of breast cancer in transgenic mice (Sakai et al., *Cancer Res* 64:8022-8028, 2004). In another study using a model of mouse mammary carcinoma, it was determined that vaccine-induced antibodies to HER2 were responsible for the anti-tumor effect, preventing spontaneous autochthonous tumors in HER2-transgenic mice, and that CD4$^+$ Th1 cells played a role in developing these antibodies (Park et al., *J Immunol* 174:4228-4236, 20051.

The AdHER2ECTM vector platform disclosed herein encodes the entire EC and TM domains of human HER2. The IC domain, thought to be the primary component driving the ability of HER2 to transform cells and make them resistant to killing, is not present in the vaccine product to maximize its safety in humans and to focus the immune response on the more relevant portions of the HER2 protein for developing immunity. In addition, the adenovirus vector encodes a chimeric Ad5/Ad35 fiber protein (Ad5f35) having Ad35 shaft and knob domains and an Ad5 fiber tail domain. The substitution of the Ad5 shaft and knob with the shaft and knob of Ad35, whose receptor is CD46, allows for efficient and maximal transduction of human dendritic and hematopoietic cells by the recombinant adenovirus. In addition, the human AdHER2ECTM DC vaccine disclosed herein consists of autologous dendritic cells matured with lipopolysaccharide and IFN-γ and pulsed with keyhole limpet hemocyanin (KLH) in AB allogeneic plasma.

The AdHER2ECTM autologous DC vaccine or AdHER2ECTM vector (as a non-cellular vaccine) can be used in a variety of different patient populations. Exemplary patient populations include, but are not limited to, patients with advanced metastatic HER2-expressing (such as (1+ to 3+) solid tumors (e.g. bladder, breast, cervical, colorectal, ovarian, NSCLC, prostate, renal cell, gastroesophageal and stomach cancers); patients with HER2-positive breast cancer resistant to trastuzumab, pertuzumab, and ado-trastuzumab emtansine and/or other HER2-targeted therapies; patients with HER2-positive (such as 1+ to 3+ HER2-positive) bladder, breast, cervical, colorectal ovarian.

NSCLC, prostate, renal cell or stomach cancer, as adjuvant treatment (administered after surgery with curative intent to reduce the incidence of disease recurrence); and patients with HER2 positive (such as 1+ to 3+ HER2-positive) bladder, breast, cervical, colorectal, ovarian. NSCLC, prostate, renal cell, gastroesophageal or stomach cancer, as a neoadjuvant treatment (administered before surgery with curative intent).

V. Combination Treatments

Administration of the AdHER2ECTM vaccine compositions disclosed herein can be accompanied by administration of other therapeutic treatments (such as surgical resection of a tumor, radiation therapy, chemotherapy, and checkpoint inhibitors).

In some embodiments, the AdHER2ECTM dendritic cell vaccine is used in combination with a checkpoint inhibitor, such as antibodies (or fragments thereof) that target CTLA-4, PD-1, PD-L1, LAG-3 or TIM-3. In some examples, the checkpoint inhibitor is an anti-CTLA-4 antibody. CTLA-4 is a protein receptor found on the surface of T cells. When activated, CTLA-4 is capable of suppressing the immune system response. Anti-CTLA-4 antibodies block the connection necessary to engage this protein, allowing the T cells to continue fighting cancer cells, rather than shutting down the immune response. In other examples, the checkpoint inhibitors is an anti-PD-1 antibody. The PD-1 checkpoint pathway is another pathway for a T cell immune response. When the PD-1 receptors on the surface of T cells connect with the PD-L molecules on the surface of cancer cells or other immune cells, signals are sent to the T cells to dampen the response. Anti-PD-1 drugs block the connection necessary to engage this protein, allowing the T cells to continue their response against the cancer cells. In yet other examples, the checkpoint inhibitor is an anti-PD-L1 antibody. Cancer cells have the ability to make certain molecules appear on the surface, including PDL-1 and PDL-2 of the PD-1 checkpoint pathway. Cancer cells may also cause immune cells near the cancer to express PD-L1. These molecules bind to the PD-1 on the T cells and turn them off. In other examples, the checkpoint inhibitor is an anti-LAG-3 antibody. LAG-3 is a negative regulator of T cell activity. In other examples, the checkpoint inhibitor is an anti-TIM-3 antibody. TIM-3 is an immune checkpoint receptor that inhibits the duration and magnitude of Th1 and cytotoxic T cell responses, which dampens the anti-tumor immune response.

In some embodiments, a checkpoint inhibitor is co-delivered locally with the AdHER2ECTM dendritic cell vaccine at the injection site. In other examples, the checkpoint inhibitor is co-formulated within the vaccine platform. Co-delivery of a checkpoint inhibitor augments the vaccine response without the toxicity that is generally associated with the systemic delivery of these agents. Provided below is a list of exemplary checkpoint inhibitors that are either FDA approved or investigational agents:

| Agent | Checkpoint Target | FDA Approved/ Investigational | Clinical Indication |
|---|---|---|---|
| Ipilimumab (YERVOY™) | Anti-CTLA-4 | FDA Approved 2011 | 1st line treatment for unresectable or metastatic melanoma |
| Pembrolizumab (KEYTRUDA™) | Anti-PD-1 | FDA Approved 2014 | 2nd line treatment for metastatic melanoma no longer helped by ipilimumab |
| Nivolumab (OPDIVO™) | Anti-PD-1 | FDA Approved 2014 | 2nd line treatment for metastatic melanoma no longer helped by ipilimumab |
| | | FDA Approved 2015 | Metastatic NSCLC progressing after platinum-based chemotherapy |
| Tremelimumab | Anti-CTLA-4 | Investigational | Multiple cancers |
| CT-011 | Anti-PD-1 | Investigational | Multiple cancers |
| Avelumab (PF-06834635, MS80010718C) | Anti-PD-L1 | Investigational | Multiple cancers |
| MEDI4736 | Anti-PD-L1 | Investigational | Multiple cancers |

In some embodiments, the AdHER2ECTM dendritic cell vaccine is used in combination with antibodies directed against immune-inhibitory cytokines, such as TGF-β, IL-13, IL-10 or their receptors. Other combination treatments could include agents that inhibit or deplete regulatory T cells (for example, the IL-2 immunotoxin denileukin diftitox) and agents that inhibit or deplete myeloid suppressor cells (such as antibodies that target myeloid cell markers, for example anti-CD11b, anti-Gr-1).

In some embodiments, the AdHER2ECTM DC vaccine is administered in combination with another therapeutic vaccine that expresses a different tumor antigen (not HER2) also expressed by the patient's tumor cells. In some examples, the therapeutic vaccine is directed against TARP (see e.g., WO 2015/089469), which is expressed in approximately 95% of prostate and 50% of breast cancers.

In some embodiments, the AdHER2ECTM DC vaccine is administered in combination with a natural killer T (NKT) cell agonist In some examples, the NKT cell agonist is β-mannosylceramide (β-ManCer, see U.S. Pat. No. 8,835,613, which is incorporated herein by reference in its entirety). In some cases, a subject is administered a composition that includes β-mannosylceramide or a salt or solvate thereof in a pharmaceutically acceptable carrier.

In some embodiments, the AdHER2ECTM DC vaccine is administered in combination with chemotherapy. In some examples, chemotherapy is administered first to reduce the metastatic tumor.

In some embodiments, the AdHER2ECTM DC vaccine is administered in combination with an oncolytic virus that specifically targets cancer cells, or another vector-based vaccine.

In some embodiments, the AdHER2ECTM DC vaccine is administered in combination with radiation therapy.

In other embodiments, the AdHER2ECTM DC vaccine is administered in combination with another anti-cancer agent. Any suitable anti-cancer agent can be administered in combination with the compositions disclosed herein. Exemplary anti-cancer agents include, but are not limited to, chemotherapeutic agents, such as, for example, mitotic inhibitors, alkylating agents, antimetabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCN U, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571. Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech). GM-CSF (granulocyte macrophage colony stimulating factor; Genetics Institute), IL-2 (Cetus or Hoffman-LaRoche), human immune globulin (Cutter Biological), IMREG (from Imreg of New Orleans. La.). SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

The compositions disclosed herein can also be administered in combination with other HER2 directed therapies, such as one or multiple of the therapies discussed in the section below.

VI. Other HER2 Directed Therapies

Human epidermal growth factor receptor 2 (HER2, also known as c-erbB2 or neu) is a proto-oncogene that encodes a 185-kd transmembrane (TM) tyrosine kinase receptor that participates in receptor-receptor interactions that regulate cell growth, differentiation and proliferation. Its over-expression (HER2 oncogene amplification and/or overexpression of the HER2 protein) contributes to neoplastic transformation (Moasser et al., *Oncogene* 26:6469-6487, 2007). HER2 is overexpressed in up to 25-30% of node-positive or node-negative primary breast cancers and is associated with clinically aggressive breast cancer, a high recurrence rate and reduced survival (Slamon et al., *Science* 244:707-712, 1989). Development of agents targeting HER2 has resulted in expansion of therapeutic options and improved clinical outcomes for patients with HER2 overexpressing tumors (Moasser et al., *Oncogene* 26:6577-6592, 2007). Current FDA-approved treatment options include trastuzumab, lapatinib and pertuzumab.

Trastuzumab (HERCEPTIN™)

Trastuumab is an FDA-approved recombinant humanized mouse monoclonal antibody (MAb) that binds to the EC domain of the HER2 receptor. It is approved for the adjuvant treatment of early-stage breast cancer with nodal spread (or without nodal spread if the tumor is high risk) as well as for first and second line/salvage therapy for metastatic breast cancer. In the adjuvant setting, trastuzumab is used in several ways:

As part of a treatment course including chemotherapy with doxorubicin, cyclophosphamide and either paclitaxel or docetaxel With chemotherapy drugs docetaxel and carboplatin in a regimen known as "TCH"

Alone after treatment with multiple other therapies, including anthracycline-based therapy Trastuzumab has two approved uses in metastatic breast cancer:

As a first line treatment in combination with paclitaxel

As a single agent in patients who have received one or more courses of chemotherapy for metastatic disease.

Therapy typically involves an initial trastuzumab dose of 4 mg/kg IV followed by 2 mg/kg IV administered weekly for 52 weeks, alone (salvage therapy) or in combination with paclitaxel for the first 12 weeks (adjuvant and first-line therapy). However, clinical efficacy is limited to patients with 3+ HER2 tumor expression documented by immunohistochemistry (IHC) or a VYSIST™ fluorescent in situ hybridization (FISH) ratio of >2.2. IHC is a subjective measurement of HER2/neu protein while FISH is an objective measurement of amplification of the HER2 oncogene (Wolff et al., *J Clin Oncol* 25:1-28, 2007). Despite the high level efficacy in combination with chemotherapy, the overall response rate of women diagnosed with HER2-positive metastatic breast cancer and treated with trastuzumab as a single first-line agent is only 26% (Vogel et al., *J Clin Oncol* 20:719-726, 2005), clearly indicating there is room for improvement in therapeutic options. In addition, a significant number of patients are unresponsive to trastuzumab and most eventually experience clinical progression while on therapy, presumably due to trastuzumab resistance, whose mechanism is poorly understood (Lan et al., *Ann NY Acad Sci* 1059:70-75, 2005; Harris et al., *Clin Cancer Res* 13:1198-1207, 2007; Berns et al., *Cancer Cell* 12:395-402, 2007). Trastuzumab is also approved for use in combination with cisplatin and either capecitabine or 5-fluorouracil in treatment naïve patients with HER2-positive metastatic stomach cancer or cancer of the gastroesophageal junction. However, no vaccine is currently available that induces patients to make their own anti-HER2 antibodies.

Trastuzumab Cardiac Toxicity

Given the well-documented cardiac toxicity associated with the monoclonal antibody trastuzumab (Seidman et al., *J Clin Oncol* 20:1215-1221, 2002; Piccart-Gebhart et al., *N Engl J Med* 353:1659-1672, 2005; Tan-Chiu et al., *J Clin Oncol* 23:7811-7819, 2005), the AdHER2ECTM DC vaccine disclosed herein was initially be assessed for safety as a single agent to minimize confounding attributions of toxicity. Specifically, a retrospective review of records for patients enrolled onto any of seven phase II and III trastuzumab clinical trials revealed patients treated with trastuzumab were found to be at increased risk for cardiac dysfunction (Seidman el al., *J Clin Oncol* 20:1215-1221, 2002). The incidence was greatest in patients receiving concomitant trastuzumab and anthracycline plus cyclophosphamide (27%), but was substantially lower in patients receiving paclitaxel and trastuzumab (13%) or trastuzumab alone (3% to 7%), although most of these patients had received prior anthracycline therapy. Most trastuzumab-treated patients that developed cardiac dysfunction were symptomatic (75%), and most improved with standard treatment for congestive heart failure (79%). Consequently, the clinical study is conducted in two parts to identify any cardiac safety issues that may be associated with vaccine-induced antibodies. Part I of the study involves vaccine dose escalation in a population with no prior exposure to trastuzumab or other HER2 directed agents to determine if there is a significant, adverse safety signal regarding cardiac toxicity. Assessments of cardiac function include serial echocardiography to determine left ventricular ejection fraction (LVEF) at baseline and at regular monitoring intervals, in addition to LVEF measurements for at least 2 years following receipt of the last dose of vaccine. Once cardiac safety has been established in this population, Part II repeats the vaccine dose escalation in a population with significant prior exposure to trastuzumab to determine whether there is an adverse safety signal regarding cardiac toxicity using identical monitoring and follow-up criteria.

Lapatinib

Lapatinib is an orally administered tyrosine kinase inhibitor of both the HER2/neu protein and the epidermal growth factor receptor. It has shown activity in combination with capecitabine in patients with metastatic HER2 positive breast cancer that have progressed following treatment with trastuzumab (Geyer et al., *N Engl J Med* 355:2733-2743, 2006). Common toxicities specific to lapatinib include diarrhea and rash; cardiac toxicity is rarely seen. Like trastuzumab, resistance to lapatinib has been described and it appears that multiple molecular mechanisms underlie resistance to both of these drugs (Koninki et al., *Cancer Lett* 294(2):211-219, 2010).

Pertuzumab

Pertuzumab is a humanized monoclonal antibody being studied in early and advanced states of HER2-positive breast cancer and advanced HER2-positive gastric cancer. It is a dimerization inhibitor designed to specifically prevent the HER2 receptor from pairing with other HER receptors (EFGR/HER1, HER3 and HER4), a process that is believed to play a critical role in the growth and formation of several different cancer types. Through prevention of receptor pairing, pertuzumab is believed to block cell signaling, which may inhibit cancer cell growth or lead to the death of the cancer cell. Binding of pertuzumab to HER2 may also signal the body's immune system to destroy cancer cells. The mechanisms of action of pertuzumab and trastuzumab are thought to complement each other, as both bind to the HER2 receptor but on different regions. The goal of combination pertuzumab/trastuzumab therapy and chemotherapy is to determine if the combination provides a more comprehensive blockade of HER signaling pathways.

The pertuzumab application before the FDA is based on results from the pivotal phase III CLEOPATRA (Clinical Evaluation Of Pertuzumab And TRAstuzumab) study (Baselga et al., *N Engl J Med* 366:109-119, 2012). CLEOPATRA is an international, phase HI, randomized, double-blind, placebo-controlled study. The study evaluated the efficacy and safety profile of the pertuzumab-based regimen compared to trastuzumab and chemotherapy plus placebo in 808 people with previously untreated HER2-positive metastatic breast cancer. The primary endpoint of the study was progression free survival (PFS) with secondary endpoints of overall survival (OS), PFS by investigator assessment, safety profile, overall response rate (ORR), duration of response, time to symptom progression and correlation of biomarkers with clinical outcomes. The CLEOPATRA study demonstrated a 6.1-month improvement in median PFS for patients receiving a pertuzumab-based regimen (pertuzumab combined with trastuzumab and docetaxel) compared to those who received trastuzumab and docetaxel alone: median PFS 18.5 vs. 12.4 months. People who received the combination also experienced a 38% reduction in the risk of disease worsening or death (HR=0.62, p-value <0.0001). The pertuzumab regimen was not associated with a higher incidence of cardiac AEs: left ventricular dysfunction was 4.4% in the pertuzumab-containing regimen compared to 8.3% with trastuzumab and docetaxel alone.

Trastuzumab Emantansine (T-DM1)

Trastuzumab emantansine (T-DM1) is an antibody-drug conjugate consisting of trastuzumab linked via a non-reducible thiother to the cytotoxic, anti-tubulin agent maytansine (DM1) (LoRusso et al., *Clin Cancer Res* 17:6437-6447, 2011). It is under global development for second-line, first-line and third-line treatment of HER2+ metastatic breast cancer in several phase Ill trials.

The results of a 137 patient, randomized phase 11 study of T-DM1 in untreated HER2+ metastatic breast cancer patients comparing T-DM1 versus trastuzumab plus docetaxel chemotherapy demonstrated improved median PFS of T-DM1 compared to trastuzumab/docetaxel: median PFS of 14.2 months vs. 9.2 months, respectively; p=0.035. T-DM1 achieved a 64.2% objective response rate vs. 58% for the trastuzumab/docetaxel combination and also had a more favorable side effect profile, with a lower frequency of severe adverse events (SAEs): 46.4% vs. 89.4% respectively. The most frequent SAEs reported with T-DM1 therapy were thrombocytopenia (8.7%) and elevated liver transaminases (8.7%).

VII. Pre-Clinical Animal Studies

A previously published study documented the regression and cure of large established tumors in syngeneic BALB/c mice using a therapeutic adenoviral vector vaccine expressing the extracellular and transmembrane (ECTM) domains of rodent HER2neu (Park et al., *Cancer Res* 68:1979-1987, 2008). This anti-tumor activity is mediated by polyclonal vaccine-induced antibodies that inhibit HER2 phosphorylation and unlike trastuzumab, are Fc receptor independent. Although many mouse tumor vaccine studies have prevented growth of tumors, it has generally not been possible to achieve cure of large established tumors greater than 1 cm in diameter with cancer vaccines. Using an adenoviral vector vaccine expressing the extracellular and transmembrane (ECTM) domains of rodent HER2/neu. TUBO mammary gland carcinomas up to 2 cm in diameter were cured in syngeneic BALB/c mice and multiple large established lung metastases. Virtually 100% of mice were cured from both subcutaneous and lung tumors. The vaccine also prevented spontaneous orthotopic breast carcinomas in BALB/c mice transgenic for the same rodent neu oncogene (Park et al., *Cancer Res* 68:1979-1987, 2008; Park et al., *J Immunol* 174:4228-4236, 2005).

The vaccine's mechanism of action is antibody-mediated, with no involvement of CD4 or CD8 T cells in the effector function (only CD4 help at the time of vaccination to induce antibodies). Neither depletion of CD8+ T cells with antibody nor use of beta-2 microglobulin knockout mice that lack CD8+ T cells affected vaccine-induced protection.

Rodent AdneuECTM DC Vaccination

Similar induction of therapeutically effective antibodies was obtained by immunizing with 1 million syngeneic dendritic cells transduced with the AdneuECTM vector. Mice given TUBO cells subcutaneously and then vaccinated on days 5 and 7 when the tumors were 55-250 mm$^3$ showed complete regression of tumors exactly analogous to the regressions induced by the free AdHER2. Tumors continued to grow to a peak around Day 12, when they reached a maximum of 756 mm$^3$, and then started to regress, reaching baseline levels after Day 22. This therapeutic effect was observed whether AdneuECTM-transduced DCs were given alone or with IL-15 and was also antibody dependent. Thus, immunization with AdneuECTM-transduced DCs and with free AdneuECTM both produced comparable antibody-mediated tumor regression. Also, sera from such AdneuECTM-transduced DC-immunized mice inhibited growth of TUBO cells in vitro and inhibited phosphorylation of the ErbB2-neu oncoprotein.

Central and Peripheral Tolerance in the Transgenic HER2 Mouse Model

HER2/neu-transgenic mice have central or thymic tolerance to the oncogene, which is expressed from before birth (unlike some models in which an oncogene is not expressed until sexual maturity). They express a smaller, more limited and different T cell repertoire from that in non-transgenic mice, reflecting the deletion of many T cell clones by central self-tolerance (Rolla et al., *J Immunol* 177:7626-7633, 2006; Cavallo et al., *Nat Rev Cancer* 7:707-713, 2007). Thus, it has been harder to treat established spontaneous tumors in the neu-transgenic mice (Park et al., *J Immunol* 174:4228-4236, 2005; Sakai et al., *Cancer Res* 64:8022-8028, 2004). Further, in the BALB-neu transgenic model, the oncogene is expressed in all mammary cells of all mammary glands. As a consequence, relentless malignant transformation of mammary gland cells is induced with subsequent generation of independent primary tumors in all 10 mouse mammary glands, making it extremely difficult to suppress all tumors. In contrast, it is still possible to virtually completely suppress the development of tumors in neu-transgenic mice if vaccination is started at a young age, about 7 weeks, when histopathology already shows development of abnormal mammary gland dysplasia (beginning even before 4 weeks) due to the oncogene. Presumably the vaccine-induced antibodies are eradicating or inhibiting the dysplastic neu-expressing cells. Thus, this is really a therapeutic model, not just prophylactic. This situation contrasts with the human breast cancer situation, in which the HER2/neu oncogene is not expressed until malignant transformation in adulthood, so there is no opportunity to develop central tolerance. Indeed, Disis and coworkers (Disis et al., *Cancer Res* 54:16-20, 1994; Disis et al., *Breast Cancer Res Treat* 62(3): 45-52, 2000) have demonstrated that many patients with HER2+ breast cancers express spontaneous antibodies and T cell responses to the HER2 oncoprotein, demonstrating the absence of central tolerance. Further, humans with breast cancer generally do not have such an oncogene expressed in 100% of mammary gland ductal epithelial cells as in the transgenic mice, leading to the relentless and continuous generation of new independent tumors. Therefore, it is expected that the vaccine will be more effective at inducing therapeutically effective antibodies to HER2 in patients with HER2+ breast cancers than it can in centrally tolerant neu-transgenic mice.

It has also been demonstrated that vaccine-induced antibodies inhibit the growth of the N202-1A tumor line, another mouse mammary carcinoma expressing the same oncogene. The vaccine's mechanism of action is purely antibody-mediated, with no involvement of CD4 or CD8 T cells in the effector function (only CD4 help at the time of vaccination to induce antibodies). The vaccine-induced antibodies work differently from trastuzumab: they are Fc receptor independent, kill tumor cells directly without the aid of other cells, and inhibit HER2 phosphorylation and cause it to be modulated off the cell surface. Thus, this vaccine may work in patients in whom trastuzumab or lapatinib is ineffective. In addition, vaccine-induced antibodies are polyclonal and may be more resistant to escape mutations than a MAb like trastuzumab or pertuzumab. Pre-clinical animal data suggest the potential for even greater therapeutic efficacy than trastuzumab and would eliminate the need for costly, frequent infusions currently associated with this treatment.

Dendritic Cell Vaccines

There are a wide variety of platforms and immunogens that have been extensively studied in therapeutic cancer vaccine platforms including: a) whole tumor cell vaccines, b) dendritic cell (DC)-based platforms, c) peptide and fusion proteins co-delivered with adjuvants and c) viral vectors that serve as delivery vehicles for tumor-associated antigens (TAAs). In addition to classic peptide and protein immunogens, tumor lysates, tumor mRNA, and DNA have all been utilized. DCs serve as a bridge between the innate and adaptive immune system and in turn play a critical role in the activation of naïve CD4+ and CD8+ T cells. As a consequence, researchers in cancer immunotherapy have focused a tremendous amount of investigative effort to delineate and understand DC biology, activation, maturation, and antigen presentation. Because of the pervasive dysfunction of DCs in vivo as a consequence of the immune dysregulation associated with high tumor burdens (Finn, *N Engl J Med* 358:2704-2715, 2008). DCs have been the platform of choice for delivery of many tumor cell lines (LNCaP, PC3), peptides, proteins, lysates, mRNAs and viral vectors expressing TAAs (Kiessling et al. *Eur Urol* 53:694-708, 2008; Tanaka et al., *Clin Immunol* 101:192-200, 2001). Sipuleucel-T (PROVENGE™) is a prototype of this platform approach: even though it is labeled as an autologous cellular immunotherapy, its generation utilizes similar maturation agents and pathways common to dendritic cell vaccines (Higano et al., *Nat Reviews Drug Discov* 9:513-514, 2010).

A better understanding of basic immunologic principles has led to a variety of techniques for enhancing tumor-specific immunity and their potential subsequent translation into improved clinical outcomes. This is exemplified by the FDA approval of sipuleucel-T, the first licensed therapeutic cellular immunotherapy in the field of cancer. Approval of sipuleucel-T was based upon a statistically persuasive and clinically meaningful 4.1 month improvement in median overall survival (OS) in a phase III trial (Kantoff et al., *N*

Engl J Med 363(5):411-422, 2010). The improvement in OS associated with sipuleucel-T has been reported to correlate with CD54 upregulation, a measure of the product's potency (Higano et al., *Cancer* 115:3670-3679, 2009) as well as the development of antibody titers exceeding 400 at any time against the immunizing antigen PA2024 (a fusion protein) or prostatic acid phosphatase (PAP) (Kantoff et al., *N Engl J Med* 363(5):411-422, 2010). Although very strong T cell proliferative responses to PA2024 and PAP were also observed in patients receiving sipuleucel-T, no difference or association in survival was documented between patients who exhibited T cell response to either antigen and those who did not.

DC vaccine products have been delivered intravenously (as is sipuleucel-T), intramuscularly, intranodally, intradermally and subcutaneously. In the pre-clinical model of rodent AdneuECTM DC vaccination, the vaccine was given subcutaneously. The human autologous AdHER2ECTM DC vaccine disclosed herein is administered intradermally since there is evidence to suggest that in humans intradermal delivery is be more optimal than subcutaneous delivery.

HER2 Therapeutic Vaccines

The clinical efficacy of trastuzumab-based anti-HER2 passive immunotherapy and other HER2-targeted therapy has led to the development of vaccination strategies against HER2 that would ideally result in strong immunity producing immune memory associated with anti-tumor activity as well as prevention of tumor recurrence. Different anti-HER2 vaccine strategies currently under investigation and in various stages of clinical development include DNA, peptide, whole tumor cell, and dendritic cell vaccines and combinations of the same, e.g. peptide-loaded DC vaccines (Ladjemi et al., *Cancer Immunol Immunother* 59:1295-1312, 2010). Peptide vaccines have included monovalent and as well as polyvalent HER2 peptides and been associated with the development of humoral as well as cellular immune responses. The AdHER2EDTM DC vaccine disclosed herein is advantageous in its ability to induce polyclonal antibody responses directed towards both the EC and TM components of HER2, as well as potentially the intracellular domain (IC) as a result of epitope spreading. The multiple, unique HER2 epitopes targeted by this autologous vaccine platform are likely to differ from trastuzumab binding epitopes and may result in greater affinity and clinical activity than that seen with trastuzumab, especially in patients with lower levels of HER2 expression i.e. <3+ by IHC. In addition, the pre-clinical data indicates that the anti-HER2 antibodies induced by vaccination have functional activity that, unlike trastuzumab, is Fc receptor independent and that interfere with HER2 expression and phosphorylation. Hence, vaccine-induced anti-HER2 antibodies have clinically relevant anti-tumor activity in patients with resistance to trastuzumab, lapitinib or other HER2-directed therapies.

Norell et al. (*J Transl Med* 8:53, 2010) describe a pilot clinical trial of a plasmid DNA human HER2/neu vaccine encoding the EC, TM, and mutated intracellular (ICmutated) domains (ECTMICmutated), administered with GM-CSF and IL-2. As a safety measure, a two base pair mutation was introduced in the IC domain to remove an autophosphorylation site that confers oncogenicity. The vaccine was administered to a total of eight patients and no clinical issues of acute toxicity, autoimmunity or cardio toxicity were identified. The vaccine demonstrated limited immunogenicity: no specific T-cell proliferation following in vitro stimulation of ex vivo PBMCs with recombinant human HER2 protein was induced by vaccination. In fact, immediately following three complete cycles of vaccination, no or even decreased HER2-specific CD4+ T-cell responses were observed, but a significant increase in MHC class II restricted HER2-T-cell responses was detected at long term follow-up. Because concurrent trastuzumab therapy was permitted during the study, λ-subclass specific ELISAs were performed to measure endogenous antibody production without trastuzumab interference. In a subgroup of patients, HER2-pDNA vaccination induced and boosted HER2-specific antibodies that could be detected for several years following the last vaccine administration.

The following examples are provided to illustrate certain particular features and/or embodiments. These examples should not be construed to limit the disclosure to the particular features or embodiments described.

EXAMPLES

Example 1: Pre-Clinical AdHER2ECTM Vector Expression

Pre-clinical experiments were conducted to determine the optimal conditions for generation of AdHER2ECTM transfected dendritic cells (referred to herein as "AdHER2ECTM DC") for autologous therapeutic vaccination. Healthy normal donor cells were used to generate dendritic cells under different conditions to confirm HER2neu expression by FACS or ELISA in multiple experiments. A summary of the outcomes from these experiments is provided below.

Equivalent HER2neu expression of DCs transfected under bag or flask conditions. The study disclosed herein used bags to generate DCs from thawed monocytes for autologous DC vaccines.

A viral particle (VP):DC ratio of 3000:1 was chosen as the ratio for transfection for this clinical trial since high level expression was documented at reasonable MOIs based on data in the tables below.

| FACS Data - HER2neu Expression with Varying VP:DC Ratios | | | | |
|---|---|---|---|---|
| VP:DC Ratio | Population | Expression Marker | # Events | % Parent |
| 1000:1 | FITC G1 HER2 | HER2 | 6,947 | 26.8 |
| 2000:1 | FITC G1 HER2 | HER2 | 20,571 | 79.4 |
| 3000:1 | FITC G1 HER2 | HER2 | 24,657 | 95.0 |
| 5000:1 | FITC G1 HER2 | HER2 | 24,073 | 99.5 |

HER2neu mean fluorescent intensity and the percent of cells staining positive for HER2neu was acceptable at the two highest ratios examined:

| VP:DC Ratio | Mean Fluorescent Intensity (MFI) | % Cells Positive (DY and N87) for HER2neu |
|---|---|---|
| 3000:1 | 103 | 84.5% |
| 5000:1 | 432 | 97.8% |

Example 2: Pre-Clinical HER2 Dendritic Cell Platform

Figure 4A:
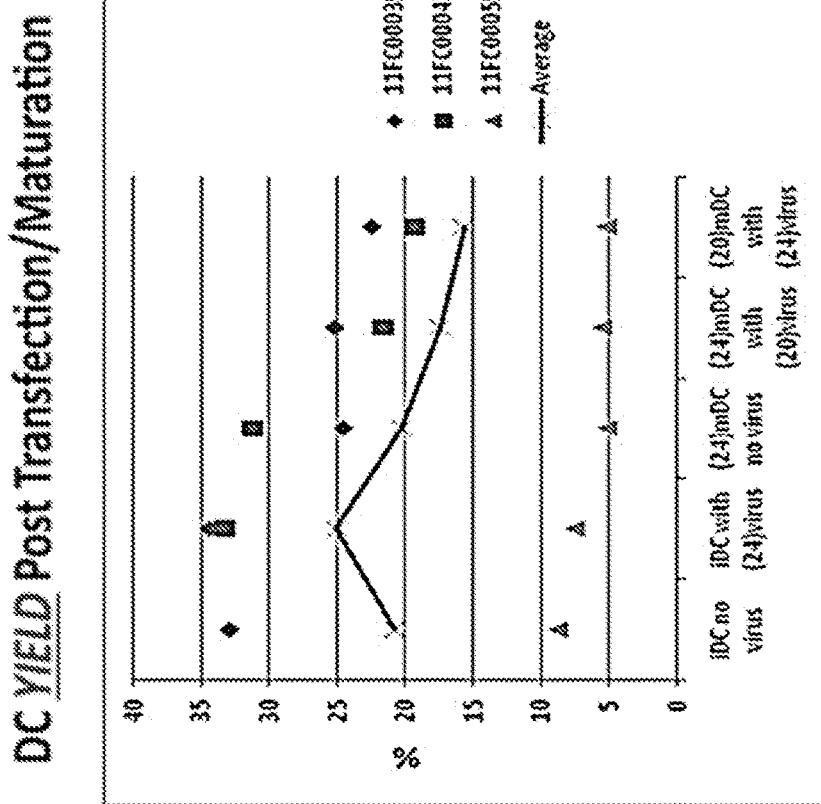
FIGS. 4A-4B are graphs showing the dendritic cell viability (FIG. 4A) and yield (FIG. 4B) post-transfection/maturation under each condition (as outlined in FIG. 3).
Figure 4B:
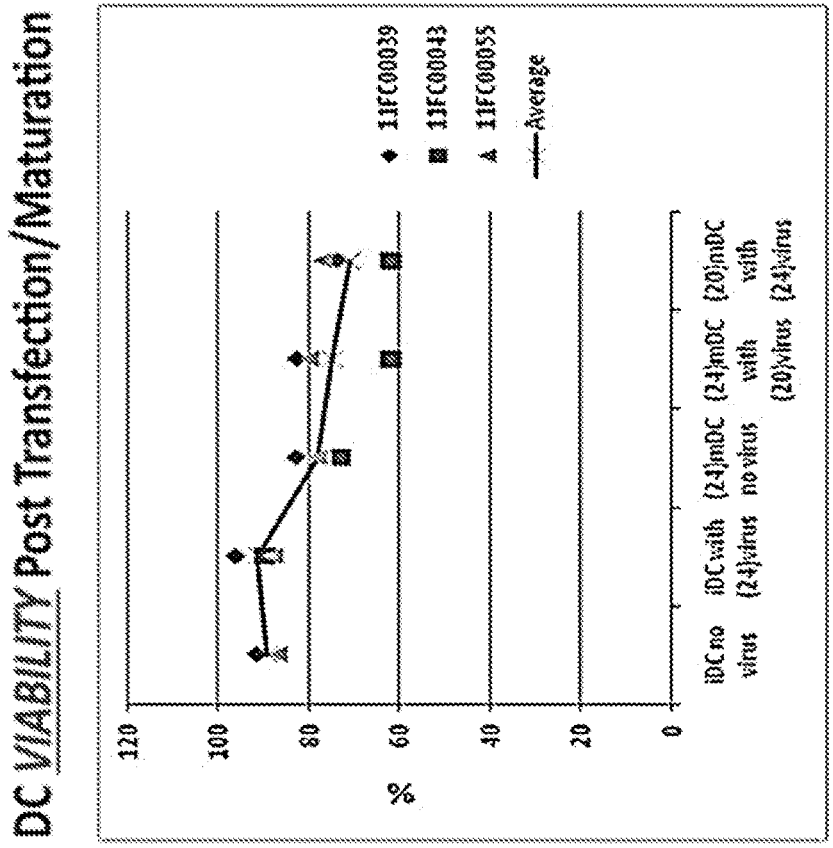

Studies were conducted utilizing cells from three healthy, normal human donors (11FC00039, 11FC00043 and 11FC00055) to determine the best order for AdHER2ECTM vector transfection and dendritic cell maturation for optimal viability and HER2neu expression in the final DC vaccine product. AdHER2ECTM transfected DCs at a ratio of 3000 VP:DC were generated under the following conditions as summarized below (and outlined in FIG. 3):

Transfection of immature dendritic cells (iDC) for 24 hours: iDC with (24 h) virus Immature dendritic cells with no viral transfection: iDC Maturation of DCs for 24 hours with no viral transfection: (24 h) mDC no virus Maturation of DCs for 24 hours with transfection at 20 hours: (24 h) mDC with (20 h) virus Transfection of DCs for 4 hours followed by maturation of DCs: (20 h) mDC with (24 h) virus As depicted in FIG. 4A, the post transfection viability of mature DCs (mDCs) ranged from 60-82% (mean 70-75%). Historically, the product yield for transfected DC vaccine products is usually between 10-40% of the starting monocyte population. As shown in FIG. 4B, yield of DCs post maturation/transfection was variable between donors.

Figure 5:
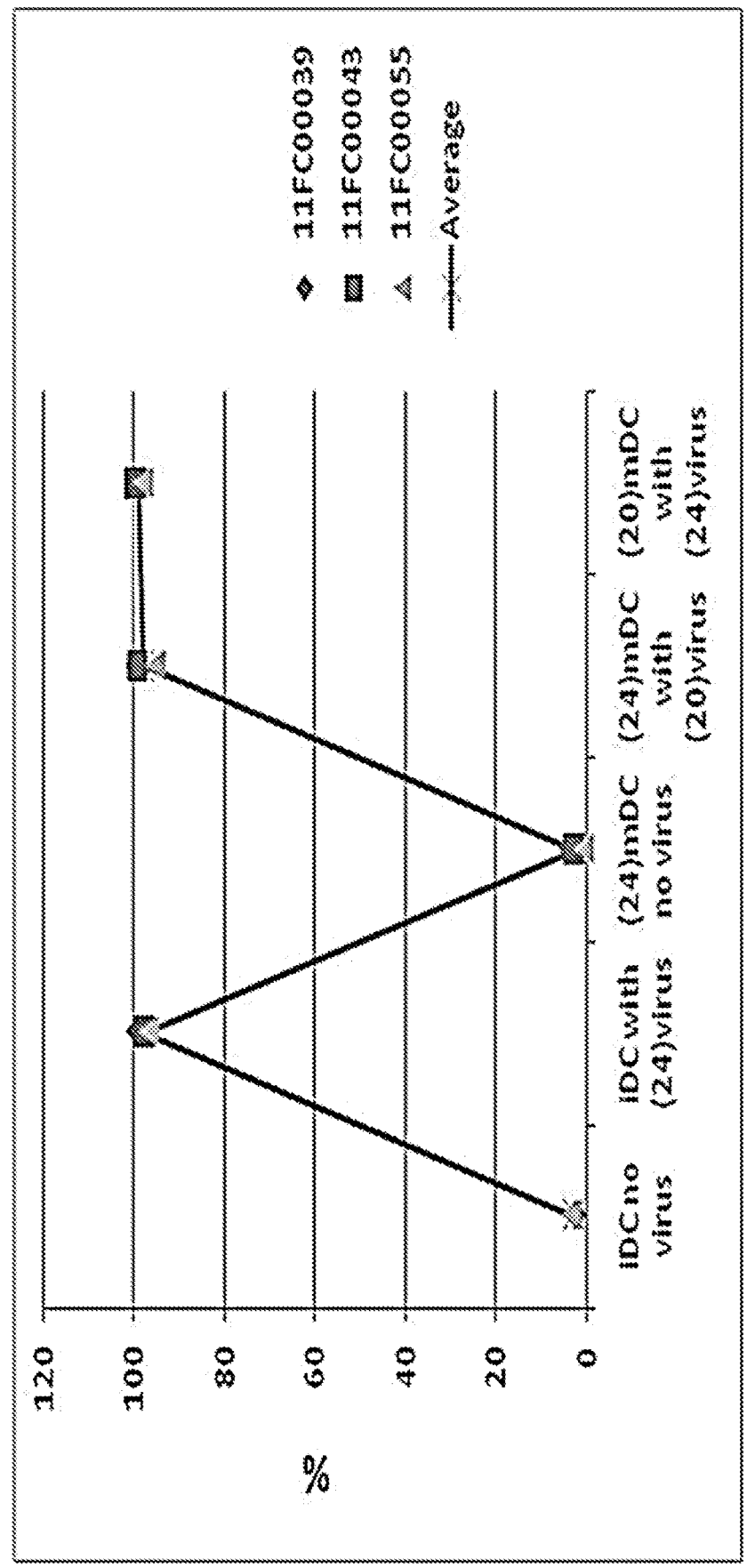
FIG. 5 is a graph showing expression of HER2 in dendritic cells processed according to the different conditions outlined in FIG. 3.

HER2neu expression was also assessed under the different maturation conditions. There was variability of expression within and between donors under the different maturation and transfection conditions, and immature DCs were observed to have greater variable expression of HER2neu. i.e. the mean fluorescent intensity per cell of HER2 expression was more inconsistent on immature DCs versus mature DCs. However, as documented below in FIG. 5, HER2neu expression (CD340) was 100% on transfected immature and mature DCs, regardless of transfection conditions.

Additional characterizations and assessments were also performed as part of these DC maturation/transfection experiments to better characterize the qualitative, functional aspects of the final HER2neu DC vaccine product, including:

Cluster of Differentiation (CD) antigens on the final DC vaccine product: CD86, CD83, HLA-DR, CD38, CD54, CD14, and CCR7

Expression of cytokines and chemokines IL-6, IL-8, IL-12p70, TNF-α, IP10, MDC and MIP3β (expressed as a ratio that normalizes expression for the number of cells). Interferon-α, IL-10, IL-13 and IL-15 were at very low concentrations, usually <5 pg/ml.

The AdHER2ECTM DC vaccine for this study was manufactured using a 4 hour transfection of the AdHER2ECTM vector first followed by the DC maturation cocktail (denoted as (20) mDC with (24) virus in the previous figures). This decision was based on the following observations from the in vitro studies described above:

It is generally easier to transfect immature DCs, i.e. before maturation cocktail is added to ensure optimal antigen processing.

There was more consistent HER2neu expression on mature DCs compared to immature DCs as measured by MFI, which leads to greater uniformity of the final product.

Example 3: Human Phase I Clinical Trial

This example describes a human Phase I clinical study to determine the safety and toxicity of autologous AdHER2ECTM dendritic cell vaccination. Specifically, to determine if the fraction of patients with cardiac toxicity (if it occurs) is sufficiently low to warrant further development in subsequent trials. Cardiac toxicity is defined as a decrease in LVEF≥10% or a decrease in absolute LVEF to <50% (equivalent to a Grade II decrease in LVEF per CTCAE v4.0). The study was also initiated to determine the immunogenicity of autologous AdHER2ECTM dendritic cell vaccination as measured by a 3-fold increase in anti-HER2/neu antibody concentration (measured as mcg/ml) or a 4-fold increase in antibody dilution titers over baseline.

Additional aims of the clinical study include determining the preliminary activity of autologous AdHER2ECTM dendritic cell vaccination as measured by the fraction of subjects who have stable disease, a partial response or better by immune-related response criteria; determining the impact of autologous AdHER2ECTM dendritic cell vaccination on tumor growth rate and regression rate constants; characterizing vaccine-induced antibody profiles using HER2 peptide microarrays, examining reactivity to HER2 EC. TM and IC domains; and characterizing and measuring function-associated mRNAs in whole blood, circulating tumor cells, and other potential biologic/immunologic correlates of clinical response. A study design schema for the AdHER2ECTM DC vaccination trial is shown in FIG. 6.

Eligibility Criteria

Inclusion Part I

Adults at least 18 years of age with recurrent or progressive, metastatic solid tumors characterized by some HER2/neu expression that have failed standard therapies with known benefit but for whom trastuzumab is not clinically indicated:

Patients with ovarian, colon, non-small cell lung, renal cell, bladder and prostate cancer that is known to be HER2 1+, 2+ or 3+ by IHC or have a VYSIS™ FISH result >1.8.

| HER2 Detection Method | Negative | Equivocal | Positive |
|---|---|---|---|
| VYSIS ™ FISH Ratio (Measures HER2 oncogene) | Ratio <1.8 | Ratio 1.8-<2.2 | Ratio >2.2 |
| IHC (Measures HER2 protein) | 0 | 1+-2+ | 3+ |

Patients with breast cancer that is known to be HER2 1+ or 2+ by IHC or with a VYSIS™ FISH result of 1.8-<2.2.

| HER2 Detection Method | Negative | Equivocal | Positive |
|---|---|---|---|
| VYSIS ™ FISH Ratio (Measures HER2 oncogene) | Ratio <1.8 | Ratio 1.8-<2.2 | Ratio >2.2 |
| IHC (Measures HER2 protein) | 0 | 1+-2+ | 3+ |

Adults at least 18 years of age with HER2+ bladder cancer in the adjuvant setting (adjuvant bladder cancer patients):

Tumor stage T3a, T3b, T4a, T4b and any node positive disease regardless of tumor stage.

Tumors that are HER2 1+, 2+ or 3+ by IHC or have a VYSIS™ FISH result >1.8.

Status-post primary cystectomy with curative intent.

May or may not have received neoadjuvant cisplatin-based combination chemotherapy.

May or may not have received adjuvant radiotherapy or chemotherapy based on pathologic risk per NCCN guidelines.

Greater than or equal to 6 weeks s/p primary surgery with curative intent.
Life expectancy of ≥6 months,
Performance Status: ECOG 0-1.
Naïve to trastuzumab, pertuzumab and lapatnib or other investigational HER2-directed therapies (e.g. T-DM1).
Recurrent or progressive disease on prior standard therapies with known clinical benefit (except adjuvant bladder cancer population).
For adults with recurrent, metastatic solid tumors: presence of measurable disease, defined as at least one lesion that can be accurately measured by CT scan in at least one dimension (longest diameter to be recorded for non-nodal lesions and short axis for nodal lesions) as ≥20 mm with conventional techniques and/or measurable, clinically visible skin lesions, with the exception of metastatic bladder cancer patients that have completed first line chemotherapy and may not have measurable disease.
Baseline LVEF by 2D Echocardiogram >55%.
Greater than or equal to 1 week since standard or investigational treatment for metastatic disease.
Stable, concurrent use of tamoxifen or aromatase inhibitors for ER+ status allowed.
Hematologic parameters: ANC ≥1000 cells/mm$^3$, ALC ≥500 cells/mm$^3$, Hemoglobin ≥9.0 gm/dL, WBC ≥2,500 cells/mm$^3$, platelet count ≥75,000/mm$^3$, PT/PTf ≤1.5× the upper limits of normal.
Chemistry parameters: SGOT and SGPT ≤3× the upper limits of normal and total bilirubin ≤1.5 mg/dl, Alk PO4 ≤2× the upper limits of normal (except for patients with documented metastatic disease to bone).
Negative serum HCG if female and of childbearing potential.
Negative serology for HIV-1.
Negative serology for hepatitis B and C unless the result is consistent with prior vaccination or prior infection with full recovery.
Willingness of female and male subjects to use effective contraception e.g. oral contraceptives, barrier device, intrauterine device, or condoms, during the study and for three months following the last dose of study vaccine.
Able to understand and provide Informed Consent.

Inclusion Part II
Age over 18 years
Breast cancer patients with 3+ HER2/neu expression by IHC or a VYSIS™ FISH result >2.2.

| HER2 Detection Method | Negative | Equivocal | Positive |
|---|---|---|---|
| VYSIS ™ FISH Ratio (Measures HER2 oncogene) | Ratio <1.8 | Ratio 1.8-<2.2 | Ratio >2.2 |
| IHC (Measures HER2 protein) | 0 | 1+-2+ | 3+ |

Recurrent or progressive metastatic disease after at least 1-2 courses of standard therapies with known clinical benefit, i.e. trastuzumab or lapatinib, ado-trastuzumah emtansine (TDM1) or other investigational HER2-directed therapies (e.g. MGAH22).
Life expectancy of ≥6 months.
Performance Status: ECOG 0-1.
Presence of measurable disease, defined as at least one lesion that can be accurately measured by CT scan in at least one dimension (longest diameter to be recorded for non-nodal lesions and short axis for nodal lesions) as >20 mm with conventional techniques and/or measurable clinical visible skin lesions.
Baseline LVEF by 2D Echocardiogram >55%.
Greater than or equal to 1 week since receipt of standard or investigational HER2-directed therapy for metastatic or recurrent disease.
Stable, concurrent use of tamoxifen or aromatase inhibitors for ER+ status allowed.
Hematologic parameters: ANC ≥1000 cells/mm$^3$. ALC ≥500 cells/mm$^3$, absolute Hemoglobin ≥29.0 gm/dL, WBC ≥2,500 cells/mm$^3$, platelet count ≥75,000/mm$^3$, PT/PT ≤1.5× the upper limits of normal.
Chemistry parameters: SGOT and SGPT ≤3×ULN, total bilirubin ≤1.5×ULN and Alk PO4≤2×ULN (except for patients with documented metastatic disease to bone).
Negative serum HCG if of childbearing potential.
Negative serology for HIV-1.
Negative serology for hepatitis B and C unless the result is consistent with prior vaccination or prior infection with full recovery.
Willingness of female subjects to use effective contraception e.g. oral contraceptives, barrier device, intrauterine device, or condoms, during the study and for three months following the last dose of study vaccine. We suggest that subjects do not become pregnant during the study, and for 3 months following receipt of the investigational AdHER2ECTM DC vaccine. (FDA requested language)
Able to understand and provide Informed Consent.

Exclusion Criteria
Females who are pregnant or breastfeeding.
Patients with active or previously treated CNS metastases or leptomeningeal involvement by tumor.
Patients with rapidly progressing disease in the opinion of the Principal Investigator.
Patients with inadequate bilateral peripheral venous or central venous catheter access for the required apheresis to allow generation of the autologous AdHER2ECTM DC vaccine product.
Clinically significant cardiac dysfunction defined as a history of >NYHA Class II symptoms, angina, congestive heart failure, myocardial infarction, arrhythmias or cardiac dysfunction requiring treatment or discontinuation of chemotherapy.
History of changes in baseline LVEF that occurred during prior treatment with trastuzumab.
Cumulative doxorubicin dose >400 mg/m$^2$ or cumulative epirubicin dose >800 mg/m.
Use of any standard chemotherapy or other investigational agent(s) within 1 week of study enrollment.
Use of systemic corticosteroid therapy within 2 weeks of study enrollment, including patients receiving replacement corticosteroid therapy. Note: only topical, inhaled and intranasal steroid therapy is permitted.
Active systemic viral, bacterial or fungal infection requiring treatment.

Study Schema and Design

This is an open label, single site, non-randomized, two part, phase I study of an autologous dendritic cell (DC) vaccine transduced with AdHER2ECTM to determine vaccine safety, immunogenicity and preliminary activity. Once enrollment eligibility is confirmed and informed consent is obtained, the patient is scheduled for a 15-18L mononuclear cell apheresis collection by counter-flow elutriation, aliquoted into at least 8 vials with about 333×10$^6$ cells/vial that are cryopreserved for future preparation of the autologous AdHER2ECTM DC vaccine product.

Part I N=30 patients

Part I of the study investigates vaccine dose escalation in adults with recurrent or progressive, metastatic solid tumors as well as adjuvant bladder cancer patients whose tumors are characterized by some HER2/neu expression but for whom trastuzumab is not clinically indicated:

Patients with ovarian, colon, non-small cell lung, renal cell, bladder and prostate cancer that is known to be HER2 1+, 2+ or 3+ by IHC, or have a VYSIS™ FISH result >1.8.

Patients with breast cancer that is known to be HER2 2+ or 3+ or with a VYSIS™ FISH result of <2.2.

Adjuvant bladder cancer patients are not enrolled in Part I of the study until AdHER2ECTM DC vaccine safety has been demonstrated out to 12 Weeks in at least 10 patients.

The goal of Part I is to determine whether there is a preliminary significant, adverse safety signal regarding cardiac toxicity in this patient population that is naïve to HER2-directed therapies, in addition to preliminary assessment of the vaccine's immunogenicity and clinical activity. Allowable tumors include breast, ovarian, colon, non-small cell lung, renal cell, bladder and prostate cancer. Inclusion of a broad spectrum of tumors that express HER2 facilitates more rapid accrual and allows prompt determination of the vaccine's safety and immunogenicity. However, the inclusion of subjects with multiple tumor types that have varying levels of HER2 expression may preclude identification of an optimal biologically active dose.

Dosage and Administration

This part of the study enrolls 6 patients per cohort in the vaccine dose cohorts outlined below:

Dose Cohort 1 (N=6 patients): $5 \times 10^6$ viable cells/vaccine
Dose Cohort 2 (N=6 patients): $10 \times 10^6$ viable cells/vaccine
Dose Cohort 3 (N=6 patients): $20 \times 10^6$ viable cells/vaccine Expansion to 12 more patients at the maximum tolerated dose if any indication of activity is found (total 30 patients).

Autologous AdHER2ECTM DC vaccine is administered intradermally at Weeks 0, 4, 8, 16 and 24. Re-staging for clinical evidence of stable disease, partial response or better by immune-related response criteria is assessed in observations at Weeks 8, 16, 24, 36 and 48 with confirmatory scans (if indicated to confirm irCR or irPR) at Weeks 12, 20, 28, 40 and 52. Adjuvant bladder cancer patients undergo re-staging for evidence of disease recurrence (with confirmatory scans 4 weeks later if recurrence is documented) at Weeks 8, 16, 24, 36 and 48. Vaccine dose escalation follows the procedures specified below.

Part II N=30 Patients

Part II of the study is conducted in adults with recurrent or progressive, metastatic breast cancer with 3+ HER2/neu expression by IHC or a VYSIS™ FISH result >2.2. Vaccine dose escalation is repeated in an identical manner in a population with significant prior exposure to trastuzumab, pertuzumab, lapatinib, ado-trastuzumab emtansine (TDM1) and other investigational HER2-directed therapies (e.g. MGAH22) to determine whether there is an adverse safety signal regarding cardiac toxicity, in addition to assessment of the vaccine's immunogenicity and clinical activity. Vaccine dose escalation, administration and re-staging assessment is identical to that conducted in Part I unless a vaccine dose MTD is identified in Part 1.

Proposed Dosage and Administration

Part II of the study enrolls 6 breast cancer patients per cohort in the vaccine dose cohorts outlined below:

Dose Cohort 1 (N=6 patients): $5 \times 10^6$ viable cells/vaccine
Dose Cohort 2 (N=6 patients): $10 \times 10^6$ viable cells/vaccine
Dose Cohort 3 (N=6 patients): $20 \times 10^6$ viable cells/vaccine Expansion to 12 more patients at the maximum tolerated dose if any indication of activity is found (total 30 patients).

Autologous AdHER2ECTM DC vaccine is administered intradermally at Weeks 0, 4, 8, 16 and 24. Re-staging for clinical evidence of stable disease, partial response or better by immune-related response criteria is assessed in observations at Weeks 8, 16, 24, 36 and 48 with confirmatory scans (if indicated to confirm iiCR or irPR) at Weeks 12, 20, 28, 40 and 52. Vaccine dose escalation follows the procedures specified below.

Dose Escalation

It has been reported that up to 7% of patients with HER2/neu expressing tumors treated with trastuzumab monotherapy for metastatic breast cancer developed clinically significant cardiac dysfunction including congestive heart failure. It would be considered acceptable if the therapeutic AdHER2ECTM DC vaccine proposed for this study would produce no greater than that level of cardiac toxicity, but not if it were to be exceeded. In order to evaluate this using a limited number of patients, a two-part design, but incorporating an early stopping rule, is implemented. The goal is to accrue 30 evaluable patients in each of Part I and Part II of the study and treat them with the experimental AdHER2ECTM DC vaccine. Unless an early stopping rule is invoked, the number of patients who have experienced a clinically significant cardiac toxicity is determined to estimate the frequency of cardiac toxicity. In addition, the dose level(s) at which toxicity is observed is also examined.

Dose escalation proceeds in cohorts of 6 patients. Dose escalation proceeds as long as 0 of 6 or 1 of 6 patients within a dose cohort have no evidence of toxicity and at least 3 of the 6 patients within a cohort have reached Week 12 on study. If 2 of 6 patients on any given dose cohort develop cardiac toxicity, that dose cohort is closed to further accrual, no higher doses are explored, and dose expansion of an additional 12 patients are enrolled in the next lower dose vaccine cohort to further assess for cardiac toxicity. The vaccine dose at which 0 to 1 of 18 treated patients develop cardiac toxicity is defined as the maximum tolerated dose (MTD). If two or more patients out of 18 at a given dose have developed cardiac toxicity, then the MTD has been exceeded at that dose, and the dose level below that one is considered the MTD. If enrollment in Cohort 3 is reached and 0 of 6 or 1 of 6 patients has toxicity, then this highest dose cohort is expanded by an additional 12 patients, for a maximum targeted accrual of 30 patients in Part 1.

If dose escalation has proceeded in all three cohorts in Part I and 0 to 2 of 30 patients have experienced cardiac toxicity, Part II of the study in patients with metastatic breast cancer and prior exposure to HER2-directed therapies proceeds in an identical manner to Part I. If a vaccine dose was found in Part I to have 2+/18 with cardiac toxicity, then the MTD from Part I is the vaccine dose used in Part 11 of the study. In this case there is no dose escalation and a maximum accrual of 30 patients is enrolled in Part II.

If no DLTs are observed, then dosing cohorts in Part 1 and Part II are assessed for the fraction of patients with immunogenicity and clinical outcomes to determine the biologically optimal vaccine dose that would be used in any future phase II studies involving those respective patient populations. To allow for the possibility of inevaluable patients, an accrual ceiling of 65 is used.

Study Modifications:

Part I Expansion Cohort (N=12) was increased from 20 million viable DCs per dose to 40 million viable DCs per dose as no there was evidence of an adverse safety signal.

Part II study cohort enrollment was modified to eliminate the $5\times10^6$ and $10\times10^6$ doses and being dosing at $20\times10^6$ viable DCs. and then proceed to an Expansion Cohort (N=24) dose of $40\Delta10^6$ viable DCs per dose.

Drug Administration

All patients undergo 15-18L apheresis to remove peripheral blood monocytes for dendritic cell preparation as well as peripheral blood mononuclear cells for flow cytometry and immunologic studies at their Week 0 visit. Cells used for subsequent dendritic cell maturation are derived from monocytes frozen during the initial apheresis. Autologous AdHER2ECTM dendritic cell vaccine is manufactured under cGMP conditions.

Autologous AdHER2ECTM DC vaccine preparations are assessed for release standards (nucleated cell content and concentration, appearance, flow cytometric verification of DC validation markers, viability $\geq 160\%$, and product sterility and safety testing) as well as for HER2 expression (percent of cells expressing HER2/neu and the ratio of geometric mean fluorescent intensity (MFI) of HER2/neu expression to isotype control).

For patients in both Part I and Part II of the study, autologous AdHER2ECTM DC vaccinations are dosed according to enrollment dosing cohort (5, 10 or $20\times10^6$ viable cells/vaccine) and administered intradermally in up to two injection sites at Weeks 0, 4, 8 and 24 for a total of four vaccinations. Vaccine is administered and patients are monitored for immediate adverse event vaccine reactions (VS, clinical assessment) for 2 hours following their first HER2 DC vaccine dose. If no adverse reactions are observed with the first vaccination, patients are monitored for 30 minutes for all subsequent vaccinations.

If an adverse reaction is observed following the first vaccination, the reaction is characterized and a determination made as to whether it is considered a dose limiting toxicity (DLT). If the adverse reaction is determined not to be a DLT, the duration of post-vaccination monitoring for subsequent vaccinations is determined as clinically indicated depending on the severity of the initial vaccine reaction.

All patients are given an AdHER2ECTM DC Vaccine Report Card and instructed on how to complete it, following each AdHER2ECTM DC vaccine dose. Enrollment into subsequent dosing cohorts for both Part I and Part II patients is staggered to allow for safety monitoring. Dose escalation proceeds as long as 0 of 6 or 1 of 6 patients within a dose cohort have no evidence of toxicity and at least 3 of the 6 patients within a cohort have reached Week 12 on study before enrollment in the next vaccine dose cohort can begin. If no dose limiting toxicities are observed in the twelve-week window inclusive of the first three vaccinations, enrollment of additional patients proceeds as outlined above.

Dose Modification and Immunization Stopping Rules

Unlike trastuzumab, the AdHER2ECTM vaccine targets both the EC and TM domains of HER2. Use of trastuzumab in women with breast cancer has been shown to be associated with a small, but significant risk (about 7%) for developing cardiac dysfunction. Exactly how trastuzumab causes cardiac toxicity is unknown. The goal of vaccination with this product is to stimulate the patient's own immune system to make antibodies (and also potentially killer cells) that recognize HER2. Prior to the present study, it was not known whether antibodies made by a person's own immune system would cause cardiac dysfunction. No dose modifications are made in patients receiving AdHER2ECTM DC vaccination. Subjects cease to receive immunization if they experience dose-limiting toxicity (DLT).

Supportive Management of Patients Experiencing DLT:

For patients experiencing Grade 2 or greater allergic or autoimmune DLT, supportive clinical intervention is provided until the DLT resolves to ≤Grade 1.

For patients experiencing Grade 2 or greater cardiac DLT, supportive clinical intervention is provided until the DLT resolves to ≤Grade 1.

Patients also undergo repeat LVEF measurements at 4-week intervals until LVEF returns to baseline function. Thereafter, cardiac function continues to be monitored until study Week 124.

Patients who experience Grade 2 or greater cardiac DLT that does not resolve to ≤Grade 1 continue to receive clinical support and be monitored until study Week 124.

For patients experiencing Grade 3 or greater organ (dermatologic, gastrointestinal, hepatic, pulmonary, renal/genitourinary or neurologic) DLT supportive clinical intervention is provided until the DLT resolves to ≤Grade 1.

For patients experiencing Grade 3 or greater anaphylaxis DLT, supportive clinical intervention is provided until the DLT resolves to ≤Grade 2.

For patients experiencing Grade 3 or greater local injection site reactions, supportive clinical intervention is provided until the DLT resolves to ≤Grade 1.

Criteria for Removal from Protocol Therapy and Off Study Criteria

Criteria for Removal from Protocol Therapy:

Completion of protocol therapy (receipt of 5 doses of autologous AdHER2ECTM DC vaccine) including a 60-day safety visit at Week 32.

Documentation of rapid disease progression at Week 0 repeat CT scans i.e. ≥20% increase in tumor burden (RECIST 1.1) between Week −5/Week −4 and Week 0. These patients are removed from study and precluded from receiving AdHER2ECTM DC vaccination.

Disease progression per immune-related response criteria (irRC) (Wolchok et al., *Clin Cancer Res* 15:7412-7420, 2009). Exception: Clinically stable patients with irPD with a ≥25% increase in tumor burden relative to Week −3/Week −2 baseline or nadir at Weeks 8, 16 or 24 re-staging are allowed to remain on study. Patients meeting the criteria for irPD at Week 36 restaging or later are removed from protocol therapy for progressive disease.

Patient experiences a dose limiting toxicity.

Patient experiences a Grade 3 or greater adverse event/toxicity that is deemed as possibly, probably or definitely related to AdHER2ECTM DC vaccination.

Patient experiences unresolved treatment-related toxicity.

Patient is taken off treatment for issues with DC vaccine manufacture e.g. insufficient recovery of dendritic cells to generate required vaccine dose, persistently decreased DC viability resulting in failure to meet vaccine release criteria, etc.

The patient experiences a treatment delay of more than 4 weeks from the scheduled target date for receipt of AdHER2ECTM DC vaccine.

Inter-current illness or medical circumstance (e.g. DVT) that in the opinion of the Principal Investigator unacceptably increases the risk of treatment The patient is non-compliant with study requirements.
The patient becomes too ill to return for protocol specified study visits.
The patient becomes pregnant during the study.
The patient requests to be withdrawn and refuses further therapy.
The patient requires a prohibited concomitant medication.
Death.

Continued Monitoring for Potential Cardiac Toxicity Once Off Protocol Therapy
Patient is removed from therapy for reasons outlined in Section 3.5.1.
Patient continues to undergo designated cardiac monitoring studies at subsequent study weeks.
Study Schema for cardiac troponin levels (Weeks 4, 8, 12, 16, 20, 24, 28, 32, 40 and 48) and echocardiograms (Weeks 4, 12, 20, 28, 32, 40, 48, 76, 100 and 124) including HPE and ECOG assessments.
Cardiac monitoring is performed.

Off Study Criteria
Completion of scheduled study visits.
Patient requests to be withdrawn and refuses further study participation.
The patient is non-compliant with study requirements.
The patient becomes too ill to return for protocol specified study visits.
Rapidly progressive disease as specified in 3.5.1.2
Death.

Concomitant Medications/Measures
Patients are allowed to be on concomitant therapy with tamoxifen or aromatase inhibitors for ER+ tumor status. Patients may be on concomitant drugs to prevent bone loss, including bisphosphonates and denosumab. Study subjects are allowed to take multivitamins, analgesics (NSAIDS or acetaminophen), antipyretics, and antihistamines for symptomatic relief of local or systemic injection site reactions. Patients are allowed to continue on medications as clinically indicated for treatment of chronic medical conditions e.g. hypertension, diabetes, hypercholesterolemia, etc.

Excluded Therapy: Trastuzumab, pertuzumab, lapatinib, ado-trastuzumab emtansine (TDM1) or other investigational HER2-directed therapies such as MGAH22 within 1 week of study enrollment.

Chemotherapy: Concomitant use of chemotherapy is not allowed during this trial.

Anti-Cancer Radionuclides: Concomitant use of anti-cancer radionuclides is not allowed during this trial. Patients are allowed to co-enroll in studies of novel radionuclide imaging agents e.g. $^{111}$Indium CHX-A DTPA trastuzumab.

Secondary Hormonal Therapies: Concomitant use of supplementary hormonal treatments other than tamoxifen or aromatse inhibitors is not allowed.

Corticosteroids: Concomitant, chronic systemic corticosteroids are not allowed during this trial (excepting emergent use for clinical indications). However, the use of inhaled corticosteroids, intranasal sprays and topical creams on limited body areas is allowed.

Vitamin D3 (Cholecalciferol) Supplementation
Vitamin D when ingested is metabolized in the liver to 25-OH vitamin D. Inside cells, it is metabolized further by 1-hydroxylase where it is transformed into a seco-steroid hormone that is important to a host of critical cellular and immune functions within the body. Within cells is a second enzyme 24-hydroxylase whose function is to decrease vitamin D, thereby maintaining intracellular vitamin D homeostasis. The classic function of vitamin D is to regulate calcium homeostasis and in turn, bone formation and resorption. However, additional functions of vitamin D have been demonstrated and include effects on immune response by promoting cellular apoptosis and differentiation. The exact role of vitamin D deficiency in prostate, breast, colon and other cancers has been controversial, with some laboratory studies suggesting there is a role and other epidemiological studies suggesting that there is no role or even possibly that supplementation should be avoided. In a recent study by Marshall and colleagues (Marshall et al., *J Clin Endocrinol Metabl* 97:2315-2324, 2012) vitamin D supplementation of 4.000 IU per day for one year was examined in men with low risk prostate cancer (Gleason score of 6, 1-6 cores positive out of 12 possible and a PSA <10) under active surveillance. After one year upon re-biopsy, 60% showed a decrease in the number of positive cores, Gleason score or both and in 6% these factors remained unchanged. In addition, PSA levels did not rise. In another study reported by Vieth and colleagues (Wagner et ed., LB-435, AACR Annual Meeting, Chicago, Ill., Apr. 3, 2012), 66 men scheduled to undergo radical prostatectomy were randomly assigned to receive a daily vitamin D dose of 400, 10,000 or 40.000 IU daily for 3 to 8 weeks prior to surgery. Calcitriol levels in the prostate increased progressively with increasing vitamin D dosing and corresponded with lower levels of Ki67 as well as higher levels of specific growth-inhibitor microRNAs.

Several studies have shown that women with low vitamin D levels have an increased risk of breast cancer incidence and mortality, but research is lacking investigating vitamin D levels and prognostic variables e.g. hormone receptor status, Oncotype DX etc. in this patient population. In a case control study of 194 women s/p breast cancer surgery and 194 cancer-free controls conducted by Peppone and colleagues (Peppone et al., *Ann Surg Oncol* 19(8):2590-2599, 2012), women with breast cancer were found to have significantly lower 25-OH vitamin levels than controls (32.7 ng/mL vs. 37.4 ng/mL respectively, P=0.02).

Women with suboptimal 25-OH vitamin D levels (<32 ng/mL) had significantly increased odds of having ER negative (OR=2.59, 95% confidence interval 195% CI)=1.08-6.23) and triple-negative cancer (OR=3.15, 95% CI=1.05-9.49) than those with optimal 25-OH D concentrations. In addition, women with basal-like phenotype had lower 25-OH vitamin D levels than women with luminal A phenotype (24.2 ng/mL vs. 32.8 ng/mL, respectively P=0.04). In summary, women with a more aggressive breast cancer molecular phenotype (basal-like) and worse prognostic indicators (ER- and triple-negative) had lower mean 25-OH vitamin D levels. Given its critical role in immune function and possible role in cancer pathophysiology, all patients have 25-OH vitamin D levels obtained at baseline. Although there is debate about the target level of 25-OH vitamin D for optimum health, most vitamin D experts agree that it should be greater than 40 ng/mL.

All patients with 25-OH vitamin D levels <40 ng/mL are initiated on oral supplements of Vitamin D3 (cholecalciferol) of either 2000 IU or 4000 IU daily dependent on the severity of vitamin D deficiency detected. 25-OH vitamin D levels continue to be monitored at study Weeks 8, 16, 28 and 52.

Response Criteria
Tumor measurements and evaluations for response are conducted (with confirmatory scans 4 weeks later if indicated) at Weeks 12 and 16, 28 and 32 and 48 and 52 and include physical examination, CT imaging and bone scan imaging (Weeks 28 and 48 only) studies. Responses are determined based on Immune-Related Response Criteria (irRC) (Wolchok et al., *Clin Cancer Res* 15:7412-7420, 2009). irRC are modified WHO criteria as outlined below. The overall response according to the irRC is derived from time-point response assessments (based on tumor burden) as follows:

irCR: complete disappearance of all lesions (whether measurable or not, and no new lesions) confirmed by a repeat, consecutive assessment no less than 4 weeks from the date first documented.

irPR: decrease in tumor burden ≥50% relative to baseline confirmed by a consecutive assessment at least 4 weeks after first documentation.

irSD: not meeting criteria for irCR or irPR, in absence of irPD.

irPD: increase in tumor burden ≥25% relative to nadir (minimum recorded tumor burden) confirmed by a repeat, consecutive assessment no less than 4 weeks from the date first documented.

Clinically stable patients with irPD with a ≥25% increase in tumor burden relative to nadir at Weeks 8, 16 or 24 re-staging are allowed to remain on study because of the unique response profile (initial tumor growth followed by regression) associated with AdHER2ECTM DC vaccination in pre-clinical animal studies. Patients meeting the criteria for irPD at Week 36 restaging or later are removed from the study for progressive disease.

Efficacy assessments are made. All objective responses have confirmatory scans performed at least 4 weeks after the response was first documented per irRC convention. All objective responses are reviewed and confirmed.

Response Definitions

Response and progression are evaluated in this study using the new Immune-Related Response Criteria as noted above. Note: Lesions are either measurable or non-measurable using the criteria for disease parameters outlined in section 6.2.2 below. The term "evaluable" in reference to measurability is used because it does not provide additional meaning or accuracy.

Disease Parameters

Measurable disease: Measurable lesions are defined as those that can be accurately measured in at least one dimension (longest diameter to be recorded) as ≥20 mm by chest x-ray, as ≥10 mm with CT scan, or ≥10 mm with calipers by clinical exam for measurable, clinically visible skin lesions. All tumor measurements are recorded in millimeters (or decimal fractions of centimeters). Tumor lesions that are situated in a previously irradiated area are not considered measurable unless they demonstrate progression.

Malignant lymph nodes: To be considered pathologically enlarged and measurable, a lymph node must be ≥15 mm in short axis when assessed by CT scan (CT scan slice thickness recommended to be no greater than 5 mm). At baseline and in follow-up, only the short axis is measured and followed.

Non-measurable disease: All other lesions (or sites of disease), including small lesions (longest diameter <10 mm or pathological lymph nodes with ≥10 to <15 mm short axis), are considered non-measurable disease. Bone lesions, leptomeningeal disease, ascites, pleural/pericardial effusions, lymphangitis cutis/pulmonitis, inflammatory breast disease, and abdominal masses (not followed by CT or MRI), are considered as non-measurable. Cystic lesions that meet the criteria for radiographically defined simple cysts are considered as malignant lesions (neither measurable nor non-measurable) since they are, by definition, simple cysts. 'Cystic lesions' thought to represent cystic metastases can be considered as measurable lesions, if they meet the definition of measurability described above. However, if non-cystic lesions are present in the same patient, these are preferred for selection as target lesions.

Target lesions: All measurable lesions up to a maximum of 2 lesions per organ and 5 lesions in total, representative of all involved organs, are identified as target lesions and recorded and measured at baseline. Target lesions are selected on the basis of their size (lesions with the longest diameter), are representative of all involved organs, but in addition are those that lend themselves to reproducible repeated measurements. It may be the case that, on occasion, the largest lesion does not lend itself to reproducible measurement in which circumstance the next largest lesion that can be measured reproducibly should be selected. A sum of the diameters (longest for non-nodal lesions, short axis for nodal lesions) for all target lesions is calculated and reported as the baseline sum diameters. If lymph nodes are to be included in the sum, then only the short axis is added into the sum. The baseline sum diameters are used as reference to further characterize any objective tumor regression in the measurable dimension of the disease.

Non-target lesions: All other lesions (or sites of disease) including any measurable lesions over and above the 5 target lesions are identified as non-target lesions and are recorded at baseline. Measurements of these lesions are not required, but the presence, absence, or in rare cases unequivocal progression of each are noted throughout follow-up.

Methods for Evaluation of Measurable Disease

All measurements are taken and recorded in metric notation using a ruler or calipers. All baseline evaluations are performed as closely as possible to the beginning of treatment and never more than 4 weeks before the beginning of the treatment. The same method of assessment and the same technique are used to characterize each identified and reported lesion at baseline and during follow-up. Imaging-based evaluation is preferred to evaluation by clinical examination unless the lesion(s) being followed cannot be imaged but are assessable by clinical exam.

Conventional CT: This guideline has defined measurability of lesions on CT scan based on the assumption that CT slice thickness is 5 mm or less. If CT scans have slice thickness greater than 5 mm, the minimum size for a measurable lesion should be twice the slice thickness.

Clinical lesions: Clinically visible skin lesions are utilized to evaluate measurable disease.

Chest x-ray: Chest x-ray is not utilized to evaluate measurable disease.

Ultrasound: Ultrasound is not utilized as a method of measurement

Response Criteria

Responses are determined based on Immune-Related Response Criteria (irRC). irRC are modified WHO criteria as outlined below. The overall response according to the irRC is derived from time-point response assessments (based on tumor burden) as follows:

irCR: complete disappearance of all lesions (whether measurable or not, and no new lesions) confirmed by a repeat, consecutive assessment no less than 4 weeks from the date first documented.

irPR: decrease in tumor burden 250% relative to baseline confirmed by a consecutive assessment at least 4 weeks after first documentation.

irSD: not meeting criteria for irCR or irPR, in absence of irPD.

irPD: increase in tumor burden ≥25% relative to nadir (minimum recorded tumor burden) confirmed by a repeat, consecutive assessment no less than 4 weeks from the date first documented.

Clinically stable patients with irPD with a ≥25% increase in tumor burden relative to nadir at Week 8, 16 and 24 re-staging are allowed to remain on study because of the unique response profile (initial tumor growth followed by regression) associated with AdHER2ECTM DC vaccination in pre-clinical animal studies. Patients meeting the criteria for irPD at Week 36 restaging or later are removed from the study for progressive disease.

Evaluation of Best Overall Response

The best overall response is the best response recorded from the start of the treatment until disease progression/recurrence (taking as reference for progressive disease the smallest measurements recorded since the treatment started). The patient's best response assignment depends on the achievement of both measurement and confirmation criteria. For the purposes of this study, best overall response is defined according to irRC.

Confirmatory Measurement/Duration of Response

Confirmation: To be assigned a status of irPR or irCR, changes in tumor measurements are confirmed by repeat assessments that are performed 4 weeks after the criteria for response are first met. In the case of irSD, repeat assessments are performed 4 weeks later for follow-up measurements to confirm that irSD criteria are again met. Progressive disease (irPD) must be confirmed by a second observation no less than 4 weeks later.

Duration of overall response: The duration of overall response is measured from the time measurement criteria are met for irCR or irPR (whichever is first recorded) until the first date that irPD is objectively documented. The duration of overall irCR is measured from the time measurement criteria are first met for irCR until the first date that recurrent disease is objectively documented. Time to progression (TIP) is also recorded for patients with irCR, irPR and irSD subsequently developing recurrent or progressive disease.

Duration of stable disease: Stable disease (irSD) is measured from the start of the treatment until the irPD criteria for progression are met.

Progression Free Survival and Overall Survival

Progression-free survival (PFS) is assessed only in adjuvant bladder cancer patients and in metastatic bladder cancer patients that have completed first line chemotherapy that do not have measurable disease. Overall survival (OS) is not being assessed as part of this clinical investigation.

Response Review

Responses are reviewed. Since the assessment of the preliminary anti-tumor activity of autologous AdHER2ECTM DC vaccination is only a secondary objective of this phase 1, two part dose escalation study, responses are not reviewed by an expert(s) independent of the study.

Pharmaceutical Information
ADSF35HER2ECTM (ADHER2)
Product Name: Ad5t35HER2ECTM
Vector Derivation The Ad5f35HER2ECTM vector was produced under cGMP conditions. The knob and fiber of Ad35 is substituted yielding a recombinant Ad5f35 vector that allows for greater viral tropism and more efficient transduction of human dendritic cells (DC).

Vector Manufacturing Summary

The vector was manufactured under cGMP conditions. The adenoviral vector was initially purified by two rounds of plaque isolation and then serially propagated on human embryonic kidney cells (HEK-293). The final amplified adenoviral vector was purified by ultracentrifugation using double cesium chloride gradients. Residual cesium chloride was removed by dialysis of the solution containing the vector against the formulation buffer.

Figure 2:
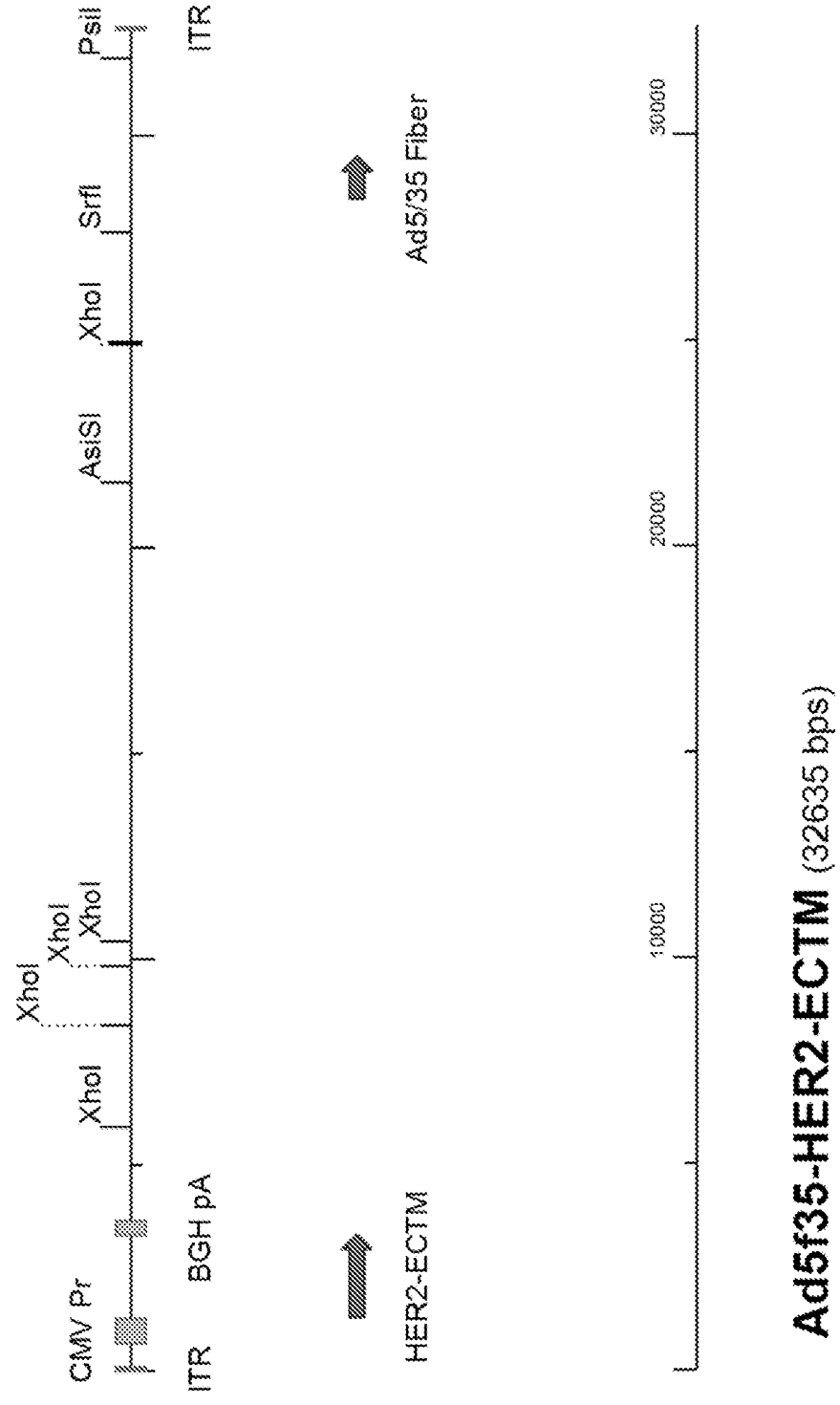
FIG. 2 is a map of the Ad5f35HER2ECTM vector. The nucleotide sequence of the vector is set forth herein as SEQ ID NO: 1.

An initial Master Virus Bank of Ad5f35HER2ECTM was generated (VM1003) and underwent two rounds of plaque purification with ultimate generation of purified Master Virus Bank Bulk Vector (VMB1003) which was subsequently used to produce the first clinical clot of vector that was then vialed for clinical use. The Adf535HER2ECTM clinical product is labeled VMC1003 and contains $1 \times 10^{12}$ viral particles/ml and 0.2 ml/vial. A map of the Ad5S35HER2ECTM vector is shown in FIG. 2 and the nucleotide sequence of the vector is set forth herein as SEQ ID NO: 1.

Toxicity

There is no known toxicity of the AdSf35HER2ECTM vector. It is a replication incompetent vector that does not integrate into the genomic DNA of the host cells it is used to transduce/transfect. Transduction of dendritic cells is associated with some reduction in cell viability that is highly donor dependent based on pre-clinical studies characterizing the proposed transduction process that is used in this study in normal donors.

Example 4: Use of AB Allogeneic Plasma

AB allogeneic plasma was obtained from healthy normal volunteer donors with blood type AB. The plasma was tested and confirmed to be negative for infectious pathogens, such as hepatitis A, B and C viruses, and human immunodeficiency virus (HIV). AB allogeneic plasma was heat inactivated (HI AB) and is used to culture monocytes into mature dendritic cells as an alternative to the use of autologous plasma (plasma from the patient) in the process of generating therapeutic dendritic cell (DC) vaccines. Thawed monocytes were re-suspended in media containing 90% RPMI-1640, 10% autologous HI plasma or HI AB allogeneic plasma, 2000 IU/ml IL-4, 2000 IUmL rGM-CSF and 10 mcg/mL gentamicin for initial culture.

In the process of investigating the AdHER2ECTM (AdHER2) dendritic cell vaccine platform in a Phase I clinical trial (see Examples above), it was determined that poor transduction efficiency and low expression of HER2, expressed as CD340% and CD340 MFI respectively, on the final dendritic cell vaccine product associated with the use of autologous plasma, could be improved and overcome by the use of heat inactivated AB allogeneic (unrelated) plasma. Not all subjects exhibited poor HER2/CD340 expression with the use of autologous plasma and the severity of poor expression varied among patients that were affected.

In addition to overcoming the poor HER2/CD340 transduction and expression on the final AdHER2 DC vaccine product, HI AB plasma also provides a foreign "danger signal" in the vaccine platform that triggers innate immunity and has the capacity to augment the development and intensity of immune responses to the ADHER2 DC vaccine when it was delivered intradermally.

As noted in FIG. 7, which provides an AdHER2 DC vaccine final product summary for all patients currently enrolled in the Phase I trial, the use of AB allogeneic plasma generally resulted in higher (often dramatically higher) HER2/CD340 transduction and expression in all patients tested.

Maximization of HER2 expression on the final DC vaccine product in addition to delivery of a co-stimulatory danger enhances the therapeutic effect of the vaccine.

Example 5: Phase I Clinical Study Results

In Part I of the two-part phase I study (NCT01730118) disclosed herein, subjects with HER2+ metastatic solid tumors naïve to HER2-targeted therapies received up to 5 doses of the AdHER2ECTM DC vaccine at weeks 0, 4, 8, 16 and 24. Dose escalation occurred in 3 cohorts of 6 or 7 patients, utilizing 5, 10 or $20\times10^6$ viable AdHER2ECTM transduced DCs per dose. Cohorts 1-3 were completed without dose-limiting or cardiac toxicity. Enrollment was initiated in an Expansion Cohort (N=12) with further dose escalation to $40\times10^6$ viable DCs per vaccine. Two bladder cancer patients were enrolled and received vaccination in the adjuvant setting at the 20 million DC dose after 12-week safety was documented in greater than 10 treated patients. Response was assessed using immune-related response criteria (irRC).

A total of 21 patients (7 colon, 5 ovarian, 3 bladder and 6 other cancer patients), having a median age of 60 years (a range of 36-72 years) and a median of 3 prior treatment regimens, received two or more vaccine doses (a median of 4 doses, range of 2-5 doses). The subjects included 14 female and 7 male subjects having HER2 IHC: 1+(N=6), 2+(N=8), or 3+(N=7). In Cohorts 1, 2 and 3, 0 of 6, 2 of 6 and 4 of 6 subjects received all 5 scheduled vaccines, respectively.

Patient responses showed evidence of a clinical benefit and anti-tumor activity, which is summarized in FIG. 8A. The following responses were observed in each cohort of Part I:

Cohort 1 ($5\times10^1$: No clinical response.

Cohort 2 ($10\times10^1$): One partial response (PR) in a gastroesophageal cancer patient (−71% lasting 44 weeks); and stable disease (SD) in two colon cancer patients lasting 24 and 28 weeks.

Cohort 3 ($20\times10^6$): One complete response (CR) (ongoing at 52 weeks) in an ovarian cancer patient, and one SD by irRC (ongoing at 36 weeks) in a patient with ovarian cancer.

Expansion Cohort ($40\times10^6$): No clinical response at week 12 in one patient with prostate cancer, no clinical response at week 18 in one patient with cervical cancer (evaluation ongoing).

In dose Cohorts 2 and 3, five of 11 metastatic patients had a CR, PR or SD for an overall disease control rate of 43%. Responses were observed in subjects with all ranges of HER2 expression. The two adjuvant bladder cancer patients remained without disease at 64 and 76 weeks.

Adverse events were limited to injection site reactions (all <G2) and no cardiac safety signal was detected with serial monitoring of LVEF by echocardiogram and serum Troponin T levels. Decreases in circulating tumor cells (CTCs) were observed at 12 weeks in 6 of 16 (38%) patients examined, including 3 of the 5 patients exhibiting disease control. These data show that the AdHER2ECTM DC vaccine is safe, well tolerated and is associated with anti-tumor activity, including decreases in circulating tumor cells.

The subjects of Part II are breast cancer patients with 3+ levels of HER2 expression who have failed multiple HER2-targeted therapies. Cohort 1 (five patients) received $20\times10^6$ viable DCs per dose. Three of the five patients (60%) meet the criteria for irSD; the other two patients have irPD, but are clinically stable. These results are summarized in FIG. 8B.

Taken together, these results demonstrate the AdHER2EC™ DC vaccine has a clinical benefit in 46% to 60% of patients with HER2+ advanced metastatic solid tumors that have failed a median of three prior chemotherapy regimens. This level of clinical benefit is unexpectedly high for a Phase I study. Response rates of 20-25% or less, with a limited duration of response, are typically observed in Phase I dose escalation studies, especially in heavily treatment-experienced populations with high metastatic disease burdens.

Example 6: Association of Circulating Tumor Cells (CTCs) Pre- and Post-AdHER2ECTM Dendritic Cell Vaccination with Overall Survival in Patients with Metastatic HER2' Solid Tumors Levels of CTCs have been associated with overall survival (OS) in metastatic breast (Cristofanilli et al., *N Engl J Med* 351:781-791, 2004) and prostate cancer (Scher et al., *J Clin Oncol* 33:1-9, 2015). This example describes associations between CTCs and OS in subjects that received the AdHER2ECTM autologous DC vaccine. The subjects in this study were adults with advanced metastatic tumors with 1-3+ HER2 expression.

Methods

In the open label, non-randomized, two-part phase I study (NCT01730118), CTC data were available on 18 subjects (11 female, 7 male, median age 57 years) with HER2+ solid tumors (8 colon cancer, 10 other cancers; IHC 1+N=3, 2+N=8, 3+N=7) that were naïve to HER2-targeted therapies; 16 had received at least 2 doses of the autologous AdHER2 DC vaccine delivered at Weeks 0, 4, 8, 16 and 24. Dose escalation occurred in cohorts of 6 patients utilizing $5\times10^6$. $10\times10^6$ and $20\times10^6$ viable DCs per vaccine. Epithelial cell adhesion molecule (EpCAM)+. CD45-CTCs from 10 ml of blood were detected by integrated magnetic pre-enrichment and flow cytometric analysis. CTCs were further characterized for expression of HER2 and the bone marrow homing molecule CXCR4.

Results

Figure 9A:
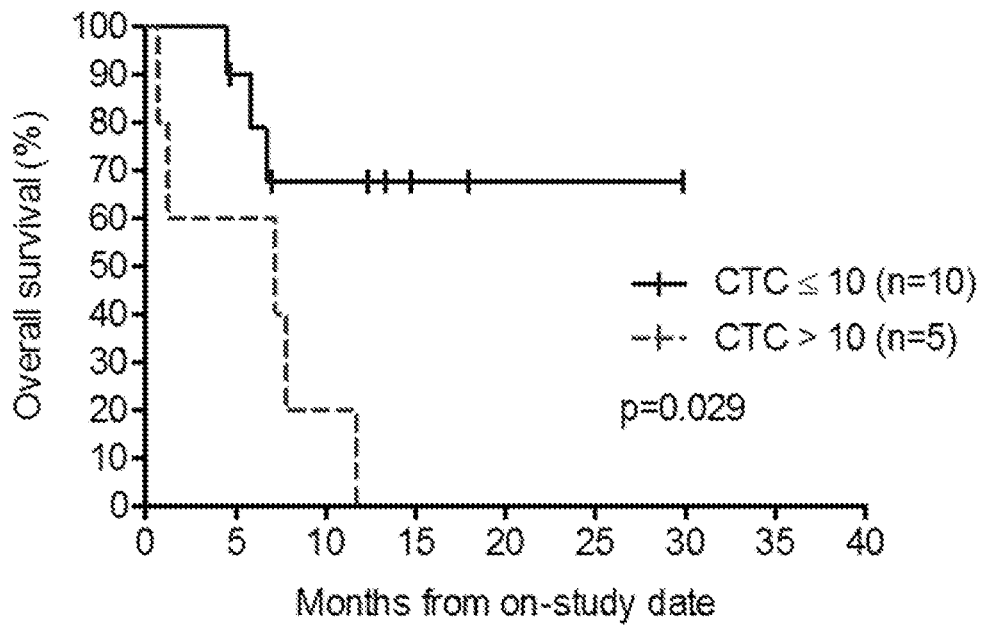
FIGS. 9A-9D are graphs showing an association between circulating tumor cells (CTCs) and overall survival in clinical study subjects administered the AdHER2ECTM DC vaccine. Subjects with HER2 IHC 2+ or 3+ expression (N=15) exhibited poorer overall survival when 11 or more HER2+ epithelial cell adhesion molecule (EpCAM)+ CTCs were detected per 10 ml of peripheral blood (FIG. 9A). Non-colorectal cancer (non-CRC) subjects (N=11) with 11 or more HER2+ EpCAM+ CTCs (FIG. 9B) or CXCR4+ EpCAM+ CTCs (FIG. 9C) per 10 ml of blood exhibited poorer overall survival (P=0.0046 and P=0.0067, respectively). In the non-CRC cohort, patients with stable or decreasing HER2+ EpCAM+ CTCs following treatment (N=9) had a trend toward improved OS (P=0.058) (FIG. 9D).
Figure 9B:
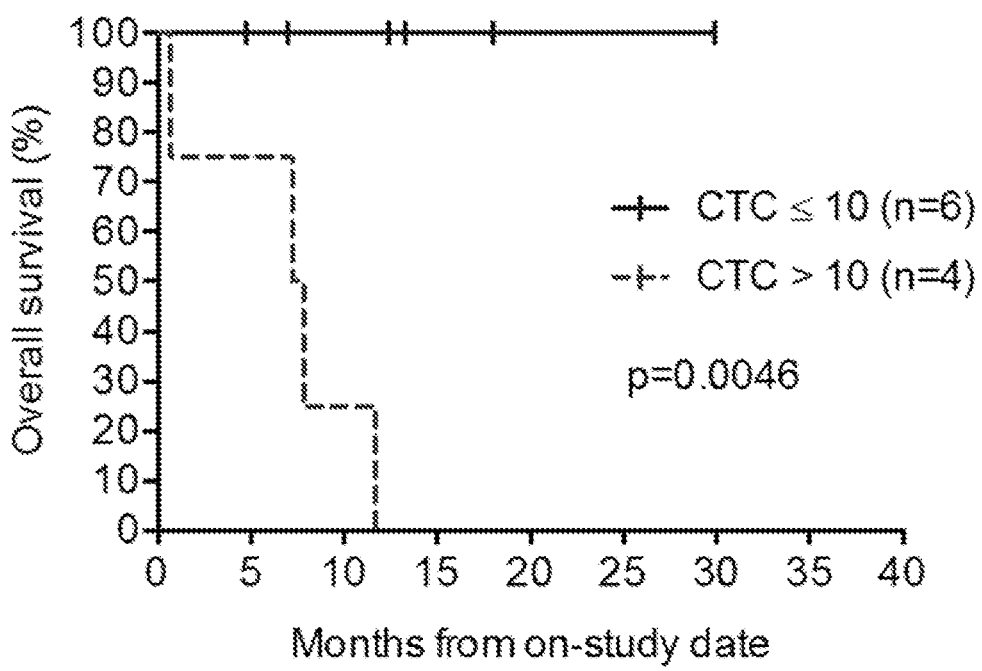
Figure 9C:
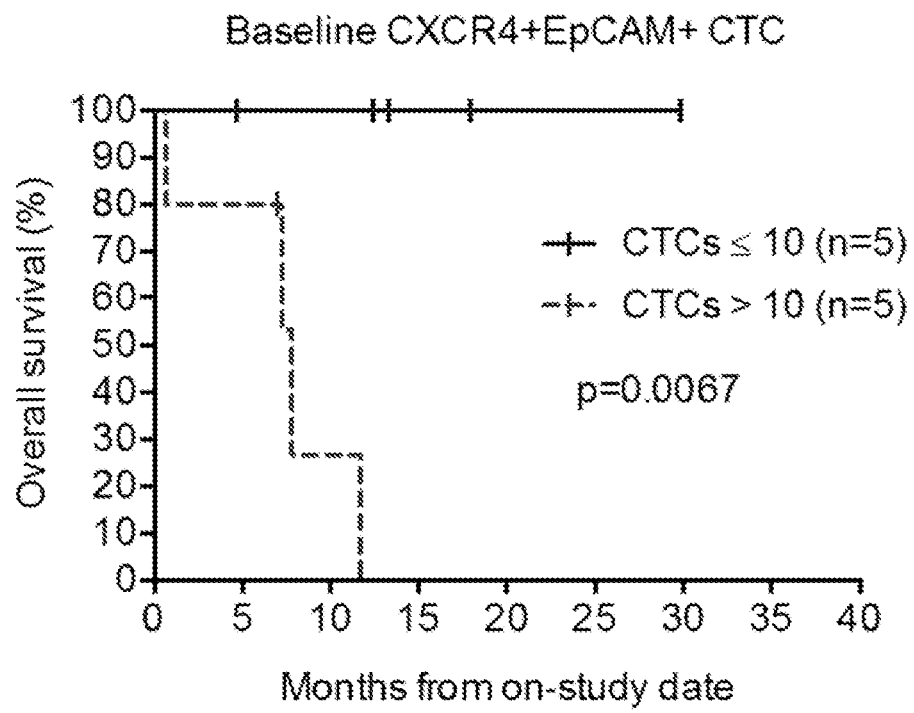
Figure 9D:
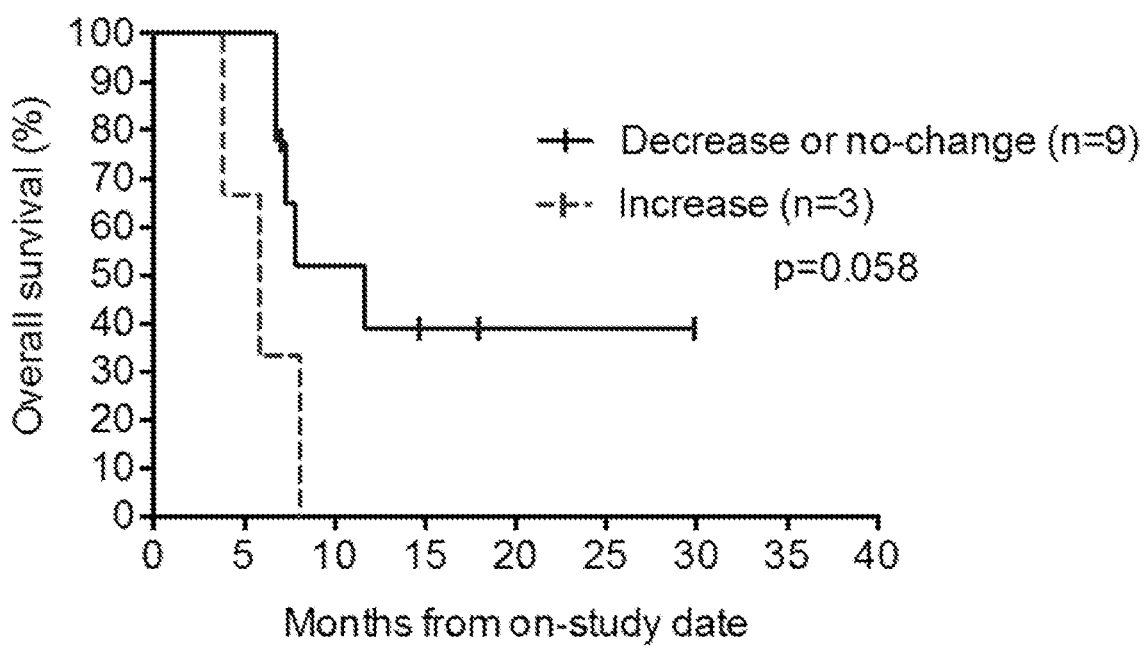

Of the 18 patients with advanced HER2+ metastatic tumors with specimens available for analysis, 17 (94%) had detectable EpCAM+ CTCs. In subjects with HER2 IHC 2+ or 3+ expression (N=15), those with 11 or more HER2+ EpCAM+ CTCs per 10 ml of peripheral blood had poorer overall survival (P=0.029) (FIG. 9A). In non-colorectal (CRC) cancer subjects (N=11), patients with 11 or more HER2+ EpCAM+ CTCs or CXCR4+ EpCAM+ CTCs per 10 ml of blood had poorer overall survival (P=0.0046 and P=0.0067, respectively) (FIGS. 9B and 9C, respectively). In this same non-CRC cohort, the HER2+ EpCAM+ CTC count showed a trend toward decrease at study Week 12 in 6 patients who had received 3 doses of AdHER2 DC vaccine (P=0.063). Patients with stable or decreasing HER2+ EpCAM+ CTCs following treatment (N=9) also had a trend toward better OS (P=0.058) (FIG. 9D).

These results demonstrate that in this population of patients with advanced, HER2+ metastatic solid tumors, greater than 11 HER2+ EpCAM+ CTCs at baseline is associated with poorer OS in patients with HER2 IHC 2+/3+ or non-CRC tumors. Stable or decreasing HER2+ EpCAM+ CTCs following AdHER2 vaccination is associated with a trend towards prolonged survival.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A recombinant adenovirus nucleic acid molecule encoding the extracellular (EC) and transmembrane (TM) domains of human HER2 and an adenovirus type 35 (Ad35) fiber protein, wherein the nucleic acid molecule comprises SEQ ID NO: 1.

2. A recombinant adenovirus produced by transforming isolated cells with the recombinant adenovirus nucleic acid molecule of claim 1.

3. A composition comprising isolated dendritic cells transduced with the recombinant adenovirus of claim 2.

4. The composition of claim 3, further comprising AB allogeneic plasma.

5. A method of treating a HER2-positive cancer in a subject, comprising:
administering to the subject a composition comprising autologous dendritic cells transduced with the recombinant adenovirus of claim 2 in a pharmaceutically acceptable carrier.

6. The method of claim 5, wherein the fiber protein comprises the amino acid sequence of SEQ ID NO: 3.

7. The method of claim 5, wherein the composition further comprises an adjuvant.

8. The method of claim 5, wherein the HER2-positive cancer is a breast cancer, ovarian cancer, colorectal cancer, prostate cancer, renal cell cancer, bladder cancer, gastroesophageal cancer, non-small cell lung cancer, sarcoma or ependymoma.

9. The method of claim 8, wherein the cancer is metastatic.

10. The method of claim 5, further comprising administering a checkpoint inhibitor.

11. The method of claim 10, wherein the checkpoint inhibitor is an anti-cytotoxic T lymphocyte-associated protein 4 (CTLA-4) agent, an anti-programmed cell death protein 1 (PD-1) agent, an anti-programmed death ligand 1 (PD-L1) agent, an anti-T cell immunoglobulin and mucin domain 3 (TIM-3) agent or an anti-lymphocyte activation gene 3 (LAG-3) agent.

12. The method of claim 11, wherein:
the anti-CTLA-4 agent is ipilimumab or tremelimumab;
the anti-PD-1 agent is pembrolizumab, nivolumab or CT-011; or
the anti-PD-L1 agent is avelumab or MEDI4736.

13. The method of claim 5, further comprising administering an antibody specific for an immune-inhibitory cytokine, an agent that inhibits or depletes regulatory T cells or myeloid suppressor cells, an oncolytic virus, a non-HER2 tumor antigen-specific vaccine, or any combination thereof.

14. The method of claim 5, further comprising administering radiation therapy, administering chemotherapy, performing surgical resection, administering β-mannosylceramide, or any combination thereof.

* * * * *